(12) United States Patent
Feng et al.

(10) Patent No.: US 11,993,591 B2
(45) Date of Patent: May 28, 2024

(54) CHROMEN-4-ONE DERIVATIVES FOR THE TREATMENT AND PROPHYLAXIS OF HEPATITIS B VIRUS DISEASE

(71) Applicant: Hoffmann-La Roche Inc., Little Falls, NJ (US)

(72) Inventors: Song Feng, Shanghai (CN); Chungen Liang, Shanghai (CN); Yongfu Liu, Shanghai (CN); Xuefei Tan, Shanghai (CN); Jun Wu, Shanghai (CN); Jianping Wang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/285,785

(22) PCT Filed: Oct. 17, 2019

(86) PCT No.: PCT/EP2019/078131
§ 371 (c)(1),
(2) Date: Apr. 15, 2021

(87) PCT Pub. No.: WO2020/079106
PCT Pub. Date: Apr. 23, 2020

(65) Prior Publication Data
US 2022/0402897 A1    Dec. 22, 2022

(30) Foreign Application Priority Data
Oct. 19, 2018   (WO) ................ PCT/CN2018/111037

(51) Int. Cl.
| | | |
|---|---|---|
| C07D 405/12 | (2006.01) |
| A61P 31/20 | (2006.01) |
| C07D 311/22 | (2006.01) |
| C07D 311/24 | (2006.01) |
| C07D 405/04 | (2006.01) |
| C07D 405/06 | (2006.01) |
| C07D 417/12 | (2006.01) |
| C07D 451/06 | (2006.01) |
| C07D 487/10 | (2006.01) |

(52) U.S. Cl.
CPC .......... *C07D 405/12* (2013.01); *A61P 31/20* (2018.01); *C07D 311/22* (2013.01); *C07D 311/24* (2013.01); *C07D 405/04* (2013.01); *C07D 405/06* (2013.01); *C07D 417/12* (2013.01); *C07D 451/06* (2013.01); *C07D 487/10* (2013.01)

(58) Field of Classification Search
CPC .. C07D 405/12; C07D 311/22; C07D 311/24; C07D 405/04; C07D 405/06; C07D 417/12; C07D 451/06; C07D 487/10
See application file for complete search history.

(56) References Cited

U.S. PATENT DOCUMENTS 8,815,878 B1    8/2014   Huberman
2015/0320702 A1* 11/2015  Chou .................. A61P 25/00
                                                514/655

FOREIGN PATENT DOCUMENTS

| CN | 105037194 A | 11/2015 |
| WO | 2004/004632 A2 | 1/2004 |
| WO | 2007/135592 A1 | 11/2007 |
| WO | 2013/127361 A1 | 9/2013 |
| WO | 2013/159243 A1 | 10/2013 |
| WO | 2017/202798 A1 | 11/2017 |
| WO | 2018/052967 A1 | 3/2018 |

OTHER PUBLICATIONS

Williams et al. ACS Chemical Neuroscience 2010, 1, 411-419 (Year: 2010).*
CAS Registry No. 2347515-91-5, which entered STN on Jun. 27, 2019 (Year: 2019).*
Gaspar et al. Biochemical Pharmacology 2012, 84, 21-29 (Year: 2012).*
National Center for Biotechnology Information. PubChem Compound Summary for CID 16013412, N-(5-chloro-2-methoxyphenyl)-6,8-dimethyl-4-oxo-4H-chromene-2-carboxamide. https://pubchem.ncbi.nlm.nih.gov/compound/16013412. Created Apr. 2, 2007; Accessed Sep. 1, 2023 (Year: 2007).*
National Center for Biotechnology Information. PubChem Bioassay Record for AID 1479, Source: National Center for Advancing Translational Sciences (NCATS). https://pubchem.ncbi.nlm.nih.gov/bioassay/1479. Deposited Jan. 7, 2009; Accessed Sep. 1, 2023 (Year: 2009).*
National Center for Biotechnology Information. PubChem Compound Summary for CID 35180228, N-(2-bromophenyl)-6,8-dichloro-4-oxo-4H-chromene-2-carboxamide. https://pubchem.ncbi.nlm.nih.gov/compound/35180228. Created May 29, 2009; Accessed Sep. 1, 2023 (Year: 2009).*
National Center for Biotechnology Information. PubChem Compound Summary for CID 35180234, 6,8-dichloro-4-oxo-N-[3-(trifluoromethyl)phenyl]-4H-chromene-2-carboxamide. https://pubchem.ncbi.nlm.nih.gov/compound/35180234. Created May 29, 2009; Accessed Sep. 1, 2023 (Year: 2009).*

(Continued)

*Primary Examiner* — Matthew P Coughlin

(57) ABSTRACT

The present invention provides novel compounds having the general formula (I) wherein $R^1$ to $R^6$, and m are as described herein, compositions including the compounds and methods of using the compounds.

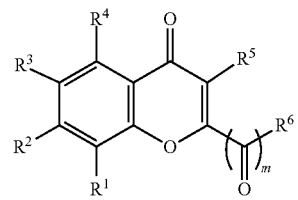

2 Claims, No Drawings
Specification includes a Sequence Listing.

(56) References Cited

OTHER PUBLICATIONS

National Center for Biotechnology Information. PubChem Compound Summary for CID 16013408, N-(2,5-dimethylphenyl)-6,8-dimethyl-4-oxo-4H-chromene-2-carboxamide. https://pubchem.ncbi.nlm.nih.gov/compound/16013408. Created Apr. 2, 2007; Accessed Sep. 1, 2023. (Year: 2007).*
Desideri et al., "In vitro evaluation of the anti-picornavirus activities of new synthetic flavonoids" Antivir. Chem. Chemother. 6(5):298-306 (Oct. 1, 1995) https://journals.sagepub.com/doi/pdf/10.1177/095632029500600503.
Ge Hyeong Lee et al., "Reaction of 2-Methylsulfonyl-4H-4-chromenones with Nucleophiles" Synth. Commun. 29(18):3155-3164 ( 1999).
International Preliminary Report on Patentability for PCT/EP2019/078131 dated Apr. 14, 2021.
International Search Report for PCT/EP2019/078131 dated Jan. 21, 2020.
Williams et al., "Re-exploration of the PHCCC Scaffold: Discovery of Improved Positive Allosteric Modulators of mGluR4" ACS Chem. 1:411-419 ( 2010).
Xiang and Wang et al., "Role of the PI3K-AKT-mTOR pathway in hepatitis B virus infection and replication" Molecular Medicine Reports 17(3):4713-4719 (Jan. 8, 2018) https://www.spandidos-publications.com/mmr/17/3/4713.
"Aurora Fine Chemicals etc." CAS Registry Database 1981268-36-3 (Search Report 2) (dated Aug. 28, 2016).
"Aurora Fine Chemicals etc." CAS Registry Database 2245128-25-8 (Search Report 1) (dated Oct. 16, 2018).
"Ukrorgsyntez Ltd. etc." CAS Registry Database 1626605-37-5 (Search Report 3) (dated Sep. 26, 2016).

* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: HBV-Forward Primer

<400> SEQUENCE: 1
```

```
aagaaaaacc ccgcctgtaa                                                    20

<210> SEQ ID NO 2
<211> LENGTH: 23
<212> TYPE: DNA
<213> ORGANISM: Artificial Sequence
<220> FEATURE:
<223> OTHER INFORMATION: HBV-Reverse Primer

<400> SEQUENCE: 2
cctgttctga ctactgcctc tcc                                                23

<210> SEQ ID NO 3
<211> LENGTH: 27
<212> TYPE: DNA
<213> ORGANISM: Artificial Sequence
<220> FEATURE:
<223> OTHER INFORMATION: HBV-Probe

<400> SEQUENCE: 3
cctgatgtga tgttctccat gttcagc                                            27
```

CHROMEN-4-ONE DERIVATIVES FOR THE TREATMENT AND PROPHYLAXIS OF HEPATITIS B VIRUS DISEASE

The present invention relates to organic compounds useful for therapy and/or prophylaxis of HBV infection in a mammal, and in particular to cccDNA (covalently closed circular DNA) inhibitors useful for treating HBV infection.

FIELD OF THE INVENTION

The present invention relates to novel chromen-4-one derivatives having pharmaceutical activity, their manufacture, pharmaceutical compositions containing them and their potential use as medicaments.

The present invention relates to compounds of formula (I)

wherein $R^1$ to $R^6$, and m are as described below, or a pharmaceutically acceptable salt thereof.

Hepatitis B virus (HBV) infection is one of the most prevalent viral infections and is a leading cause of chronic hepatitis. It is estimated that worldwide, around 2 billion people have evidence of past or present infection with HBV. Over 250 million individuals are currently chronically infected with HBV and are therefore at high risk to develop liver fibrosis, cirrhosis and hepatocellular carcinoma (HCC). There are data to indicate ~800,000 deaths per year are directly linked to HBV infection (Lozano, R. et al., Lancet (2012), 380 (9859), 2095-2128; Goldstein, S. T. et al., Int J Epidemiol (2005), 34 (6), 1329-1339).

Many countries in the world administer hepatitis B vaccine starting at birth or in early childhood, which has greatly reduced the incidence and prevalence of hepatitis B in most endemic regions over the past few decades. However the vaccine has no impact on people who were infected before the widely use of the vaccine in developing end-stage liver disease or HCC (Chen, D. S., J Hepatol (2009), 50 (4), 805-816). Vaccination at birth of infants born to HBV positive mothers is usually not sufficient for protecting vertical transmission and combination with hepatitis B immune globulin is needed (Li, X. M. et al., World J Gastroenterol (2003), 9 (7), 1501-1503).

Currently FDA-approved treatments for chronic hepatitis B include two type 1 interferons (IFN) which are IFNalfa-2b and pegylated IFN alfa-2a and six nucleos(t)ide analogues (NAs) which are lamivudine (3TC), tenofovir disoproxil fumarate (TDF), adefovir (ADV), telbivudine (LdT), entecavir (ETV), and vemlidy (tenofovir alafenamide (TAF)). IFN treatment is finite, but it is known to have severe side effects, and only a small percentage of patients showed a sustained virological response, measured as loss of hepatitis B surface antigen (HBsAg). NAs are inhibitors of the HBV reverse transcriptase, profoundly reduce the viral load in vast majority of treated patients, and lead to improvement of liver function and reduced incidence of liver failure and hepatocellular carcinoma. However, the treatment of NAs is infinite (Ahmed, M. et al., Drug Discov Today (2015), 20 (5), 548-561; Zoulim, F. and Locarnini, S., Gastroenterology (2009), 137 (5), 1593-1608 e1591-1592).

HBV chronic infection is caused by persistence of covalently closed circular (ccc)DNA, which exists as an episomal form in hepatocyte nuclei. cccDNA serves as the template for viral RNA transcription and subsequent viral DNA generation. Only a few copies of cccDNA per liver cell can establish or re-initiate viral replication. Therefore, a complete cure of chronic hepatitis B will require elimination of cccDNA or permanently silencing of cccDNA. However, cccDNA is intrinsically very stable and currently available therapeutics could not eliminate cccDNA or permanently silence cccDNA (Nassal, M., Gut (2015), 64 (12), 1972-1984; Gish, R. G. et al., Antiviral Res (2015), 121, 47-58; Levrero, M. et al., J Hepatol (2009), 51 (3), 581-592). The current SoC could not eliminate the cccDNA which are already present in the infected cells.

There is an urgent need to discover and develop new anti-HBV reagents to eliminate or permanently silence cccDNA, the source of chronicity (Ahmed, M. et al., Drug Discov Today (2015), 20 (5), 548-561; Nassal, M., Gut (2015), 64 (12), 1972-1984).

SUMMARY OF THE INVENTION

Objects of the present invention are novel compounds of formula (I), their manufacture, medicaments based on a compound in accordance with the invention and their production as well as the use of compounds of formula (I) as cccDNA inhibitors and for the treatment or prophylaxis of HBV infection. The compounds of formula (I) show superior anti-HBV activity. In addition, the compounds of formula (I) also show good safety and good PK profiles.

The present invention relates to a compound of formula (I)

Wherein
$R^1$ is H, halogen or $C_{1-6}$alkyl;
$R^2$ is H, halogen or $C_{1-6}$alkyl;
$R^3$ is H, halogen or $C_{1-6}$alkyl;
$R^4$ is H, halogen or $C_{1-6}$alkyl;
$R^5$ is H, halogen or $C_{1-6}$alkyl;
m is 0 or 1;
$R^6$ is -L-Cy$^1$, or Cy$^2$; wherein
   L is —N($R^7$)—X—, -continued

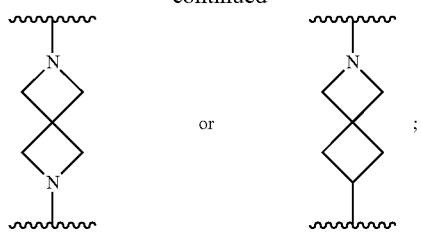

wherein

R[7] is H or $C_{1-6}$alkyl;

X is a bond or —C(R[x1]R[y1])—; wherein R[x1] is H or $C_{1-6}$alkyl, R[y1] is H or $C_{1-6}$alkyl;

$Cy^1$ is phenyl, thiadiazolyl, pyridyl, phenyl$C_{1-6}$alkyl, phenyl$C_{1-6}$alkoxy or phenylcarbonyl; wherein phenyl, thiadiazolyl, pyridyl, phenyl$C_{1-6}$alkyl, phenyl$C_{1-6}$alkoxy and phenylcarbonyl are unsubstituted or substituted by one or two or three substituents independently selected from halogen, hydroxy, carboxy, —$NO_2$, $C_{1-6}$alkyl, halo$C_{1-6}$alkyl, $C_{1-6}$alkoxy, carboxy$C_{3-7}$cycloalkoxy, carboxy$C_{1-6}$alkoxy, (carboxy$C_{1-6}$alkoxy)$C_{1-6}$alkoxy, $C_{1-6}$alkoxycarbonyl, (carboxy$C_{3-7}$cycloalkoxy)$C_{1-6}$alkoxy and ($C_{1-6}$alkoxycarbonyl$C_{3-7}$cycloalkoxy)$C_{1-6}$alkoxy;

$Cy^2$ is isoindolinyl, 3,4-dihydro-1H-isoquinolinyl, 3,4-dihydro-2H-quinolinyl, piperidyl, 2,6-diazaspiro[3.3]heptanyl, 2-azaspiro[3.3]heptanyl or 8-azabicyclo[3.2.1]octanyl; wherein isoindolinyl, 3,4-dihydro-1H-isoquinolinyl, 3,4-dihydro-2H-quinolinyl, piperidyl, 2,6-diazaspiro[3.3]heptanyl, 2-azaspiro[3.3]heptanyl and 8-azabicyclo[3.2.1]octanyl are unsubstituted or substituted by one or two or three substituents independently selected from OH, halogen, $C_{1-6}$alkyl, $C_{1-6}$alkoxy, —$NO_2$, (carboxy$C_{1-6}$alkoxy)$C_{1-6}$alkoxy, (carboxy$C_{3-7}$cycloalkoxy)$C_{1-6}$alkoxy, $C_{1-6}$alkoxycarbonyl, ($C_{1-6}$alkoxycarbonyl$C_{3-7}$cycloalkoxy)$C_{1-6}$alkoxy and oxo;

or a pharmaceutically acceptable salt thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl. More particularly, "$C_{1-6}$alkyl" group is methyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "$C_{1-6}$alkoxy" groups are methoxy, ethoxy and propoxy. More particularly, "$C_{1-6}$alkoxy" group is methoxy or ethoxy.

The term "$C_{3-7}$cycloalkyl" denotes to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" group is cyclopropyl, cyclobutyl or cyclopentyl.

The term "$C_{3-7}$cycloalkoxy" denotes a group $C_{3-7}$cycloalkyl-O—, wherein the "$C_{3-7}$ cycloalkyl" is as defined above; for example cyclopropoxy, cyclobutoxy, cyclopentoxy.

Particular "$C_{3-7}$cycloalkoxy" group is cyclobutoxy.

The term "halogen" and "halo" are used interchangeably herein and denote fluoro, chloro, bromo, or iodo.

The term "halo$C_{1-6}$alkyl" denotes an alkyl group wherein at least one of the hydrogen atoms of the alkyl group is replaced by same or different halogen atoms, particularly fluoro atoms. Examples of halo$C_{1-6}$alkyl include monochloro-, difluoro- or trifluoro-methyl, -ethyl or -propyl, for example difluoromethyl and trifluoromethyl.

The term "carbonyl" alone or in combination refers to the group —C(O)—.

The term "bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "oxo" means an =O group and may be attached to a carbon atom or a sulfur atom.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula (I).

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

cccDNA Inhibitors

The present invention provides (i) a compound having the general formula (I):

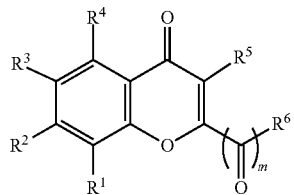
(I)

Wherein
R$^1$ is H, halogen or C$_{1-6}$alkyl;
R$^2$ is H, halogen or C$_{1-6}$alkyl;
R$^3$ is H, halogen or C$_{1-6}$alkyl;
R$^4$ is H, halogen or C$_{1-6}$alkyl;
R$^5$ is H, halogen or C$_{1-6}$alkyl;
m is 0 or 1;
R$^6$ is -L-Cy$^1$, or Cy$^2$; wherein
L is —N(R$^7$)—X—,

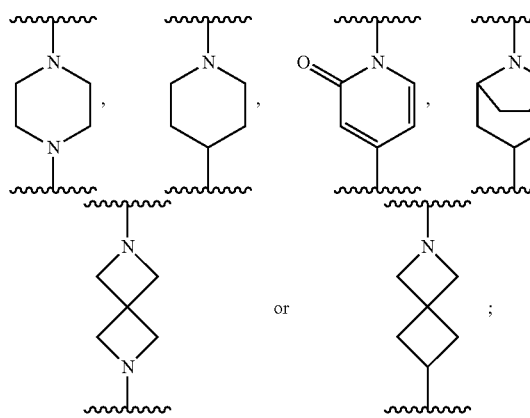

wherein
R$^7$ is H or C$_{1-6}$alkyl;
X is a bond or —C(R$^{x1}$R$^{y1}$)—; wherein R$^{x1}$ is H or C$_{1-6}$alkyl, R$^{y1}$ is H or C$_{1-6}$alkyl;
Cy$^1$ is phenyl, thiadiazolyl, pyridyl, phenylC$_{1-6}$alkyl, phenylC$_{1-6}$alkoxy or phenylcarbonyl; wherein phenyl, thiadiazolyl, pyridyl, phenylC$_{1-6}$alkyl, phenylC$_{1-6}$alkoxy and phenylcarbonyl are unsubstituted or substituted by one or two or three substituents independently selected from halogen, hydroxy, carboxy, —NO$_2$, C$_{1-6}$alkyl, haloC$_{1-6}$alkyl, C$_{1-6}$alkoxy, carboxyC$_{3-7}$cycloalkoxy, carboxyC$_{1-6}$alkoxy, (carboxyC$_{1-6}$alkoxy)C$_{1-6}$alkoxy, C$_{1-6}$alkoxycarbonyl, (carboxyC$_{3-7}$cycloalkoxy)C$_{1-6}$alkoxy and (C$_{1-6}$alkoxycarbonylC$_{3-7}$cycloalkoxy)C$_{1-6}$alkoxy;
Cy$^2$ is isoindolinyl, 3,4-dihydro-1H-isoquinolinyl, 3,4-dihydro-2H-quinolinyl, piperidyl, 2,6-diazaspiro[3.3]heptanyl, 2-azaspiro[3.3]heptanyl or 8-azabicyclo[3.2.1]octanyl; wherein isoindolinyl, 3,4-dihydro-1H-isoquinolinyl, 3,4-dihydro-2H-quinolinyl, piperidyl, 2,6-diazaspiro[3.3]heptanyl, 2-azaspiro[3.3]heptanyl and 8-azabicyclo[3.2.1]octanyl are unsubstituted or substituted by one or two or three substituents independently selected from OH, halogen, C$_{1-6}$alkyl, C$_{1-6}$alkoxy, —NO$_2$, (carboxyC$_{1-6}$alkoxy)C$_{1-6}$alkoxy, (carboxyC$_{3-7}$cycloalkoxy)C$_{1-6}$alkoxy, C$_{1-6}$alkoxycarbonyl, (C$_{1-6}$alkoxycarbonylC$_{3-7}$cycloalkoxy)C$_{1-6}$alkoxy and oxo;
or a pharmaceutically acceptable salt thereof.

A further embodiment of the present invention is (ii) a compound of formula (I) according to (i), wherein
R$^1$ is H, F, Cl, Br, I or methyl;
R$^2$ is H, F, Cl, Br, I or methyl;
R$^3$ is H, F, Cl, Br, I or methyl;
R$^4$ is H, F, Cl, Br, I or methyl;
R$^5$ is H, F, Cl, Br, I or methyl;
m is 0 or 1;
R$^6$ is -L-Cy$^1$, or Cy$^2$;
L is —N(R$^7$)—X—,

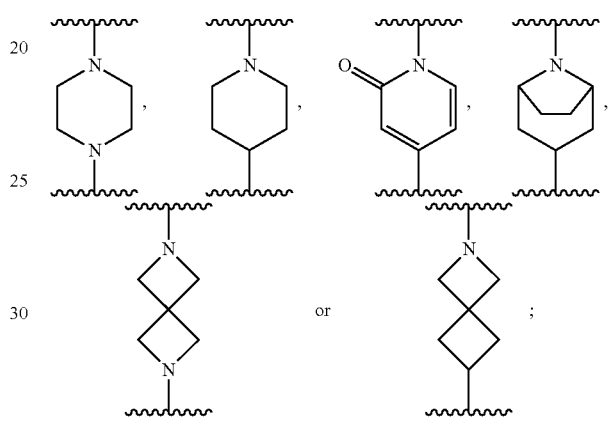

wherein
R$^7$ is H or methyl;
X is a bond or —C(R$^{x1}$R$^{y1}$)—; wherein R$^{x1}$ is H or methyl, R$^{y1}$ is H or methyl;
Cy$^1$ is phenyl, 1,3,4-thiadiazol-2-yl, 2-pyridyl, phenylmethyl, phenylmethoxy or phenylcarbonyl; wherein phenyl, 1,3,4-thiadiazol-2-yl, 2-pyridyl, phenylmethyl, phenylmethoxy and phenylcarbonyl are unsubstituted or substituted by one or two or three substituents independently selected from F, Cl, Br, CF$_3$, hydroxy, —NO$_2$, carboxy, methyl, methoxy, carboxycyclobutoxy, carboxypropoxy, carboxymethoxy, (carboxymethoxy)ethoxy, methoxycarbonyl, (carboxycyclobutoxy)ethoxy, ethoxycarbonyl and (methoxycarbonylcyclobutoxy)ethoxy;
Cy$^2$ is isoindolin-2-yl, 3,4-dihydro-1H-isoquinolin-2-yl, 3,4-dihydro-2H-quinolin-1-yl, 1-piperidyl, 2,6-diazaspiro[3.3]heptan-2-yl, 2-azaspiro[3.3]heptan-2-yl or 8-azabicyclo[3.2.1]octan-8-yl; wherein isoindolin-2-yl, 3,4-dihydro-1H-isoquinolin-2-yl, 3,4-dihydro-2H-quinolin-1-yl, 1-piperidyl, 2,6-diazaspiro[3.3]heptan-2-yl, 2-azaspiro[3.3]heptan-2-yl and 8-azabicyclo[3.2.1]octan-8-yl are unsubstituted or substituted by one or two or three substituents independently selected from F, Cl, Br, OH, methyl, methoxy, —NO$_2$, (carboxymethoxy)ethoxy, tert-butoxycarbonyl, (carboxycyclobutoxy)ethoxy, (methoxycarbonylcyclobutoxy)ethoxy and oxo;
or a pharmaceutically acceptable salt thereof.

A further embodiment of the present invention is (iii) a compound of formula (I) according to (i), or a pharmaceutically acceptable salt thereof, wherein R¹ is H or halogen;
R² is H;
R³ is H or halogen;
R⁴ is H;
R⁵ is H or $C_{1-6}$alkyl;
m is 1;
R⁶ is -L-Cy¹; wherein
　L is —NH—X—, wherein X is a bond or —C(R^{x1}R^{y1})—; wherein R^{x1} is H or $C_{1-6}$alkyl, R^{y1} is H;
　Cy¹ is phenyl, thiadiazolyl or pyridyl; wherein phenyl, thiadiazolyl and pyridyl are substituted by one or two substituents independently selected from halogen, hydroxy, carboxy, $C_{1-6}$alkyl, halo$C_{1-6}$alkyl, $C_{1-6}$alkoxy, carboxy$C_{3-7}$cycloalkoxy, carboxy$C_{1-6}$alkoxy, (carboxy$C_{1-6}$alkoxy)$C_{1-6}$alkoxy, $C_{1-6}$alkoxycarbonyl and (carboxy$C_{3-7}$cycloalkoxy)$C_{1-6}$alkoxy.

A further embodiment of the present invention is (iv) a compound of formula (I) according to (i), or a pharmaceutically acceptable salt thereof, wherein
R¹ is H or Cl;
R² is H;
R³ is H or Cl;
R⁴ is H;
R⁵ is H or methyl;
m is 1;
　L is —NH—X—, wherein X is a bond or —C(R^{x1}R^{y1})—; wherein R^{x1} is H or methyl, R^{y1} is H;
　Cy¹ is phenyl, 1,3,4-thiadiazol-2-yl or 2-pyridyl; wherein phenyl, 1,3,4-thiadiazol-2-yl and 2-pyridyl are substituted by one or two substituents independently selected from F, Cl, Br, CF₃, hydroxy, carboxy, methyl, methoxy, carboxycyclobutoxy, carboxypropoxy, carboxymethoxy, (carboxymethoxy)ethoxy, methoxycarbonyl, (carboxycyclobutoxy)ethoxy and ethoxycarbonyl.

A further embodiment of the present invention is (v) a compound of formula (I) according to (i), or a pharmaceutically acceptable salt thereof, wherein Cy¹ is phenyl; wherein phenyl is substituted by one or two substituents independently selected from halogen and $C_{1-6}$alkyl.

A further embodiment of the present invention is (vi) a compound of formula (I) according to (i), or a pharmaceutically acceptable salt thereof, wherein phenyl is substituted by one or two substituents independently selected from Cl and methyl.

In another embodiment (vii) of the present invention, particular compounds of the present invention are selected from:
3-(2-(4-(8-chloro-4-oxo-chromene-2-carboxamido)-3-fluorophenoxy)ethoxy)cyclobutanecarboxylic acid;
3-(2-(4-(8-chloro-4-oxo-chromene-2-carboxamido)-3-methylphenoxy)ethoxy)cyclobutanecarboxylic acid;
6-chloro-N-(4-chloro-2-methylphenyl)-3-methyl-4-oxo-chromene-2-carboxamide;
3-(2-(4-(8-chloro-4-oxo-chromene-2-carboxamido)-3-(trifluoromethyl)phenoxy)ethoxy)cyclobutanecarboxylic acid;
8-chloro-4-oxo-N-(5-(trifluoromethyl)-1,3,4-thiadiazol-2-yl)-chromene-2-carboxamide; 3-(5-chloro-2-(8-chloro-4-oxo-chromene-2-carboxamido)phenoxy)cyclobutane-1-carboxylic acid;
8-chloro-N-(4-chloro-2-methylphenyl)-4-oxo-chromene-2-carboxamide;
8-chloro-N-(2,4-dichlorobenzyl)-4-oxo-chromene-2-carboxamide;
N-(5-bromo-3-methylpyridin-2-yl)-8-chloro-4-oxo-chromene-2-carboxamide;
4-(5-chloro-2-(6,8-dichloro-4-oxo-chromene-2-carboxamido)phenoxy)butanoic acid;
8-chloro-N-(4-chloro-2-(trifluoromethyl)phenyl)-4-oxo-chromene-2-carboxamide;
6,8-dichloro-N-(4-chloro-2-methylphenyl)-4-oxo-chromene-2-carboxamide;
8-chloro-4-oxo-N-(o-tolyl)-chromene-2-carboxamide;
4-(8-chloro-4-oxo-chromene-2-carboxamido)-3-methylbenzoic acid;
2-(2-(4-(8-chloro-4-oxo-chromene-2-carboxamido)-3-methylphenoxy)ethoxy)acetic acid;
2-(5-chloro-2-(8-chloro-4-oxo-chromene-2-carboxamido)phenoxy)acetic acid;
methyl 3-(8-chloro-4-oxo-chromene-2-carboxamido)-4-methylbenzoate;
2-(2-(5-chloro-2-(6,8-dichloro-4-oxo-chromene-2-carboxamido)phenoxy)ethoxy)acetic acid;
N-(5-bromo-4-methylpyridin-2-yl)-8-chloro-4-oxo-chromene-2-carboxamide;
2-(2-(5-chloro-2-(8-chloro-4-oxo-chromene-2-carboxamido)phenoxy)ethoxy)acetic acid;
methyl 5-chloro-2-(8-chloro-4-oxo-chromene-2-carboxamido)benzoate;
methyl 4-((8-chloro-4-oxo-chromene-2-carboxamido)methyl)benzoate;
methyl 4-(8-chloro-4-oxo-chromene-2-carboxamido)-3-methylbenzoate;
N-(1-(4-bromophenyl)ethyl)-8-chloro-4-oxo-chromene-2-carboxamide;
8-chloro-N-(4-hydroxy-2-methylphenyl)-4-oxo-chromene-2-carboxamide;
N-(5-bromo-3-methoxypyridin-2-yl)-8-chloro-4-oxo-chromene-2-carboxamide;
3-(2-(5-chloro-2-(8-chloro-4-oxo-chromene-2-carboxamido)phenoxy)ethoxy)cyclobutane-1-carboxylic acid; and
ethyl 5-(8-chloro-4-oxo-chromene-2-carboxamido)-1,3,4-thiadiazole-2-carboxylate; or a pharmaceutically acceptable salt thereof.

A further embodiment of the present invention is (viii) a compound of formula (I) according to (i), or a pharmaceutically acceptable salt thereof, wherein
R¹ is halogen;
R² is H;
R³ is H;
R⁴ is H;
R⁵ is H;
m is 1;
R⁶ is Cy²; wherein
　Cy² is isoindolinyl, 3,4-dihydro-1H-isoquinolinyl or 3,4-dihydro-2H-quinolinyl; wherein isoindolinyl, 3,4-dihydro-1H-isoquinolinyl and 3,4-dihydro-2H-quinolinyl are substituted by one substituent independently selected from halogen, $C_{1-6}$alkoxy and —NO₂.

A further embodiment of the present invention is (ix) a compound of formula (I) according to (i), or a pharmaceutically acceptable salt thereof, wherein
R¹ is Cl;
R² is H;
R³ is H;

R⁴ is H;
R⁵ is H;
m is 1;
R⁶ is Cy²; wherein
   Cy² is isoindolin-2-yl, 3,4-dihydro-1H-isoquinolin-2-yl or 3,4-dihydro-2H-quinolin-1-yl; wherein isoindolin-2-yl, 3,4-dihydro-1H-isoquinolin-2-yl and 3,4-dihydro-2H-quinolin-1-yl are substituted by one substituent independently selected from Cl, Br, methoxy and —NO₂.

In another embodiment (x) of the present invention, particular compounds of the present invention are selected from:
2-(5-bromoisoindoline-2-carbonyl)-8-chloro-chromen-4-one;
8-chloro-2-(6-methoxy-3,4-dihydro-1H-isoquinoline-2-carbonyl)chromen-4-one;
8-Chloro-2-(7-chloro-3,4-dihydro-1H-isoquinoline-2-carbonyl)chromen-4-one;
2-(6-bromo-1,2,3,4-tetrahydroisoquinoline-2-carbonyl)-8-chloro-chromen-4-one;
8-chloro-2-(8-chloro-3,4-dihydro-1H-isoquinoline-2-carbonyl)chromen-4-one;
2-(4-bromoisoindoline-2-carbonyl)-8-chloro-chromen-4-one; and
8-chloro-2-(7-nitro-3,4-dihydro-2H-quinoline-1-carbonyl)chromen-4-one;
or a pharmaceutically acceptable salt thereof.

A further embodiment of the present invention is (xi) a compound of formula (I) according to (i), or a pharmaceutically acceptable salt thereof, wherein
R¹ is halogen;
R² is H;
R³ is H or halogen;
R⁴ is H;
R⁵ is H or halogen;
m is 0;
R⁶ is -L-Cy¹, or Cy²; wherein
L is

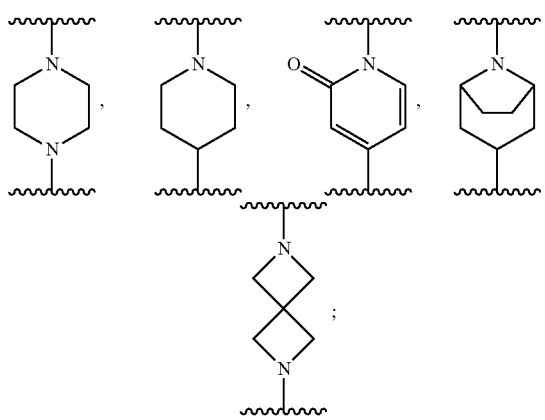

Cy¹ is phenyl, phenylC₁₋₆alkyl, phenylC₁₋₆alkoxy or phenylcarbonyl; wherein phenyl, phenylC₁₋₆alkyl, phenylC₁₋₆alkoxy and phenylcarbonyl are unsubstituted or substituted by one substituent independently selected from carboxy, C₁₋₆alkoxycarbonyl and (carboxyC₃₋₇cycloalkoxy)C₁₋₆alkoxy;
Cy² is isoindolinyl, 3,4-dihydro-1H-isoquinolinyl, piperidyl, 2,6-diazaspiro[3.3]heptanyl, 2-azaspiro[3.3] heptanyl or 8-azabicyclo[3.2.1]octanyl; wherein isoindolinyl, 3,4-dihydro-1H-isoquinolinyl, piperidyl, 2,6-diazaspiro[3.3]heptanyl, 2-azaspiro[3.3] heptanyl and 8-azabicyclo[3.2.1]octanyl are unsubstituted or substituted by one or two substituents independently selected from OH, C₁₋₆alkyl, C₁₋₆alkoxy, (carboxyC₁₋₆alkoxy)C₁₋₆alkoxy, (carboxyC₃₋₇cycloalkoxy)C₁₋₆alkoxy, C₁₋₆alkoxycarbonyl, (C₁₋₆alkoxycarbonylC₃₋₇cycloalkoxy)C₁₋₆alkoxy and oxo.

A further embodiment of the present invention is (xii) a compound of formula (I) according to (i), or a pharmaceutically acceptable salt thereof, wherein
R¹ is Cl;
R² is H;
R³ is H or F;
R⁴ is H;
R⁵ is H or I;
m is 0;
R⁶ is -L-Cy¹, or Cy²; wherein
L is

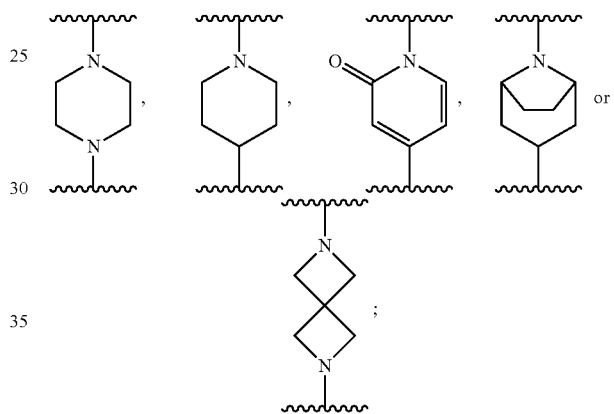

Cy¹ is phenyl, phenylmethyl, phenylmethoxy or phenylcarbonyl; wherein phenyl, phenylmethyl, phenylmethoxy and phenylcarbonyl are unsubstituted or substituted by one substituent independently selected from carboxy, methoxycarbonyl and (carboxycyclobutoxy)ethoxy;
Cy² is isoindolin-2-yl, 3,4-dihydro-1H-isoquinolin-2-yl, 1-piperidyl, 2,6-diazaspiro[3.3]heptan-2-yl, 2-azaspiro[3.3]heptan-2-yl or 8-azabicyclo[3.2.1]octan-8-yl; wherein isoindolin-2-yl, 3,4-dihydro-1H-isoquinolin-2-yl, 1-piperidyl, 2,6-diazaspiro[3.3]heptan-2-yl, 2-azaspiro[3.3]heptan-2-yl and 8-azabicyclo[3.2.1]octan-8-yl are unsubstituted or substituted by one or two substituents independently selected from OH, methyl, methoxy, (carboxymethoxy)ethoxy, (carboxycyclobutoxy)ethoxy, tert-butoxycarbonyl, (methoxycarbonylcyclobutoxy)ethoxy and oxo.

A further embodiment of the present invention is (xiii) a compound of formula (I) according to (i), or a pharmaceutically acceptable salt thereof, wherein R⁶ is Cy²; wherein Cy² is 3,4-dihydro-1H-isoquinolinyl; wherein 3,4-dihydro-1H-isoquinolinyl is substituted one time by (carboxyC₃₋₇cycloalkoxy)C₁₋₆alkoxy.

A further embodiment of the present invention is (xiv) a compound of formula (I) according to (i), or a pharmaceutically acceptable salt thereof, wherein Cy² is 3,4-dihydro- 1H-isoquinolin-2-yl; wherein 3,4-dihydro-1H-isoquinolin-2-yl is substituted one time by (carboxycyclobutoxy)ethoxy.

In another embodiment (xv) of the present invention, particular compounds of the present invention are selected from:
3-[2-[[2-(8-chloro-4-oxo-chromen-2-yl)-3,4-dihydro-1H-isoquinolin-6-yl]oxy]ethoxy]cyclobutanecarboxylic acid;
3-[2-[2-(8-chloro-4-oxo-chromen-2-yl)isoindolin-5-yl]oxy-ethoxy]cyclobutanecarboxylic acid;
3-((4-(8-chloro-4-oxo-chromen-2-yl)piperazin-1-yl)methyl) benzoic acid;
2-(2-((8-(8-chloro-4-oxo-chromen-2-yl)-8-azabicyclo [3.2.1]octan-3-yl)oxy)ethoxy)acetic acid;
3-[2-[[2-(8-chloro-4-oxo-chromen-2-yl)-1-methyl-3,4-di-hydro-1H-isoquinolin-6-yl]oxy]ethoxy]cyclobutanecar-boxylic acid;
methyl 3-(((8-(8-chloro-4-oxo-chromen-2-yl)-8-azabicyclo [3.2.1]octan-3-yl)oxy)methyl)benzoate;
2-(8-chloro-4-oxo-chromen-2-yl)-5-methoxyisoindolin-1-one;
2-(8-chloro-4-oxo-chromen-2-yl)-6-methoxy-3,4-dihy-droisoquinolin-1-one;
8-chloro-6-fluoro-2-(4-phenylpiperazin-1-yl)-chromen-4-one;
4-benzyloxy-1-(8-chloro-3-iodo-4-oxo-chromen-2-yl)pyri-din-2-one;
8-chloro-2-(6-hydroxy-2-azaspiro[3.3]heptan-2-yl) chromen-4-one;
8-chloro-6-fluoro-2-(4-phenylpiperidin-1-yl)-chromen-4-one;
3-(2-(4-(1-(8-chloro-6-fluoro-4-oxo-chromen-2-yl)piperi-din-4-yl)phenoxy)ethoxy)cyclobutane-1-carboxylic acid;
8-chloro-2-(3-hydroxy-8-azabicyclo[3.2.1]octan-8-yl)-chromen-4-one;
methyl 3-(4-(8-chloro-4-oxo-chromen-2-yl)piperazin-1-yl) benzoate;
methyl 3-(2-((2-(8-chloro-4-oxo-chromen-2-yl)-3-oxoisoin-dolin-5-yl)oxy)ethoxy)cyclobutanecarboxylate;
2-(8-chloro-4-oxo-chromen-2-yl)-6-methoxyisoindolin-1-one;
8-chloro-2-(6-hydroxy-1-methyl-3,4-dihydro-1H-isoquino-lin-2-yl)chromen-4-one;
3-(2-((2-(8-chloro-4-oxo-chromen-2-yl)-1-oxo-1,2,3,4-tet-rahydroisoquinolin-6-yl)oxy)ethoxy)cyclobutanecarbox-ylic acid;
4-(benzyloxy)-1-(8-chloro-4-oxo-chromen-2-yl)pyridin-2 (1H)-one;
8-chloro-2-(4-hydroxypiperidin-1-yl)-3-iodo-chromen-4-one;
tert-butyl 6-(8-chloro-4-oxo-chromen-2-yl)-2,6-diazaspiro [3.3]heptane-2-carboxylate;
methyl 3-[6-(8-chloro-4-oxo-chromen-2-yl)-2,6-diazaspiro [3.3]heptane-2-carbonyl]benzoate;
3-(2-((2-(8-chloro-4-oxo-chromen-2-yl)-1-oxoisoindolin-5-yl)oxy)ethoxy)cyclobutanecarboxylic acid; and
2-(8-chloro-4-oxo-chromen-2-yl)-7-methoxy-3,4-dihy-droisoquinolin-1-one;
or a pharmaceutically acceptable salt thereof.

A further embodiment of the present invention is (xvi) a compound of formula (I) according to (i), or a pharmaceutically acceptable salt thereof, wherein
$R^1$ is halogen;
$R^2$ is H;
$R^3$ is H;
$R^4$ is H;
$R^5$ is H or halogen;
m is 0;
$R^6$ is —N($R^7$)—$CH_2$—$Cy^1$; wherein
$R^7$ is H or $C_{1-6}$alkyl;
$Cy^1$ is phenyl; wherein phenyl is unsubstituted or substituted by one substituent independently selected from $C_{1-6}$alkoxy and (carboxy$C_{3-7}$cycloalkoxy) $C_{1-6}$alkoxy.

A further embodiment of the present invention is (xvii) a compound of formula (I) according to (i), or a pharmaceutically acceptable salt thereof, wherein
$R^1$ is Cl;
$R^2$ is H;
$R^3$ is H;
$R^4$ is H;
$R^5$ is H or I;
m is 0;
$R^6$ is —N($R^7$)—$CH_2$—$Cy^1$; wherein
$R^7$ is H or methyl;
$Cy^1$ is phenyl; wherein phenyl is unsubstituted or substituted by one substituent independently selected from methoxy and (carboxycyclobutoxy)ethoxy.

In another embodiment (xviii) of the present invention, particular compounds of the present invention are selected from:
8-chloro-3-iodo-2-((4-methoxybenzyl)amino)-chromen-4-one;
8-chloro-2-((4-methoxybenzyl)(methyl)amino)-chromen-4-one;
8-chloro-2-((4-methoxybenzyl)amino)-chromen-4-one;
3-(2-(4-(((8-chloro-4-oxo-chromen-2-yl)(methyl)amino) methyl)phenoxy)ethoxy)cyclobutanecarboxylic acid; and
3-(2-(4-(((8-chloro-4-oxo-chromen-2-yl)amino)methyl) phenoxy)ethoxy)cyclobutanecarboxylic acid;
or a pharmaceutically acceptable salt thereof.

Synthesis

The compounds of the present invention can be prepared by any conventional means. Suitable processes for synthesizing these compounds as well as their starting materials are provided in the schemes below and in the subsequent examples. All substituents, in particular, $R^1$ to $R^7$, m, L, $Cy^1$ and $Cy^2$ are defined above unless otherwise indicated. Furthermore, and unless explicitly otherwise stated, all reactions, reaction conditions, abbreviations and symbols have the meanings well known to a person of ordinary skill in the art.

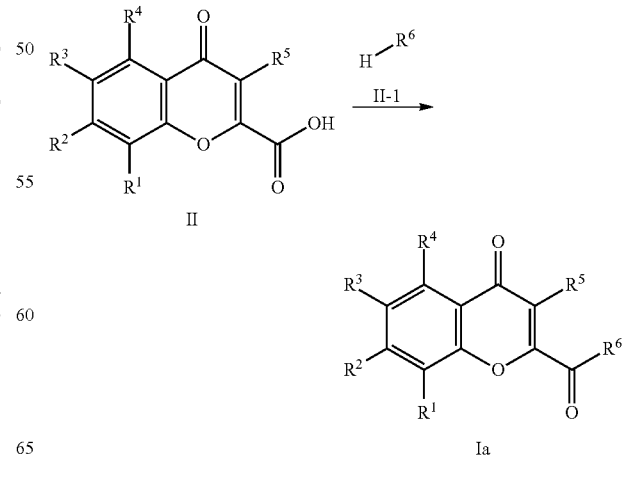

Scheme 1

Condensation of compound of formula II with amine II-1 in the presence of HATU and a suitable base, such as DIPEA or TEA, affords compound of formula Ia.

Scheme 2

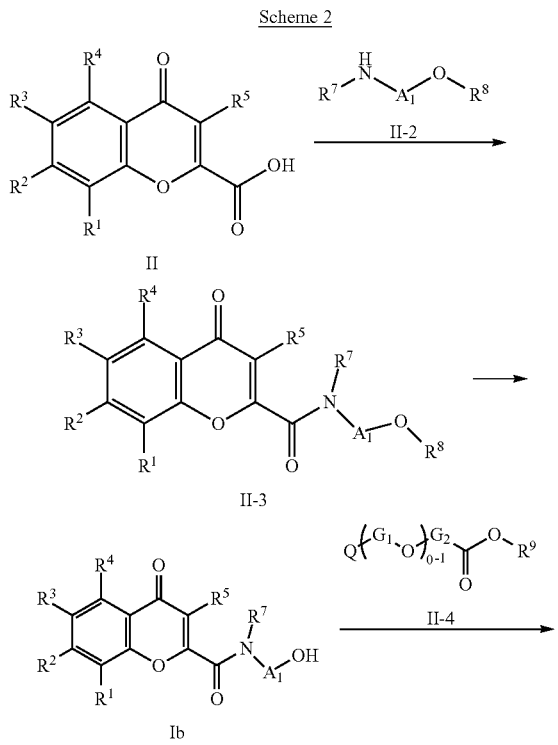

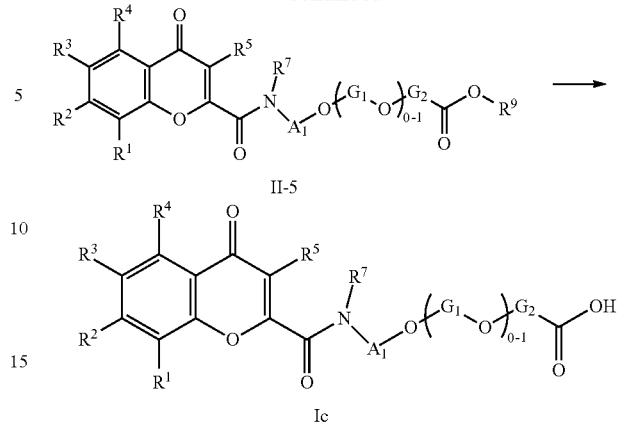

wherein $R^8$ is $C_{1-6}$alkyl; $R^9$ is $C_{1-6}$alkyl; $A_i$ is phenyl, wherein phenyl is unsubstituted or substituted by halogen, $C_{1-6}$alkyl or halo$C_{1-6}$alkyl; $G_1$ is $C_{1-6}$alkyl; $G_2$ is $C_{1-6}$alkyl, $C_{3-7}$cycloalkyl or phenyl$C_{1-6}$alkyl; Q is halogen, OTs, OTf or OMs.

Condensation of compound of formula II with aniline II-2 in the presence of HATU and a suitable base, such as DIPEA, affords compound of formula II-3. Dealkylation of compound of formula II-3 with a suitable Lewis acid, such as $BBr_3$, in a suitable solvent, such as DCM, affords compound of formula Ib. Substitution of compound of formula Ib with compound of formula II-4 in the presence of a suitable base, such as $K_2CO_3$, in a suitable solvent, such as DMF, affords compound of formula II-5. Hydrolysis of compound of formula II-5 with a suitable acid, such as hydrogen chloride or trifluoroacetic acid, affords compound of formula Ic.

Scheme 3

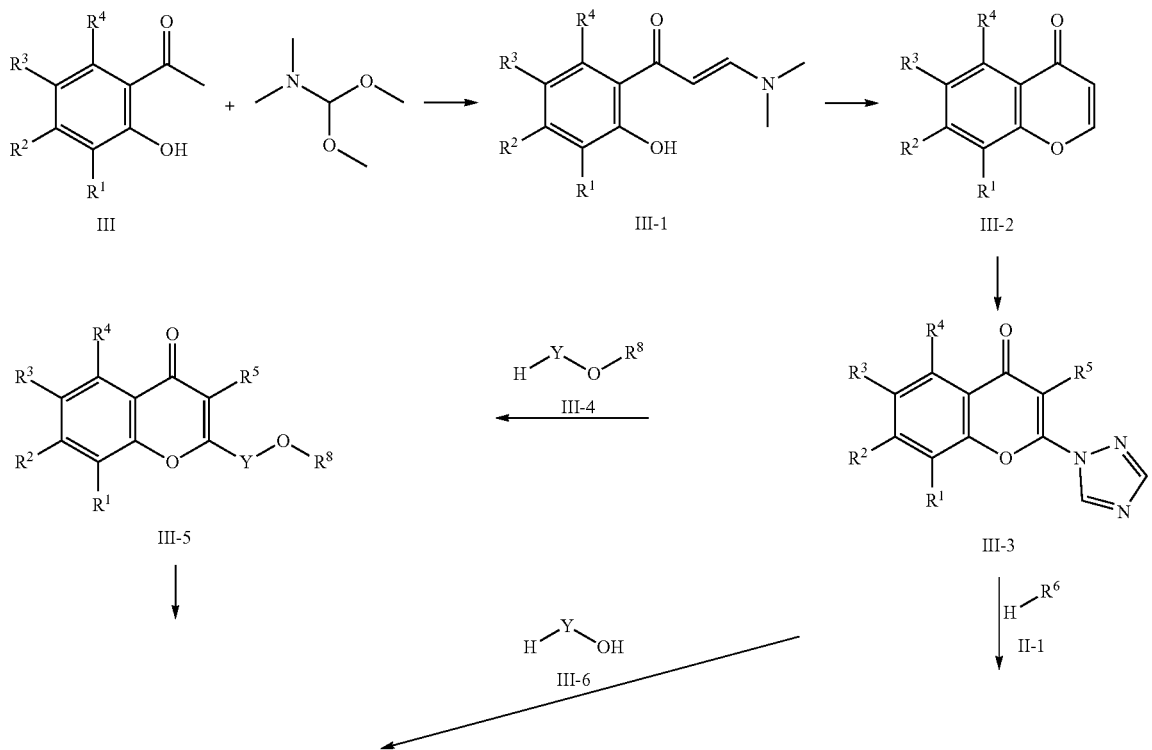

-continued

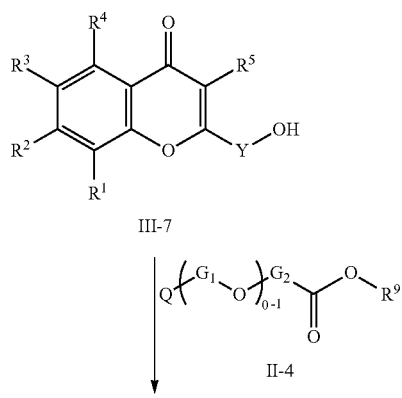

III-7

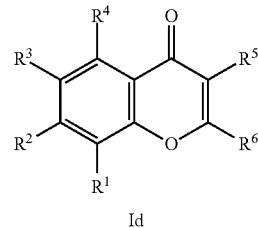

Id

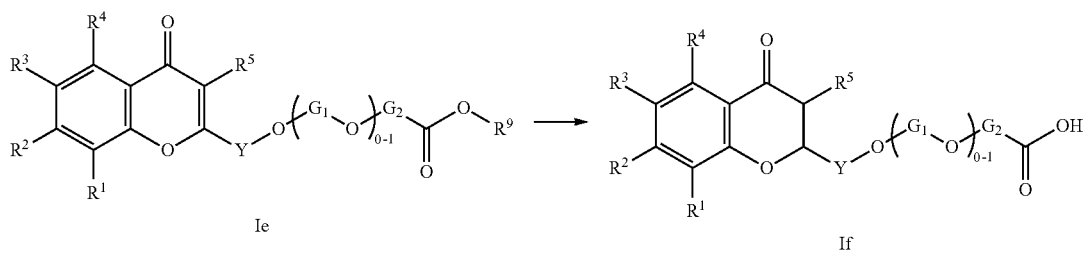

Ie → If wherein $R^8$ is $C_{1-6}$alkyl; $R^9$ is $C_{1-6}$alkyl; Y is isoindolinyl, 3,4-dihydro-1H-isoquinolinyl, phenylmethylamino or phenylmethyl(methyl)amino, wherein isoindolinyl and 3,4-dihydro-1H-isoquinolinyl are unsubstituted or substituted by one substituent independently selected from $C_{1-6}$alkyl and oxo; $G_1$ is $C_{1-6}$alkyl; $G_2$ is $C_{1-6}$alkyl, $C_{3-7}$cycloalkyl or phenyl$C_{1-6}$alkyl; Q is halogen, OTs, OTf or Oms.

Condensation of compound of formula III with DMF-DMA in a suitable solvent, such as toluene, affords compound of formula III-1. Cyclization of compound of formula III-1 in the presence of a suitable acid, such as HCl, in a suitable solvent, such as AcOH, affords compound of formula III-2. Substitution of compound of formula III-2 with 1H-1,2,4-triazole (halogen is added in case of need), in the presence of a suitable base, such as $K_2CO_3$, in a suitable solvent, such as DMF, affords compound of formula III-3. Substitution of compound of formula III-3 with amine II-1 in the presence of a suitable base, such as $K_2CO_3$, to give compound of formula Id.

The compound of formula If can be prepared by starting with substitution of compound of formula III-3 with compound of formula III-4 in the presence of a suitable base, such as $K_2CO_3$ or $Cs_2CO_3$, affords compound of formula III-5. Dealkylation of compound of formula III-5 with a suitable Lewis acid, such as $BBr_3$, in a suitable solvent, such as DCM, affords compound of formula III-7. Substitution of compound of formula III-7 with compound of formula II-4 in the presence of a suitable base, such as $K_2CO_3$, in a suitable solvent, such as DMF, affords compound of formula Ie. Hydrolysis of compound of formula Ie with a suitable acid or base, such as hydrogen chloride, trifluoroacetic acid or LiOH, affords compound of formula If. The compound of formula III-7 can also be prepared by substitution of compound of formula III-3 with compound of formula III-6 in the presence of a suitable base, such as $K_2CO_3$ or $Cs_2CO_3$, in a suitable solvent, such as DCM.

Scheme 4

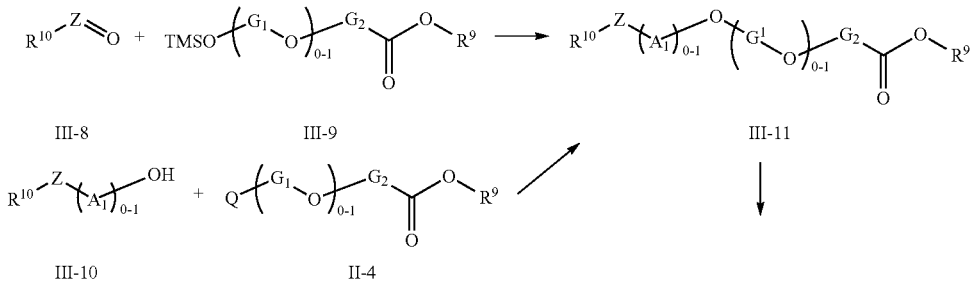

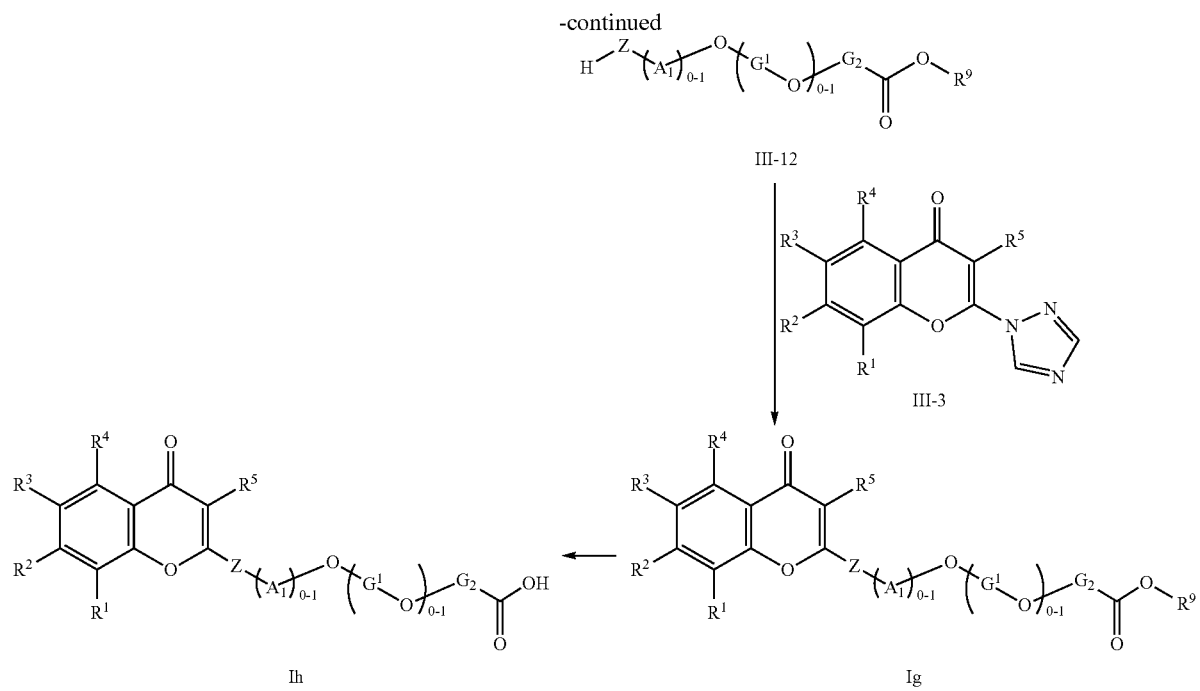

III-12

III-3

Ih

Ig wherein $R^8$ is $C_{1-6}$alkyl; $R^9$ is $C_{1-6}$alkyl; $R^{10}$ is $C_{1-6}$alkoxycarbonyl or phenyl$C_{1-6}$alkoxycarbonyl; Ai is phenyl, wherein phenyl is unsubstituted or substituted by halogen, $C_{1-6}$alkyl or halo$C_{1-6}$alkyl; Z is piperidyl or 8-azabicyclo [3.2.1]octanyl; $G_1$ is $C_{1-6}$alkyl; $G_2$ is $C_{1-6}$alkyl, $C_{3-7}$cycloalkyl or phenyl$C_{1-6}$alkyl; Q is halogen, OTs, OTf or OMs.

Substitution of compound of formula III-8 with compound of formula III-9 in the presence of trimethylsilyl trifluoromethanesulfonate and trimethylsilane, in a suitable solvent, such as DMF, affords compound of formula III-11. Hydrolysis of compound of formula III-11 in the presence of Pd/C, in a suitable solvent, such as EtOH, affords compound of formula III-12. Substitution of compound of formula III-3 with compound of formula III-12 in the presence of a suitable base, such as $K_2CO_3$, in a suitable solvent, such as DMF, affords compound of formula Ig. Hydrolysis of compound of formula Ig with a suitable acid or base, such as hydrogen chloride, trifluoroacetic acid or LiOH, affords compound of formula Ih. The compound of formula III-11 can be prepared by starting with substitution of compound of formula III-10 with compound of formula II-4 in the presence of a suitable base, such as $K_2CO_3$ or $Cs_2CO_3$, in a suitable solvent, such as DCM, to give compound of formula III-11.

Ii

III-14

Ij wherein $R^9$ is $C_{1-6}$alkyl; $R^{11}$ is ($C_{1-6}$alkoxycarbonyl)phenyl.

Substitution of compound of formula III-3 with compound of formula III-13 in the presence of a suitable base, such as $K_2CO_3$, affords compound of formula Ii. Deprotection of compound of formula Ii with a suitable acid, such as hydrogen chloride or trifluoroacetic acid, affords compound of formula III-14. Condensation of compound of formula III-14 with acid III-15 in the presence of HATU and a suitable base, such as DIPEA or TEA, affords compound of formula Ij.

Scheme 5

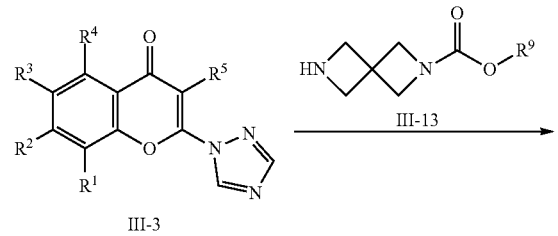

III-3

III-13

Scheme 6

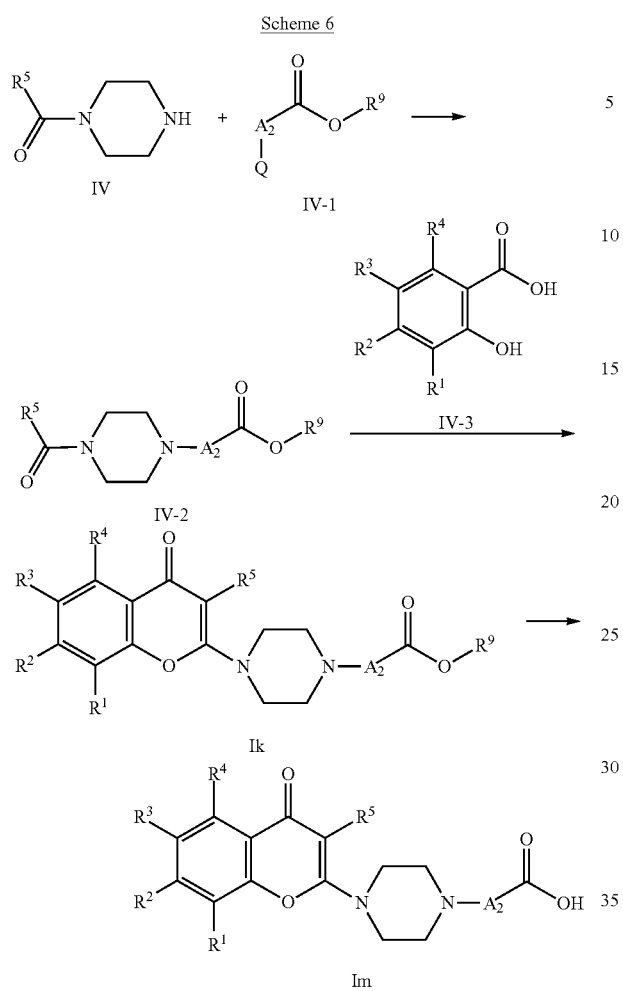

wherein R⁹ is $C_{1-6}$alkyl; $A_2$ is phenyl or phenyl$C_{1-6}$alkyl; Q is halogen, OTs, OTf or OMs.

Substitution of compound of formula IV with compound of formula IV-1 in the presence of a suitable base, such as $K_2CO_3$, in a suitable solvent, such as THF, affords compound of formula IV-2. Cyclization of compound of formula IV-2 with compound of formula IV-3 in the presence of $POCl_3$ and a suitable base, such as AcONa, affords compound of formula Ik.

Hydrolysis of compound of formula Ik with a suitable base, such as LiCl or LiOH, affords compound of formula Im.

This invention also relates to a process for the preparation of a compound of formula (I) comprising one of the following steps:

(a) Condensation of compound of formula (II),

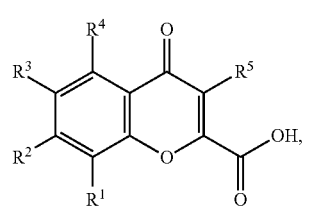

(II)

with amine (II-1), in the presence of HATU and a base;

(b) Dealkylation of compound of formula (II-3),

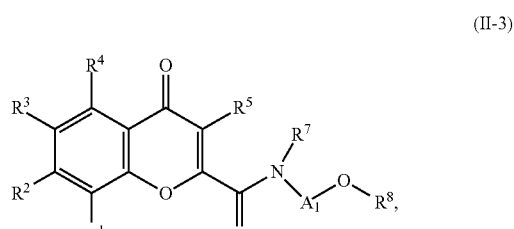

(II-3)

in the presence of a Lewis acid;

(c) Hydrolysis of compound of formula (II-5),

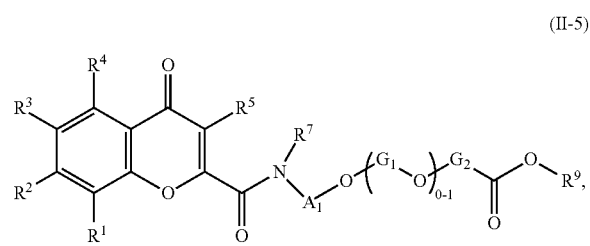

(II-5)

in the presence of an acid;

(d) Substitution of compound of formula (III-3),

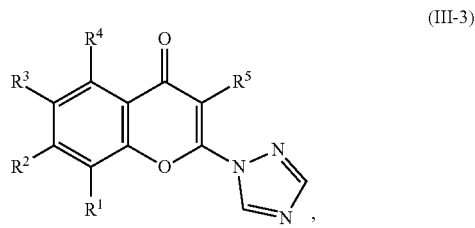

(III-3)

with amine (II-1), in the presence of a base;

(e) Substitution of compound of formula (III-7),

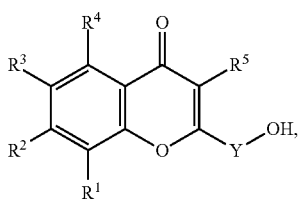

(III-7)

with compound of formula (II-4) in the presence of a base;

(f) Hydrolysis of compound of formula (Ie),

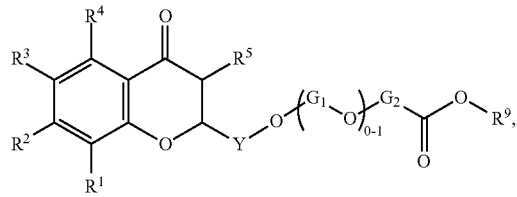

(Ie)

in the presence of an acid or a base;

(g) Substitution of compound of formula (III-3) with compound of formula (III-12) in the presence of a base;

(h) Hydrolysis of compound of formula (Ig),

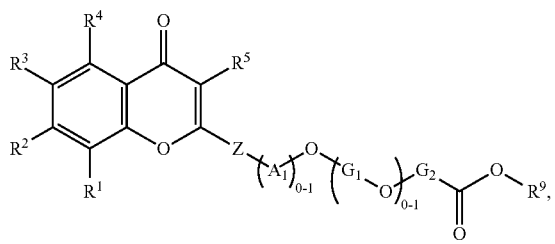

(Ig)

in the presence of an acid or a base;

(i) Substitution of compound of formula (III-3) with compound of formula (III-13) in the presence of a base;

(j) Condensation of compound of formula (III-14),

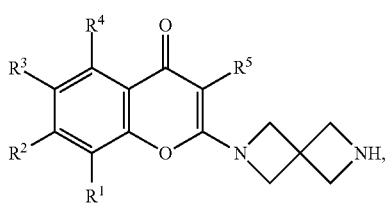

(III-14)

with acid (III-15) in the presence of HUTA and a base;

(k) Cyclization of compound of formula (IV-2),

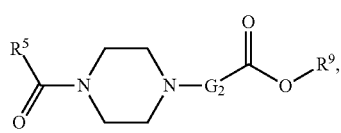

(IV-2)

with compound of formula (IV-3) in the presence of POCl$_3$ and AcONa;

(l) Hydrolysis of compound of formula (Ik),

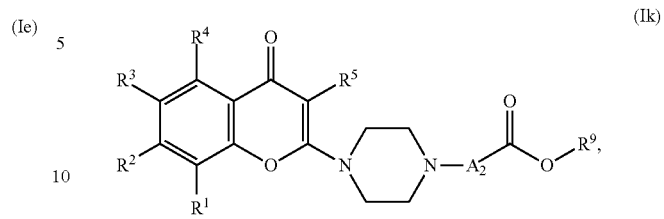

(Ik)

in the presence of a base;

wherein $R^1$, $R^2$, $R^3$, $R^4$, $R^5$, $R^6$, $R^7$ and L are defined above; $R^8$ is $C_{1-6}$alkyl; $R^9$ is $C_{1-6}$alkyl; Ai is phenyl, wherein phenyl is unsubstituted or substituted by halogen, $C_{1-6}$alkyl or halo$C_{1-6}$alkyl; $A_2$ is phenyl or phenyl$C_{1-6}$alkyl; Y is isoindolinyl, 3,4-dihydro-1H-isoquinolinyl, phenylmethylamino or phenylmethyl(methyl)amino, wherein isoindolinyl and 3,4-dihydro-1H-isoquinolinyl are unsubstituted or substituted by one substituent independently selected from $C_{1-6}$alkyl and oxo; Z is piperidyl or 8-azabicyclo[3.2.1]octanyl; $G_1$ is $C_{1-6}$alkyl; $G_2$ is $C_{1-6}$alkyl, $C_{3-7}$cycloalkyl or phenyl$C_{1-6}$alkyl; Q is halogen, OTs, OTf or OMs.

The base in step (a) or (j), can be for example DIPEA or TEA;

The Lewis acid in step (b), can be for example BBr$_3$;

The acid in step (c), (f) or (h), can be for example hydrogen chloride or trifluoroacetic acid;

The base in step (d), (e), (g) or (i), can be for example K$_2$CO$_3$;

The base in step (f) or (h), can be for example LiOH;

The base in step (l), can be for example LiCl or LiOH.

A compound of formula (I) when manufactured according to the above process is also an object of the invention.

The compound of this invention also shows good safety and PK profile.

Pharmaceutical Compositions and Administration

The invention also relates to a compound of formula (I) for use as therapeutically active substance. Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit cccDNA in HBV patients, consequently lead to the reduction of HBsAg and HBeAg (HBV e antigen) in serum. For example, such amount may be below the amount that is toxic to normal cells, or the mammal as a whole.

In one example, the pharmaceutically effective amount of the compound of the invention administered parenterally per dose will be in the range of about 0.1 to 100 mg/kg, alternatively about 0.1 to 50 mg/kg of patient body weight per day, with the typical initial range of compound used being 0.3 to 15 mg/kg/day. In another embodiment, oral unit dosage forms, such as tablets and capsules, preferably contain from about 25 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 to 500 mg of the compound of the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or a pharmaceutically acceptable salt thereof.

In a further embodiment includes a pharmaceutical composition comprising a compound of formula (I), or a pharmaceutically acceptable salt thereof, together with a pharmaceutically acceptable carrier or excipient.

Another embodiment includes a pharmaceutical composition comprising a compound of formula (I), or a pharmaceutically acceptable salt thereof for use in the treatment of HBV infection.

Indications and Methods of Treatment

The compounds of the invention can inhibit cccDNA and have anti-HBV activity. Accordingly, the compounds of the invention are useful for the treatment or prophylaxis of HBV infection.

The invention relates to the use of a compound of formula (I) for the inhibition of cccDNA.

The invention also relates to the use of a compound of formula (I) for the inhibition of HBeAg.

The invention further relates to the use of a compound of formula (I) for the inhibition of HBsAg.

The invention relates to the use of a compound of formula (I) for the inhibition of HBV DNA.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection, which method comprises administering an effective amount of a compound of Formula (I), or enantiomers, diastereomers, prodrugs or pharmaceutically acceptable salts thereof.

EXAMPLES

The invention will be more fully understood by reference to the following examples. They should not, however, be construed as limiting the scope of the invention.
Abbreviations used herein are as follows:
AcOH: acetic acid
ACN: acetonitrile
$BBr_3$: boron tribromide
DCM: dichloromethane
DIPEA: N,N-Diisopropylethylamine
DMAP: 4-dimethylaminopyridine
DME: dimethoxyethane
DMF: N, N-dimethylfonriamide
DMF-DMA: N,N-Dimethylformamide dimethyl acetal
$EC_{50}$: the molar concentration of an inhibitor, which produces 50% of the maximum possible response for that inhibitor.
FBS: fetal bovine serum
$H_2O_2$: hydrogen peroxide
HPLC: high performance liquid chromatography
HATU: 1-[Bis(dimethylamino)methylene]-1H-1,2,3-triazolo[4,5-b]pyridinium 3-oxid hexafluorophosphate
min: minute
MS (ESI): mass spectroscopy (electron spray ionization)

Ms: methylsulfonyl
NCS: N-chlorosuccinimide
NMP: N-methyl-2-pyrrolidone
obsd.: observed
PE: petroleum ether
PPA: polyphosphoric acid
PPh$_3$: triphenylphosphine
POCl$_3$: phosphorus oxychloride
Py: pyridine
Sphos: 2-dicyclohexylphosphino-2',6'-dimethoxybiphenyl
TEA: trimethylamine
Tf: trifluoromethanesulfonyl
TFA: trifluoroacetic acid
TFAA: trifluoroacetic anhydride
THF: Tetrahydrofuran
Ts: p-tolylsulfonyl
δ: chemical shift General Experimental Conditions Intermediates and final compounds were purified by flash chromatography using one of the following instruments: i) Biotage SP1 system and the Quad 12/25 Cartridge module, ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a Waters UPLC-SQD Mass. Standard LC/MS conditions were as follows (running time 3 mins):

Acidic condition: A: 0.1% formic acid and 1% acetonitrile in H$_2$O; B: 0.1% formic acid in acetonitrile;

Basic condition: A: 0.05% NH$_3$H$_2$O in H$_2$O; B: acetonitrile.

Mass spectra (MS): generally only ions which indicate the parent mass are reported, and unless otherwise stated the mass ion quoted is the positive mass ion (M+H)$^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Intermediate 1:
8-chloro-4-oxo-chromene-2-carboxylic Acid

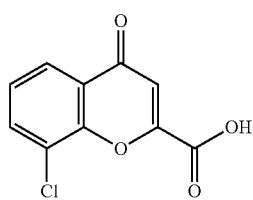

Int-1

To a solution of sodium hydride (1.41 g, 35.2 mmol) in EtOH (60 mL) was added 1-(3-chloro-2-hydroxyphenyl) ethanone (2 g, 11.7 mmol) and diethyl oxalate (3.77 g, 3.52 mL, 25.8 mmol) and then the resulting mixture was stirred at 80° C. for 12 hours. After the reaction was completed, the mixture was adjusted to pH~4 by addition of 4N HCl and then extracted with EtOAc (50 mL) three times. The combined organic layer was washed with brine, dried over anhydrous Na$_2$SO$_4$ and concentrated in vacuo. The residue (3.2 g, 11.7 mmol) was dissolved in the mixed solvent of AcOH (10 mL) and HCl (2 mL) and the mixture was then stirred at 80° C. for 5 hours. After the reaction was completed, the mixture was adjusted to pH~3 by addition of 4N HCl and then extracted with EtOAc (50 mL) three times. The combined organic layer was washed with brine, dried over anhydrous Na$_2$SO$_4$ and concentrated in vacuo to give 8-chloro-4-oxo-chromene-2-carboxylic acid (2 g, 76%) as a yellow solid which was used in next step directly without further purification. MS obsd. (ESI$^+$) [(M+H)$^+$]: 225.1

Intermediate 2:
6,8-dichloro-4-oxo-chromene-2-carboxylic Acid

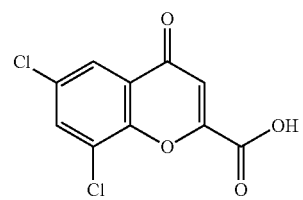

Int-2

To a solution of sodium ethoxide (16.6 g, 244 mmol) in EtOH (60 mL) was added 1-(3,5-dichloro-2-hydroxyphenyl) ethanone (10 g, 48.8 mmol) and diethyl oxalate (42.8 g, 40 mL, 293 mmol) was added and then the resulting mixture was stirred at 80° C. for 12 hours. After the reaction was completed, the mixture was adjusted to pH~4 by addition of 4N HCl and then extracted with EtOAc (50 mL) three times. The combined organic layer was washed with brine, dried over anhydrous Na$_2$SO$_4$ and concentrated in vacuo. The residue (15 g, 48.8 mmol) was dissolved in the mixed solvent of AcOH (100 mL) and HCl (20 mL) and the resulting mixture was then stirred at 80° C. for 5 hours. After the reaction was completed, the mixture was adjusted to pH~3 by addition of 4N HCl and then extracted with EtOAc (150 mL) three times. The combined organic layer was washed with brine, dried over anhydrous Na$_2$SO$_4$ and concentrated in vacuo to give 6,8-dichloro-4-oxo-chromene-2-carboxylic acid (6.3 g, 50%) as a yellow solid which was used in next step directly without further purification. MS obsd. (ESI$^+$) [(M+H)$^+$]: 259.1&261.1

Intermediate 3&4: 8-chloro-2-(1,2,4-triazol-1-yl)-chromen-4-one (Int-3) & 8-chloro-3-iodo-2-(1,2,4-triazol-1-yl)-chromen-4-one (Int-4)

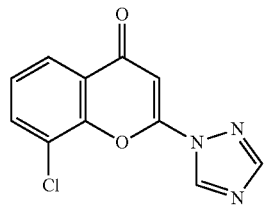

Int-3

Step 3: Preparation of 8-chloro-2-(1,2,4-triazol-1-yl)-chromen-4-one (Int-3) & 8-chloro-3-iodo-2-(1,2,4-triazol-1-yl)-chromen-4-one (Int-4)

Int-4

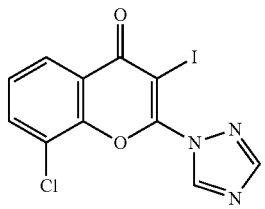

Step 1: Preparation of (E)-1-(3-chloro-2-hydroxyphenyl)-3-(dimethylamino)prop-2-en-1-one Int-a

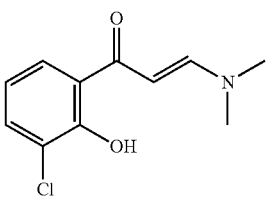

To a solution of 1-(3-chloro-2-hydroxyphenyl)ethanone (6 g, 35.2 mmol) in toluene (50 mL) was added DMF-DMA (8.38 g, 9.42 mL, 70.3 mmol) at room temperature and the resulting mixture was then stirred at 120° C. for 5 hours. After the reaction was completed, the mixture was concentrated in vacuo to give (E)-1-(3-chloro-2-hydroxyphenyl)-3-(dimethylamino)prop-2-en-1-one (8 g, 101%) as a brown solid, which was used in next step directly without further purification. MS obsd. (ESI⁺) [(M+H)⁺]: 226.1

Step 2: Preparation of 8-chloro-chromen-4-one

Int-b

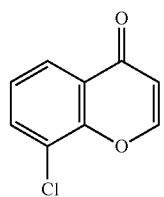

To a solution of (E)-1-(3-chloro-2-hydroxyphenyl)-3-(dimethylamino)prop-2-en-1-one (2.1 g, 9.31 mmol) in AcOH (20 mL) was added HCl (5 mL) at room temperature and the resulting mixture was then stirred at 80° C. for 5 hours. After the reaction was completed, the mixture was concentrated in vacuo. The residue was then extracted with EtOAc (150 mL) three times. The combined organic layer was washed with brine, dried over anhydrous Na₂SO₄ and concentrated in vacuo to give 8-chloro-chromen-4-one (1.4 g, 83.3%) as a yellow foam, which was used in next step directly without further purification. MS obsd. (ESI⁺) [(M+H)⁺]: 181.1

Int-3

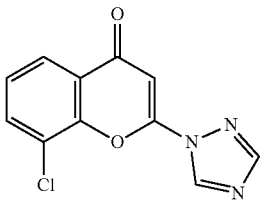

Int-4

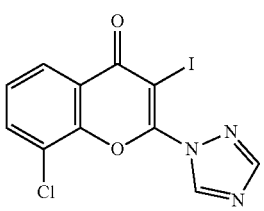

To a solution of 8-chloro-chromen-4-one (1.5 g, 8.31 mmol), 1H-1,2,4-triazole (1.15 g, 16.6 mmol) and potassium carbonate (5.74 g, 41.5 mmol) in DML (40 mL) was added I₂ (3.16 g, 12.5 mmol) at room temperature and the resulting mixture was then stirred at 80° C. for 3 hours.

After the reaction was completed, the mixture was quenched with sodium thiosulphate solution and extracted with EtOAc (50 mL) three times. The combined organic layer was washed with brine, dried over anhydrous Na₂SO₄ and concentrated in vacuo to give 8-chloro-2-(1,2,4-triazol-1-yl)-chromen-4-one (1.6 g, 77.8%) (Int-3) as a yellow foam, MS obsd. (ESI⁺) [(M+H)⁺]: 248.1 and 8-chloro-3-iodo-2-(1,2,4-triazol-1-yl)-chromen-4-one (800 mg, 25%) (Int-4) as a yellow foam, MS obsd. (ESI⁺) [(M+H)⁺]: 374.1.

Intermediate 5:
1-methyl-1,2,3,4-tetrahydroisoquinolin-6-ol;
Hydrobromide

Int-5

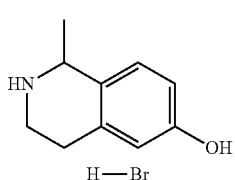

Step 1: Preparation of N-[2-(3-methoxyphenyl)ethyl]acetamide

Int-5a

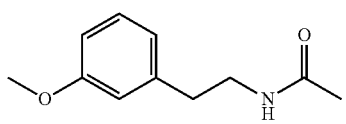

To a solution of acetyl chloride (2.62 g, 2.38 mL, 33.3 mmol) in DCM (20 mL) was added slowly a solution of 2-(3-methoxyphenyl)ethanamine (5.04 g, 33.3 mmol) and Et₃N (5.06 g, 6.97 mL, 50 mmol) in DCM (50 mL) at 0° C. and then the resulting mixture was stirred at room temperature for 10 hours. After the reaction was completed, the mixture was washed with 1N HCl (100 mL), saturated NaHCO₃ solution, brine, dried over Na₂SO₄ and concentrated in vacuo to give N-[2-(3-methoxyphenyl)ethyl]acetamide (6.2 g, 96%).

Step 2: Preparation of 6-methoxy-1-methyl-3,4-dihydroisoquinoline

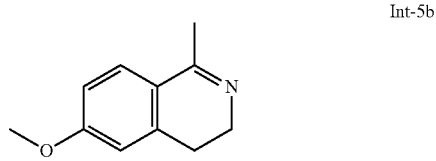

Int-5b

A solution of N-[2-(3-methoxyphenyl)ethyl]acetamide (2.2 g, 11.4 mmol) and POCl₃ (8.73 g, 5.31 mL, 56.9 mmol) in toluene (30 mL) was stirred at 120° C. for 5 hours. After the reaction was completed, the mixture was poured into H₂O (100 mL). The resulting mixture was adjusted to pH~10 by addition of 12 N NaOH and then extracted with EtOAc (50 mL) three times. The combined organic layer was washed with brine, dried over anhydrous Na₂SO₄ and concentrated in vacuo to give 6-methoxy-1-methyl-3,4-dihydroisoquinoline (1.9 g, 95%).

Step 3: Preparation of 6-methoxy-1-methyl-1,2,3,4-tetrahydroisoquinoline

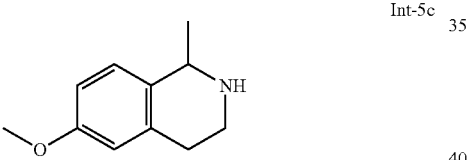

Int-5c

To a solution of 6-methoxy-1-methyl-3,4-dihydroisoquinoline (2.1 g, 12 mmol) in MeOH (20 mL) was added NaBH₄ (907 mg, 24 mmol) at 0° C. and the resulting mixture was stirred at room temperature overnight. The mixture was adjusted to pH~3 by addition of 1N HCl and concentrated in vacuo. The residue was adjusted to pH~8 by 1N NaOH and extracted with DCM (20 mL) three times. The combined organic layer was washed with brine, dried over anhydrous Na₂SO₄ and concentrated in vacuo to give 6-methoxy-1-methyl-1,2,3,4-tetrahydroisoquinoline (2.0 g, 94%).

Step 4: Preparation of 1-methyl-1,2,3,4-tetrahydroisoquinolin-6-ol; Hydrobromide

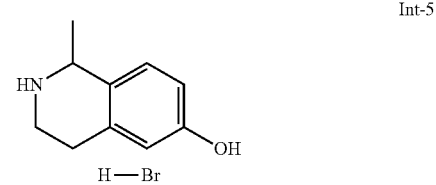

Int-5

A solution of 6-methoxy-1-methyl-1,2,3,4-tetrahydroisoquinoline (1.2 g, 6.77 mmol) in HBr (11.7 g, 47% wt. in H₂O, 67.7 mmol) was stirred at 100° C. overnight. After the reaction was completed, the mixture was concentrated in vacuo and triturated with EtOAc. The mixture was filtered and the solid was collected and dried in vacuo to give 1-methyl-1,2,3,4-tetrahydroisoquinolin-6-ol; hydrobromide (1.1 g, 99%) as a brown solid. MS obsd. (ESI⁺) [(M+H)⁺]: 164.

Intermediate 6: 8-chloro-6-fluoro-2-(1,2,4-triazol-1-yl)-chromen-4-one

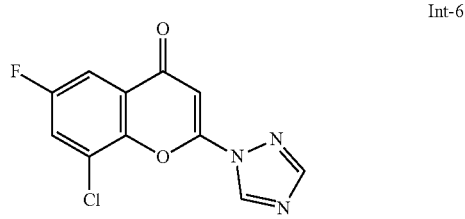 [SMILES: O=c1cc(-n2cncn2)oc2c(Cl)cc(F)cc12]

Int-6

Step 1: Preparation of (E)-1-(3-chloro-5-fluoro-2-hydroxyphenyl)-3-(dimethylamino)prop-2-en-1-one

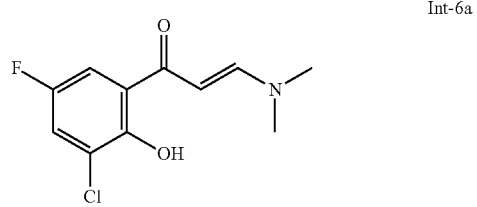 [SMILES: CN(C)/C=C/C(=O)c1cc(F)cc(Cl)c1O]

Int-6a

To a solution of 1-(3-chloro-5-fluoro-2-hydroxyphenyl)ethan-1-one (8 g, 42.42 mmol) in toluene (50 mL) was added DMF-DMA (8.38 g, 9.42 mL, 70.3 mmol) at room temperature and the resulting mixture was then stirred at 120° C. for 5 hours. After the reaction was completed, the mixture was concentrated in vacuo to give the crude (E)-1-(3-chloro-5-fluoro-2-hydroxyphenyl)-3-(dimethylamino)prop-2-en-1-one (5 g, 48.4%) as a brown solid, which was used in next step directly without further purification. MS obsd. (ESI⁺) [(M+H)⁺]: 244.1

Step 2: Preparation of 8-chloro-6-fluoro-chromen-4-one

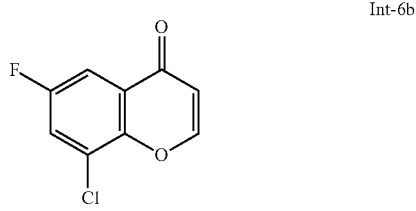 [SMILES: O=c1ccoc2c(Cl)cc(F)cc12]

Int-6b

To a solution of (E)-1-(3-chloro-5-fluoro-2-hydroxyphenyl)-3-(dimethylamino)prop-2-en-1-one (5 g, 20.52 mmol) in AcOH (20 mL) was added HCl (5 mL) at room temperature and the resulting mixture was then stirred at 80° C. for 5 hours. After the reaction was completed, the mixture was concentrated in vacuo and the residue was then extracted with EtOAc (150 mL) three times. The combined organic layer was washed with brine, dried over anhydrous Na$_2$SO$_4$ and concentrated in vacuo to give 8-chloro-6-fluoro-chromen-4-one (3.6 g, 88.3%) as a yellow foam, which was used in next step directly without further purification. MS obsd. (ESI$^+$) [(M+H)$^+$]: 199.1

Step 3: Preparation of 8-chloro-6-fluoro-2-(1,2,4-triazol-1-yl)-chromen-4-one

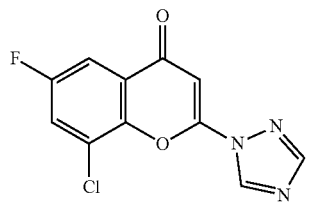

Int-6

To a solution of 8-chloro-6-fluoro-chromen-4-one (1.8 g, 9.06 mmol), 1H-1,2,4-triazole (1.15 g, 16.6 mmol) and potassium carbonate (6.8 g, 49.5 mmol) in DMF (40 mL) was added diiodine (3.16 g, 12.5 mmol) at room temperature and the resulting mixture was then stirred at 80° C. for 3 hours. After the reaction was completed, the mixture was quenched with sodium thiosulphate solution and extracted with EtOAc (50 mL) three times. The combined organic layer was washed with brine, dried over anhydrous Na$_2$SO$_4$ and concentrated in vacuo to give 8-chloro-6-fluoro-2-(1,2,4-triazol-1-yl)-chromen-4-one (600 mg, 25.28%) as a yellow foam, which was used in next step directly without further purification. MS obsd. (ESI$^+$) [(M+H)$^+$]: 266.1.

Intermediate 7: methyl 3-(2-hydroxyethoxy)cyclobutanecarboxylate

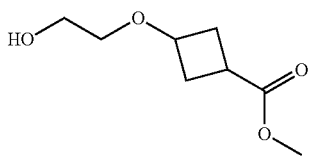

Int-7

Step 1: Preparation of 2-benzyloxyethoxy(trimethyl)silane

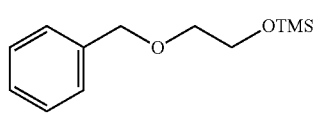

Int-7a

To a solution of 2-benzyloxyethanol (20.0 g, 131.4 mmol) and TEA (20.0 g, 197.1 mmol) in DCM (200 mL) was added trimethylsilyl chloride (17.1 g, 157.7 mmol) at 0° C. and the resulting mixture was then stirred at 25° C. for 16 hours. After the reaction was completed, the mixture was concentrated in vacuo and the residue was purified by column chromatography on silica gel (elution with PE:EtOAc=50:1 to 10:1) to give the 2-benzyloxyethoxy(trimethyl)silane (25.0 g, 84.9%) as a colorless oil.

Step 2: Preparation of methyl 3-(2-benzyloxyethoxy)cyclobutanecarboxylate

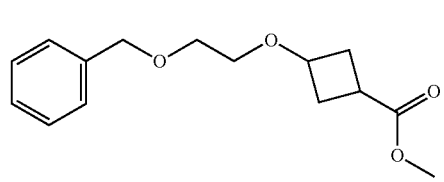

Int-7b

To a solution of 2-benzyloxyethoxy(trimethyl)silane (25.0 g, 111.4 mmol) and methyl 3-oxocyclobutanecarboxylate (15.0 g, 117.0 mmol) in DCM (200 mL) was added slowly trimethylsilyl trifluoromethanesulfonate (12.4 g, 55.7 mmol) at −78° C. After that, the mixture was stirred at −78° C. for 1 hour and then to the resulting mixture was added triethylsilane (14.25 g, 122.57 mmol). The resulting mixture was then warmed to room temperature and stirred at room temperature for 1 hour. After the reaction was completed, the mixture was washed with saturated NH$_4$Cl solution, brine, dried over anhydrous sodium sulfate, and concentrated in vacuo. The residue was purified by column chromatography on silica gel (elution with PE/EtOAc=100:1-50:1) to give methyl 3-(2-benzyloxyethoxy)cyclobutanecarboxylate (28 g, 95.1%) as a colorless oil. MS obsd. (ESI$^+$) [(M+H)$^+$]: 265.1.

Step 3: Preparation of methyl 3-(2-hydroxyethoxy)cyclobutanecarboxylate

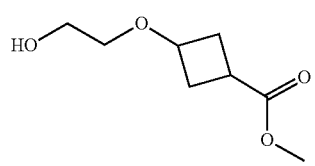

Int-7

To a solution of methyl 3-(2-benzyloxyethoxy)cyclobutanecarboxylate (28.0 g, 105.9 mmol) in MeOH (300.0 mL) was added Pd(OH)$_2$ (wet) (1.48 g, 10.6 mmol) at room temperature and the resulting mixture was then hydrogenated under H$_2$ atmosphere at room temperature overnight. After the reaction was completed, the mixture was filtered through silica gel pad and the filtrate was concentrated in vacuo to give methyl 3-(2-hydroxyethoxy)cyclobutanecarboxylate (18 g, 97.6%) as a colorless oil.

Intermediate 8: methyl 3-[2-(p-tolylsulfonyloxy)ethoxy]cyclobutanecarboxylate

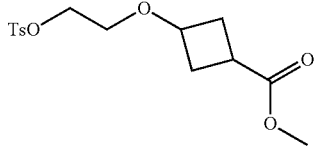

Int-8

To a solution of methyl 3-(2-hydroxyethoxy)cyclobutanecarboxylate (Int-7, 5 g, 28.7 mmol) and DMAP (5.26 g, 43.1 mmol) in DCM (80 mL) was added 4-methylbenzene-1-sulfonyl chloride (6.02 g, 31.6 mmol) at room temperature and the resulting mixture was then stirred at room temperature overnight. After the reaction was completed, the mixture was washed with 1N HCl (25 mL), water (15 mL), saturated NaHCO$_3$ solution, brine and concentrated in vacuo to give methyl 3-[2-(p-tolylsulfonyloxy)ethoxy]cyclobutanecarboxylate (8.1 g, 85.6%) as a colorless oil, which was used in next step directly without further purification. MS obsd. (ESI$^+$) [(M+H)$^+$]: 329.2.

Intermediate 9: 1,2,3,4-tetrahydroisoquinolin-6-ol; Hydrobromide

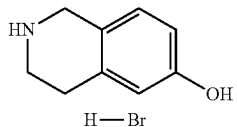

Int-9

A solution of 6-methoxy-1,2,3,4-tetrahydroisoquinoline (200 mg, 1.23 mmol) in HBr (3.16 g, 47% wt. in H$_2$O, 18.4 mmol) was stirred at 100° C. overnight. After the reaction was completed, the mixture was concentrated in vacuo and triturated with EtOAc. The mixture was filtered and the solid was collected and dried in vacuo to give 1,2,3,4-tetrahydroisoquinolin-6-ol; hydrobromide (170 mg, 93%) as a brown solid. MS obsd. (ESI$^+$) [(M+H)$^+$]: 150.

Intermediate 10: isoindolin-5-ol; Hydrobromide

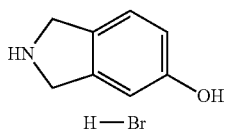

Int-10

A solution of 5-methoxyisoindoline (800 mg, 5.36 mmol) in HBr (13.8 g, 47% wt. in H$_2$O, 80.4 mmol) was stirred at 100° C. overnight. After the reaction was completed, the mixture was concentrated in vacuo and triturated with EtOAc. The mixture was filtered and the solid was collected and dried in vacuo to give isoindolin-5-ol; hydrobromide (1.1 g, 95%) as a brown solid. MS obsd. (ESI$^+$) [(M+H)$^+$]: 136.

Example 1

3-(2-(4-(8-chloro-4-oxo-chromene-2-carboxamido)-3-fluorophenoxy)ethoxy)cyclobutanecarboxylic Acid

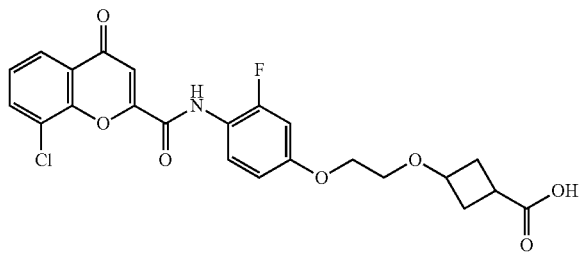

1

Step 1: Preparation of 8-chloro-N-(2-fluoro-4-methoxyphenyl)-4-oxo-chromene-2-carboxamide

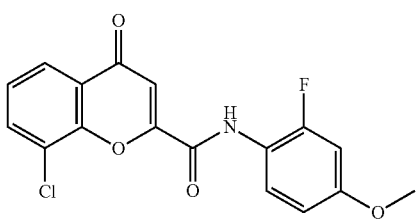

1a

To a solution of 8-chloro-4-oxo-chromene-2-carboxylic acid (Int-1, 300 mg, 1.34 mmol) in DCM (20 mL) was added 2-fluoro-4-methoxyaniline (283 mg, 2 mmol), DIPEA (276 mg, 2.14 mmol) and HATU (762 mg, 2 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by silica gel flash chromatography (elution with PE/EtOAc=10:1-1:2) to give 8-chloro-N-(2-fluoro-4-methoxyphenyl)-4-oxo-chromene-2-carboxamide (200 mg, 43.1%) as a yellow solid. $^1$H NMR (DMSO-d$_6$, 400 MHz): δ ppm 10.13-10.23 (m, 1H), 7.99-8.12 (m, 2H), 7.51-7.66 (m, 2H), 6.96-7.07 (m, 2H), 6.82-6.90 (m, 1H), 3.84 (s, 3H). MS obsd. (ESI$^+$) [(M+H)$^+$]: 348.1.

Step 2: Preparation of 8-chloro-N-(2-fluoro-4-hydroxyphenyl)-4-oxo-chromene-2-carboxamide

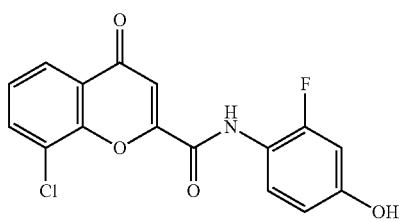

1b

To a solution of 8-chloro-N-(2-fluoro-4-methoxyphenyl)-4-oxo-chromene-2-carboxamide (230 mg, 661 μmol) in DCM (10 mL) was added BBr₃ (1 M solution in DCM, 5 mL, 5 mmol) at room temperature and the resulting mixture was stirred at room temperature overnight. After the reaction was completed, the mixture was concentrated in vacuo and the residue was suspended in saturated NH₄Cl solution (30 mL). The solid was collected by filtration and dried in vacuo to give 8-chloro-N-(2-fluoro-4-hydroxyphenyl)-4-oxo-chromene-2-carboxamide (200 mg, 90.6%) as a yellow solid, which was used in the next step directly without further purification. MS obsd. (ESI⁺)[(M+H)⁺]: 334.1.

Step 3: Preparation of methyl 3-(2-(4-(8-chloro-4-oxo-chromene-2-carboxamido)-3-fluorophenoxy)ethoxy)cyclobutanecarboxylate

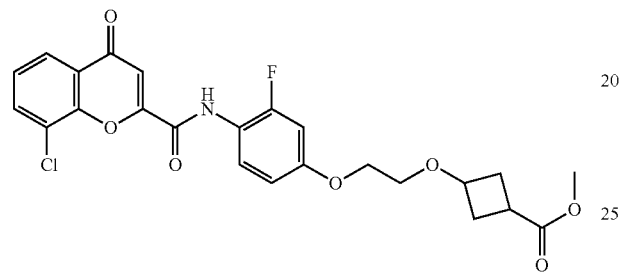

1c

To a solution of 8-chloro-N-(2-fluoro-4-hydroxyphenyl)-4-oxo-chromene-2-carboxamide (250 mg, 749 μmol) and methyl 3-[2-(p-tolylsulfonyloxy)ethoxy]cyclobutanecarboxylate (Int-8, 295 mg, 899 μmol) in DMF (5 mL) was added K₂CO₃ (207 mg, 1.5 mmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na₂SO₄ and concentrated in vacuo to give methyl 3-(2-(4-(8-chloro-4-oxo-chromene-2-carboxamido)-3-fluorophenoxy)ethoxy)cyclobutanecarboxylate (150 mg, 40.9%) as a yellow oil, which was used in next step directly without further purification. MS obsd. (ESI⁺) [(M+H)⁺]: 490.1.

Step 4: Preparation of 3-(2-(4-(8-chloro-4-oxo-chromene-2-carboxamido)-3-fluorophenoxy)ethoxy)cyclobutanecarboxylic Acid

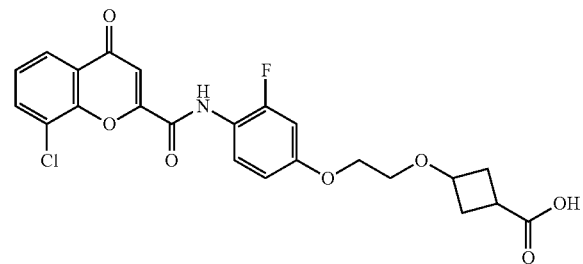

1

To a solution of methyl 3-(2-(4-(8-chloro-4-oxo-chromene-2-carboxamido)-3-fluorophenoxy)ethoxy)cyclobutanecarboxylate (150 mg, 306 μmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 3-(2-(4-(8-chloro-4-oxo-chromene-2-carboxamido)-3-fluorophenoxy)ethoxy)cyclobutanecarboxylic acid (10 mg, 6.86%) as a light yellow foam. ¹H NMR (400 MHz, DMSO-d₆) δ 12.13-12.19 (m, 1H), 10.11-10.25 (m, 1H), 7.97-8.13 (m, 2H), 7.50-7.66 (m, 2H), 7.02-7.08 (m, 1H), 6.99-7.02 (m, 1H), 6.82-6.92 (m, 1H), 4.13-4.21 (m, 1H), 4.07-4.14 (m, 2H), 3.58-3.68 (m, 2H), 2.87-2.97 (m, 1H), 2.33-2.47 (m, 2H), 2.10-2.23 (m, 1H), 1.92-2.05 (m, 1H). MS obsd. (ESI⁺) [(M+H)⁺]: 476.1.

Example 2

3-(2-(4-(8-chloro-4-oxo-chromene-2-carboxamido)-3-methylphenoxy)ethoxy)cyclobutanecarboxylic Acid

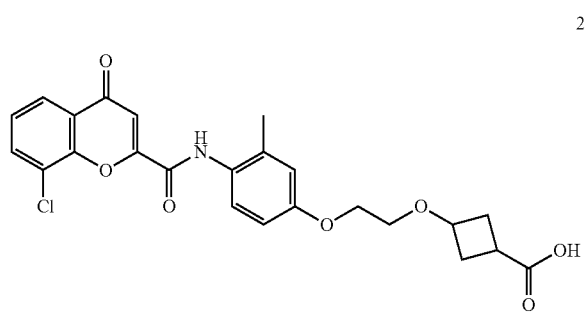 [SMILES: Cc1cc(OCCOC2CC(C(=O)O)C2)ccc1NC(=O)c1cc(=O)c2cccc(Cl)c2o1]

2

Step 1: Preparation of 8-chloro-N-(4-methoxy-2-methylphenyl)-4-oxo-chromene-2-carboxamide

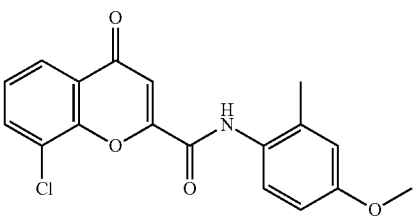

2a

To a solution of 8-chloro-4-oxo-chromene-2-carboxylic acid (Int-1, 300 mg, 1.34 mmol) in DCM (20 mL) was added 4-methoxy-2-methylaniline (275 mg, 2 mmol), DIPEA (276 mg, 2.14 mmol) and HATU (762 mg, 2 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na₂SO₄ and concentrated in vacuo. The residue was purified by silica gel flash chromatography (elution with PE/EtOAc=10:1-1:2) to give 8-chloro-N-(4-methoxy-2-methylphenyl)-4-oxo-chromene-2-carboxamide (300 mg, 65.3%) as a yellow solid. MS obsd. (ESI⁺) [(M+H)⁺]: 344.1.

Step 2: Preparation of 8-chloro-N-(4-hydroxy-2-methylphenyl)-4-oxo-chromene-2-carboxamide

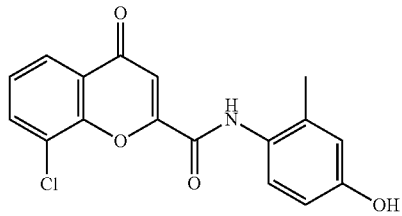

2b

To a solution of 8-chloro-N-(4-methoxy-2-methylphenyl)-4-oxo-chromene-2-carboxamide (400 mg, 1.16 mmol) in DCM (20 mL) was added BBr$_3$ (1 M solution in DCM, 8 mL, 8 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 8-chloro-N-(4-hydroxy-2-methylphenyl)-4-oxo-chromene-2-carboxamide (340 mg, 88.6%) as a yellow solid, which was used in the next step directly without further purification. MS obsd. (ESI$^+$) [(M+H)$^+$]: 330.1.

Step 3: Preparation of methyl 3-(2-(4-(8-chloro-4-oxo-chromene-2-carboxamido)-3-methylphenoxy)ethoxy)cyclobutanecarboxylate

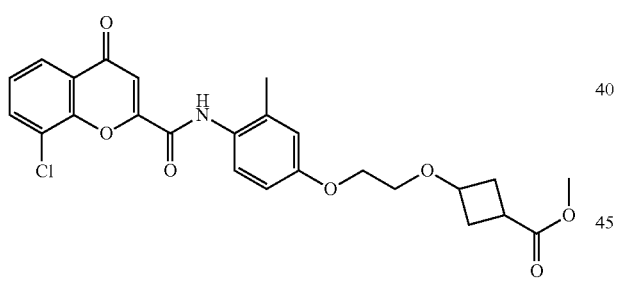

2c

To a solution of 8-chloro-N-(4-hydroxy-2-methylphenyl)-4-oxo-chromene-2-carboxamide (170 mg, 516 μmol) and methyl 3-[2-(p-tolylsulfonyloxy)ethoxy]cyclobutanecarboxylate (Int-8, 203 mg, 619 μmol) in DMF (5 mL) was added K$_2$CO$_3$ (143 mg, 1.03 mmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give methyl 3-(2-(4-(8-chloro-4-oxo-chromene-2-carboxamido)-3-methylphenoxy)ethoxy)cyclobutanecarboxylate (120 mg, 47.9%) as a yellow oil, which was used in next step directly without further purification. MS obsd. (ESI$^+$) [(M+H)$^+$]: 486.1.

Step 4: Preparation of 3-(2-(4-(8-chloro-4-oxo-chromene-2-carboxamido)-3-methylphenoxy)ethoxy)cyclobutanecarboxylic Acid

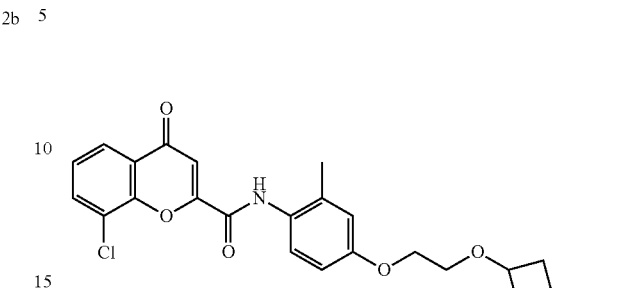

2

To a solution of methyl 3-(2-(4-(8-chloro-4-oxo-chromene-2-carboxamido)-3-methylphenoxy)ethoxy)cyclobutanecarboxylate (140 mg, 288 μmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 3-(2-(4-(8-chloro-4-oxo-chromene-2-carboxamido)-3-methylphenoxy)ethoxy)cyclobutanecarboxylic acid (27 mg, 19.9%) as a white foam. $^1$H NMR (400 MHz, DMSO-d$_6$) δ 12.15-12.22 (m, 1H), 9.87-9.95 (m, 1H), 7.98-8.13 (m, 2H), 7.50-7.63 (m, 1H), 7.40-7.48 (m, 1H), 7.01-7.06 (m, 1H), 6.89-6.96 (m, 1H), 6.80-6.89 (m, 1H), 4.12-4.21 (m, 1H), 4.03-4.10 (m, 2H), 3.55-3.68 (m, 2H), 2.83-2.97 (m, 1H), 2.35-2.43 (m, 2H), 2.25-2.29 (m, 3H), 1.92-2.20 (m, 2H). MS obsd. (ESI$^+$) [(M+H)$^+$]: 472.1.

Example 3

6-chloro-N-(4-chloro-2-methylphenyl)-3-methyl-4-oxo-chromene-2-carboxamide

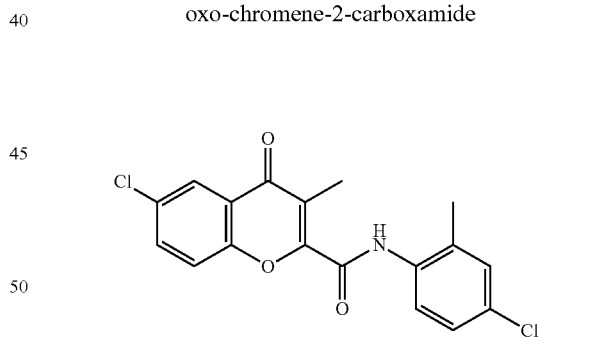

3

To a solution of 6-chloro-3-methyl-4-oxo-chromene-2-carboxylic acid (100 mg, 419 μmol) in DCM (20 mL) was added 4-chloro-2-methylaniline (119 mg, 0.84 mmol), DIPEA (162 mg, 1.26 mmol) and HATU (239 mg, 629 μmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 6-chloro-N-(4-chloro-2-methylphenyl)-3-methyl-4-oxo-chromene-2-carboxamide (60 mg, 39.5%) as a white foam. $^1$H NMR (400 MHz, DMSO-d$_6$) δ 10.38-10.59 (m, 1H), 8.00-8.07 (m, 1H), 7.88-7.99 (m, 1H), 7.80-7.88 (m, 1H), 7.46-7.53 (m, 1H), 7.41-7.46 (m, 1H), 7.30-7.37 (m, 1H), 2.28 (s, 3H), 2.22 (s, 3H). MS obsd. (ESI+) [(M+H)+]: 362.1.

Example 4

2-(5-bromoisoindoline-2-carbonyl)-8-chloro-chromen-4-one

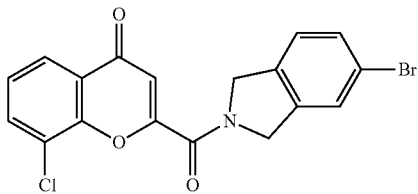

4

To a solution of 8-chloro-4-oxo-chromene-2-carboxylic acid (Int-1, 150 mg, 668 μmol) in DCM (20 mL) was added 5-bromoisoindoline (198 mg, 1 mmol), DIPEA (138 mg, 1.07 mmol) and HATU (381 mg, 1 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 2-(5-bromoisoindoline-2-carbonyl)-8-chloro-chromen-4-one (30 mg, 11.1%) as a white foam. $^1$H NMR (400 MHz, DMSO-d$_6$) δ 8.01-8.12 (m, 2H), 7.61-7.69 (m, 1H), 7.49-7.60 (m, 2H), 7.30-7.43 (m, 1H), 6.90-6.93 (m, 1H), 5.23-5.36 (m, 2H), 4.83-4.96 (m, 2H). MS obsd. (ESI+) [(M+H)+]: 404.1 & 406.1.

Example 5

3-(2-(4-(8-chloro-4-oxo-chromene-2-carboxamido)-3-(trifluoromethyl)phenoxy)ethoxy)cyclobutanecarboxylic Acid

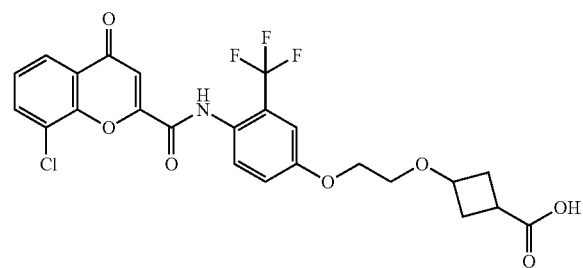

5

Step 1: Preparation of 8-chloro-N-(4-methoxy-2-(trifluoromethyl)phenyl)-4-oxo-chromene-2-carboxamide Acid

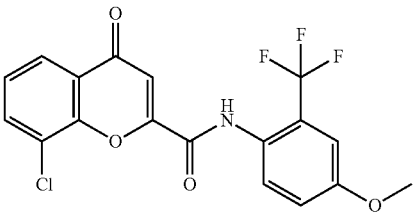

5a

To a solution of 8-chloro-4-oxo-chromene-2-carboxylic acid (Int-1, 200 mg, 890 μmol) in DCM (20 mL) was added 4-methoxy-2-(trifluoromethyl)aniline (204 mg, 1.07 mmol), DIPEA (345 mg, 2.67 mmol) and HATU (508 mg, 1.34 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo, the residue was purified by silica gel flash chromatography (elution with PE/EtOAc=10:1-1:2) to give 8-chloro-N-(4-methoxy-2-(trifluoromethyl)phenyl)-4-oxo-chromene-2-carboxamide (300 mg, 84.7%) as a yellow solid. $^1$H NMR (400 MHz, DMSO-d$_6$) δ 10.16-10.21 (m, 1H), 7.98-8.13 (m, 2H), 7.64-7.70 (m, 1H), 7.52-7.61 (m, 1H), 7.30-7.38 (m, 2H), 6.99-7.06 (m, 1H), 3.88 (s, 3H). MS obsd. (ESI+) [(M+H)+]: 398.1.

Step 2: Preparation of 8-chloro-N-(4-hydroxy-2-(trifluoromethyl)phenyl)-4-oxo-chromene-2-carboxamide

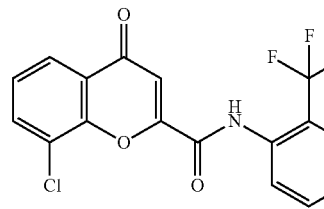

5b

To a solution of 8-chloro-N-(4-methoxy-2-(trifluoromethyl)phenyl)-4-oxo-chromene-2-carboxamide (200 mg, 503 μmol) in DCM (20 mL) was added BBr$_3$ (1 M solution in DCM, 8 mL, 8 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 8-chloro-N-(4-hydroxy-2-(trifluoromethyl)phenyl)-4-oxo-chromene-2-carboxamide (150 mg, 77.7%) as a yellow solid, which was used in the next step directly without further purification. MS obsd. (ESI+) [(M+H)+]: 384.1.

Step 3: Preparation of methyl 3-(2-(4-(8-chloro-4-oxo-chromene-2-carboxamido)-3-(trifluoromethyl)phenoxy)ethoxy)cyclobutanecarboxylate

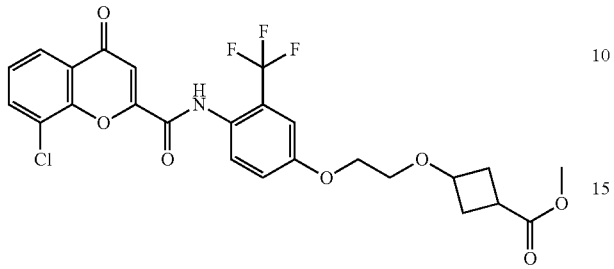

5c

To a solution of 8-chloro-N-(4-hydroxy-2-(trifluoromethyl)phenyl)-4-oxo-chromene-2-carboxamide (150 mg, 391 μmol), methyl 3-[2-(p-tolylsulfonyloxy)ethoxy]cyclobutanecarboxylate (Int-8, 154 mg, 469 μmol) in DMF (5 mL) was added K$_2$CO$_3$ (108 mg, 782 μmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give methyl 3-(2-(4-(8-chloro-4-oxo-chromene-2-carboxamido)-3-(trifluoromethyl)phenoxy)ethoxy)cyclobutanecarboxylate (140 mg, 66.3%) as a yellow oil, which was used in next step directly without further purification. MS obsd. (ESI$^+$) [(M+H)$^+$]: 540.1.

Step 4: Preparation of 3-(2-(4-(8-chloro-4-oxo-chromene-2-carboxamido)-3-(trifluoromethyl)phenoxy)ethoxy)cyclobutanecarboxylic Acid

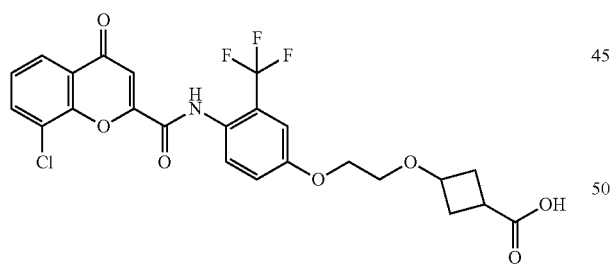

5

To a solution of methyl 3-(2-(4-(8-chloro-4-oxo-chromene-2-carboxamido)-3-(trifluoromethyl)phenoxy)ethoxy)cyclobutanecarboxylate (140 mg, 259 μmol) in THF (4 mL) was added 3.0 M hydrogen chloride (3 mL, 9 mmol) at room temperature and the resulting mixture was then stirred at 50° C. for 2 hours. After the reaction was completed, the mixture was then concentrated in vacuo and the residue was purified by preparative HPLC to give 3-(2-(4-(8-chloro-4-oxo-chromene-2-carboxamido)-3-(trifluoromethyl)phenoxy)ethoxy)cyclobutanecarboxylic acid (44 mg, 32.3%) as a light yellow foam. $^1$H NMR (400 MHz, DMSO-d$_6$) δ 12.11-12.23 (m, 1H), 10.08-10.23 (m, 1H), 7.98-8.12 (m, 2H), 7.62-7.69 (m, 1H), 7.51-7.60 (m, 1H), 7.30-7.40 (m, 2H), 6.96-7.05 (m, 1H), 4.19-4.24 (m, 2H), 4.12-4.19 (m, 1H), 3.62-3.69 (m, 2H), 2.86-2.96 (m, 1H), 2.36-2.46 (m, 2H), 2.09-2.20 (m, 1H), 1.92-2.04 (m, 1H). MS obsd. (ESI$^+$) [(M+H)$^+$]: 526.1.

Example 6

8-chloro-4-oxo-N-(5-(trifluoromethyl)-1,3,4-thiadiazol-2-yl)-chromene-2-carboxamide

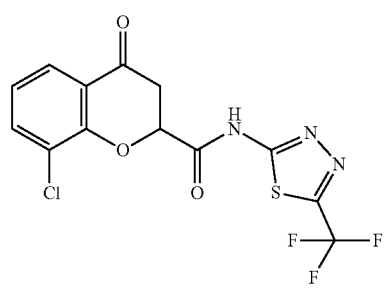

6

To a solution of 8-chloro-4-oxo-chromene-2-carboxylic acid (Int-1, 90 mg, 401 μmol) in DCM (20 mL) was added 5-(trifluoromethyl)-1,3,4-thiadiazol-2-amine (136 mg, 0.81 mmol), DIPEA (82.9 mg, 641 μmol) and HATU (229 mg, 601 μmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo, the residue was purified by preparative HPLC to give 8-chloro-4-oxo-N-(5-(trifluoromethyl)-1,3,4-thiadiazol-2-yl)-chromene-2-carboxamide (86 mg, 57.1%) as a white foam. $^1$H NMR (400 MHz, DMSO-d$_6$) δ 8.07-8.12 (m, 1H), 7.99-8.06 (m, 1H), 7.48-7.63 (m, 1H), 7.37 (s, 1H). MS obsd. (ESI$^+$) [(M+H)$^+$]: 376.1.

Example 7

3-(5-chloro-2-(8-chloro-4-oxo-chromene-2-carboxamido)phenoxy)cyclobutane-1-carboxylic Acid

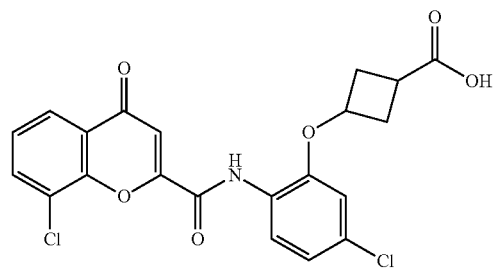

7

Step 1: Preparation of 8-chloro-N-(4-chloro-2-methoxyphenyl)-4-oxo-chromene-2-carboxamide

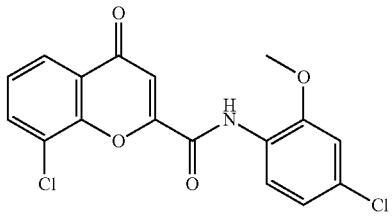

7a

To a solution of 8-chloro-4-oxo-chromene-2-carboxylic acid (Int-1, 1 g, 4.45 mmol) in DCM (20 mL) was added 4-chloro-2-methoxyaniline (842 mg, 5.34 mmol), DIPEA (1.15 g, 8.9 mmol) and HATU (3.3 g, 8.9 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by silica gel flash chromatography (elution with PE/EtOAc=10:1~1:3) to give 8-chloro-N-(4-chloro-2-methoxyphenyl)-4-oxo-chromene-2-carboxamide (1.3 g, 80.3%) as a yellow solid. MS obsd. (ESI$^+$) [(M+H)$^+$]: 364.1.

Step 2: Preparation of 8-chloro-N-(4-chloro-2-hydroxyphenyl)-4-oxo-chromene-2-carboxamide

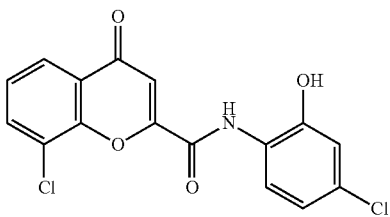

7b

To a solution of 8-chloro-N-(4-chloro-2-methoxyphenyl)-4-oxo-chromene-2-carboxamide (1.2 g, 3.3 mmol) in DCM (40 mL) was added $BBr_3$ (1 M solution in DCM, 25 mL, 25 mmol) at room temperature and the resulting mixture was stirred at room temperature overnight. After the reaction was completed, the mixture was concentrated in vacuo and the residue was suspended in saturated $NH_4Cl$ solution (30 mL). The solid was collected by filtration and dried in vacuo to give 8-chloro-N-(4-chloro-2-hydroxyphenyl)-4-oxo-chromene-2-carboxamide (800 mg, 69.3%) as a yellow solid, which was used in the next step directly without further purification. MS obsd. (ESI$^+$) [(M+H)$^+$]: 350.1.

Step 3: Preparation of methyl 3-(5-chloro-2-(8-chloro-4-oxo-chromene-2-carboxamido)phenoxy)cyclobutane-1-carboxylate

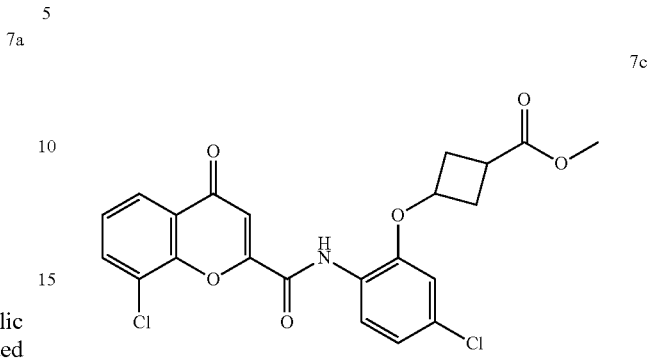

7c

To a solution of 8-chloro-N-(4-chloro-2-hydroxyphenyl)-4-oxo-chromene-2-carboxamide (190 mg, 543 µmol), methyl 3-chlorocyclobutane-1-carboxylate (105 mg, 75 µL, 543 µmol) in DMF (5 mL) was added $Cs_2CO_3$ (260 mg, 782 µmol) at room temperature and the resulting mixture was then stirred at 90° C. for 12 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo to give methyl 3-(5-chloro-2-(8-chloro-4-oxo-chromene-2-carboxamido)phenoxy)cyclobutane-1-carboxylate (200 mg, 79.8%) as a yellow foam, which was used in next step directly without further purification. MS obsd. (ESI$^+$) [(M+H)$^+$]: 462.1.

Step 4: Preparation of 3-(5-chloro-2-(8-chloro-4-oxo-chromene-2-carboxamido)phenoxy)cyclobutane-1-carboxylic Acid

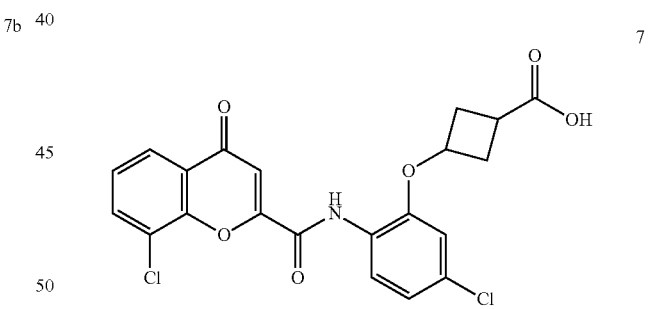

7

To a solution of methyl 3-(5-chloro-2-(8-chloro-4-oxo-chromene-2-carboxamido)phenoxy)cyclobutane-1-carboxylate (150 mg, 324 µmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 3-(5-chloro-2-(8-chloro-4-oxo-chromene-2-carboxamido)phenoxy)cyclobutane-1-carboxylic acid (10 mg, 6.88%) as a light yellow foam. $^1$H NMR (400 MHz, DMSO-$d_6$) δ 12.29-12.42 (m, 1H), 9.45-9.56 (m, 1H), 8.31-8.40 (m, 1H), 8.09-8.17 (m, 1H), 8.02-8.09 (m, 1H), 7.52-7.62 (m, 1H), 7.08-7.17 (m, 2H), 7.06 (s, 1H), 5.00-5.11 (m, 1H), 2.67-2.86 (m, 3H), 2.26-2.39 (m, 2H). MS obsd. (ESI$^+$) [(M+H)$^+$]: 448.1.

Example 8

8-chloro-N-(4-chloro-2-methylphenyl)-4-oxo-chromene-2-carboxamide

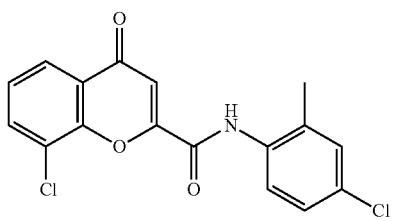

8

To a solution of 8-chloro-4-oxo-chromene-2-carboxylic acid (Int-1, 100 mg, 445 µmol) in DCM (20 mL) was added 4-chloro-2-methylaniline (126 mg, 0.89 mmol), DIPEA (173 mg, E34 mmol) and HATU (254 mg, 668 µmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-N-(4-chloro-2-methylphenyl)-4-oxo-chromene-2-carboxamide (30 mg, 19.4%) as a white foam. $^1$H NMR (400 MHz, DMSO-d$_6$) δ 10.00-10.07 (m, 1H), 8.07-8.13 (m, 1H), 8.01-8.07 (m, 1H), 7.62-7.71 (m, 1H), 7.50-7.60 (m, 1H), 7.40-7.47 (m, 1H), 7.30-7.38 (m, 1H), 7.01-7.08 (m, 1H), 2.37 (s, 3H). MS obsd. (ESI$^+$) [(M+H)$^+$]: 348.1.

Example 9

8-chloro-N-(2,4-dichlorobenzyl)-4-oxo-chromene-2-carboxamide

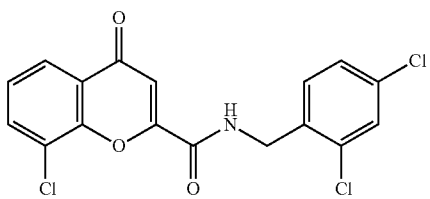

9

To a solution of 8-chloro-4-oxo-chromene-2-carboxylic acid (Int-1, 100 mg, 445 µmol) in DCM (20 mL) was added (2,4-dichlorophenyl)methanamine (157 mg, 890 µmol), DIPEA (92.1 mg, 712 µmol) and HATU (254 mg, 668 µmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-N-(2,4-dichlorobenzyl)-4-oxo-chromene-2-carboxamide (9 mg, 5.28%) as yellow foam. $^1$H NMR (400 MHz, DMSO-d$_6$) δ 9.25-9.31 (m, 1H), 7.97-8.08 (m, 2H), 7.62-7.70 (m, 1H), 7.50-7.58 (m, 1H), 7.44-7.47 (m, 2H), 6.94-7.01 (m, 1H), 4.47-4.63 (m, 2H). MS obsd. (ESI$^+$) [(M+H)$^+$]: 382.1.

Example 10

N-(5-bromo-3-methylpyridin-2-yl)-8-chloro-4-oxo-chromene-2-carboxamide

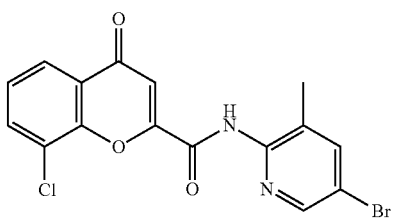

10

To a solution of 8-chloro-4-oxo-chromene-2-carboxylic acid (Int-1, 150 mg, 668 µmol) in DCM (20 mL) was added 5-bromo-3-methylpyridin-2-amine (200 mg, 1.07 mmol), DIPEA (138 mg, 1.07 mmol) and HATU (381 mg, 1 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give N-(5-bromo-3-methylpyridin-2-yl)-8-chloro-4-oxo-chromene-2-carboxamide (70 mg, 26.6%) as a white foam. $^1$H NMR (400 MHz, DMSO-d$_6$) δ 10.81-10.90 (m, 1H), 8.37-8.49 (m, 1H), 7.97-8.14 (m, 3H), 7.48-7.60 (m, 1H), 7.02-7.09 (m, 1H), 2.27 (s, 3H). MS obsd. (ESI$^+$) [(M+H)$^+$]: 393.1 & 395.1.

Example 11

4-(5-chloro-2-(6,8-dichloro-4-oxo-chromene-2-carboxamido)phenoxy)butanoic Acid

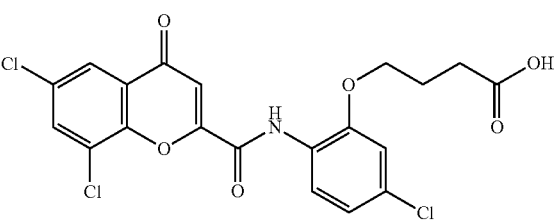

11

Step 1: Preparation of 6,8-dichloro-N-(4-chloro-2-methoxyphenyl)-4-oxo-chromene-2-carboxamide Step 3: Preparation of methyl 4-(5-chloro-2-(6,8-dichloro-4-oxo-chromene-2-carboxamido)phenoxy)butanoate

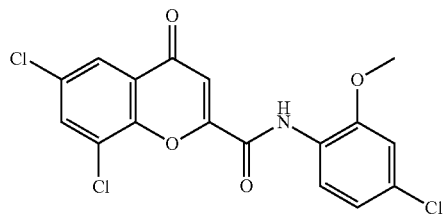

11a

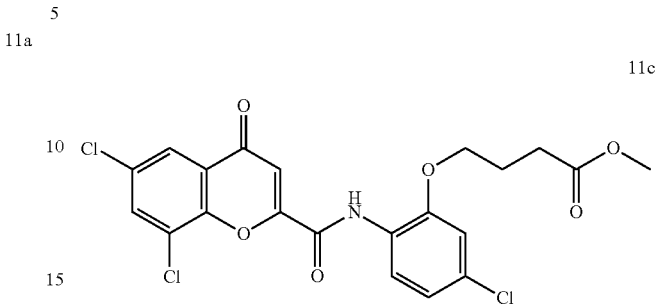

11c

To a solution of 6,8-dichloro-4-oxo-chromene-2-carboxylic acid (Int-2, 1.3 g, 5.02 mmol) in DCM (20 mL) was added 4-chloro-2-methoxyaniline (949 mg, 6.02 mmol), DIPEA (1.15 g, 8.9 mmol) and HATU (3.3 g, 8.9 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by silica gel flash chromatography (elution with PE/EtOAc=10:1-1:4) to give 6,8-dichloro-N-(4-chloro-2-methoxyphenyl)-4-oxo-chromene-2-carboxamide (1.6 g, 80%) as a yellow solid. MS obsd. (ESI$^+$) [(M+H)$^+$]: 398.1.

To a solution of 6,8-dichloro-N-(4-chloro-2-hydroxyphenyl)-4-oxo-chromene-2-carboxamide (190 mg, 494 μmol), methyl 4-bromobutanoate (98.4 mg, 68.3 μl, 543 μmol) in DMF (5 mL) was added $K_2CO_3$ (137 mg, 988 μmol) at room temperature and the resulting mixture was then stirred at 90° C. for 12 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo to give methyl 4-(5-chloro-2-(6,8-dichloro-4-oxo-chromene-2-carboxamido)phenoxy)butanoate (100 mg, 41.8%) as a yellow oil, which was used in next step directly without further purification. MS obsd. (ESI$^+$) [(M+H)$^+$]: 484.1.

Step 2: Preparation of 8-chloro-N-(4-chloro-2-hydroxyphenyl)-4-oxo-chromene-2-carboxamide Step 4: Preparation of 4-(5-chloro-2-(6,8-dichloro-4-oxo-chromene-2-carboxamido)phenoxy)butanoic Acid

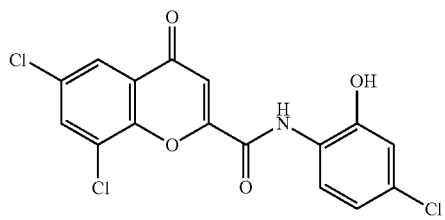

11b

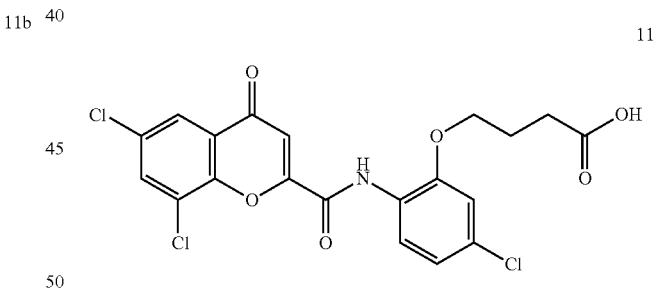

11

To a solution of 6,8-dichloro-N-(4-chloro-2-methoxyphenyl)-4-oxo-chromene-2-carboxamide (1.6 g, 4.01 mmol) in DCM (40 mL) was added BBr$_3$ (1 M solution in DCM, 25 mL, 25 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 6,8-dichloro-N-(4-chloro-2-hydroxyphenyl)-4-oxo-chromene-2-carboxamide (1 g, 64.8%) as a yellow foam, which was used in the next step directly without further purification. MS obsd. (ESI$^+$) [(M+H)$^+$]: 384.1.

To a solution of methyl 4-(5-chloro-2-(6,8-dichloro-4-oxo-chromene-2-carboxamido)phenoxy)butanoate (120 mg, 248 μmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 4-(5-chloro-2-(6,8-dichloro-4-oxo-chromene-2-carboxamido)phenoxy)butanoic acid (7 mg, 6.01%) as a light yellow foam. $^1$H NMR (400 MHz, DMSO-d$_6$) δ 12.11-12.18 (m, 1H), 9.45-9.55 (m, 1H), 8.24-8.34 (m, 2H), 7.88-8.05 (m, 1H), 7.22-7.33 (m, 1H), 7.07-7.16 (m, 1H), 7.00-7.07 (m, 1H), 4.14-4.25 (m, 2H), 2.41-2.47 (m, 2H), 1.98-2.08 (m, 2H). MS obsd. (ESI$^+$) [(M+H)$^+$]: 470.1.

Example 12

8-chloro-N-(4-chloro-2-(trifluoromethyl)phenyl)-4-oxo-chromene-2-carboxamide

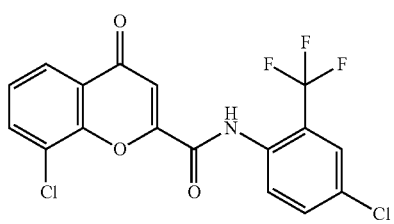

12

To a solution of 8-chloro-4-oxo-chromene-2-carboxylic acid (Int-1, 200 mg, 890 μmol) in DCM (20 mL) was added 4-chloro-2-(trifluoromethyl)aniline (209 mg, 1.07 mmol), DIPEA (230 mg, 1.78 mmol) and HATU (760 mg, 2 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-N-(4-chloro-2-(trifluoromethyl)phenyl)-4-oxo-chromene-2-carboxamide (60 mg, 16.8%) as a white foam. $^1$H NMR (400 MHz, DMSO-$d_6$) δ 10.24-10.30 (m, 1H), 8.01-8.12 (m, 2H), 7.94-7.96 (m, 1H), 7.87-7.92 (m, 2H), 7.53-7.60 (m, 1H), 7.00-7.08 (m, 1H). MS obsd. (ESI$^+$) [(M+H)$^+$]: 402.1.

Example 13

6,8-dichloro-N-(4-chloro-2-methylphenyl)-4-oxo-chromene-2-carboxamide

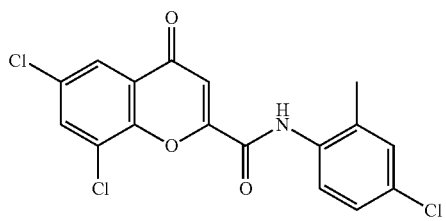

13

To a solution of 6,8-dichloro-4-oxo-chromene-2-carboxylic acid (Int-2, 200 mg, 772 μmol) in DCM (20 mL) was added 4-chloro-2-methylaniline (175 mg, 1.24 mmol), DIPEA (160 mg, 1.24 mmol) and HATU (440 mg, 1.16 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 6,8-dichloro-N-(4-chloro-2-methylphenyl)-4-oxo-chromene-2-carboxamide (10 mg, 3.39%) as a white foam. $^1$H NMR (400 MHz, DMSO-$d_6$) δ 10.04-10.14 (m, 1H), 8.24-8.34 (m, 1H), 7.95-8.00 (m, 1H), 7.57-7.66 (m, 1H), 7.40-7.47 (m, 1H), 7.30-7.39 (m, 1H), 7.04-7.12 (m, 1H), 2.31 (s, 3H). MS obsd. (ESI$^+$) [(M+H)$^+$]: 382.1.

Example 14

8-Chloro-2-(6-methoxy-3,4-dihydro-1H-isoquinoline-2-carbonyl)chromen-4-one

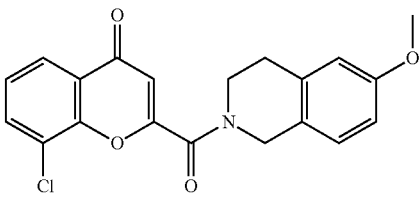

14

A solution of 8-chloro-4-oxo-chromene-2-carboxylic acid (Int-1, 50 mg, 0.22 mmol), 6-methoxy-1,2,3,4-tetrahydroisoquinoline (54.5 mg, 0.33 mmol), HATU (169 mg, 0.45 mmol) and TEA (89.9 mg, 0.89 mmol) in DCM (2 mL) was stirred at room temperature for 10 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-2-(6-methoxy-3,4-dihydro-1H-isoquinoline-2-carbonyl) chromen-4-one (10 mg, 12.1%) as yellow solid. $^1$H NMR (DMSO-$d_6$, 400 MHz): δ 8.00-8.07 (m, 2H), 7.54 (t, J=7.89 Hz, 1H), 7.00-7.23 (m, 1H), 6.67-6.85 (m, 3H), 4.66-4.84 (m, 2H), 3.81 (t, J=5.81 Hz, 2H), 3.67-3.78 (m, 3H), 2.79-3.05 (m, 2H). MS obsd. (ESI+) [(M+H)+]: 370.1.

Example 15

8-chloro-4-oxo-N-(o-tolyl)-chromene-2-carboxamide

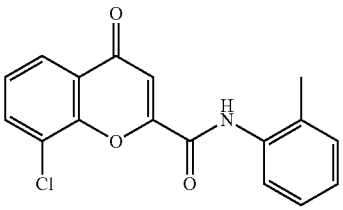

15

To a solution of 8-chloro-4-oxo-chromene-2-carboxylic acid (100 mg, 445 μmol) in DCM (20 mL) was added o-toluidine (47.7 mg, 445 μmol), DIPEA (92.1 mg, 712 μmol) and HATU (254 mg, 668 μmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-4-oxo-N-(o-tolyl)-chromene-2-carboxamide (5 mg, 3.58%) as a light yellow foam. $^1$H NMR (400 MHz, DMSO-$d_6$) δ 9.93-9.99 (m, 1H), 8.02-8.12 (m, 2H), 7.61-7.68 (m, 1H), 7.53-7.59 (m, 1H), 7.17-7.38 (m, 3H), 7.03-7.08 (m, 1H), 2.38 (s, 3H). MS obsd. (ESI$^+$) [(M+H)$^+$]: 314.1.

Example 16

8-Chloro-2-(7-chloro-3,4-dihydro-1H-isoquinoline-2-carbonyl)chromen-4-one

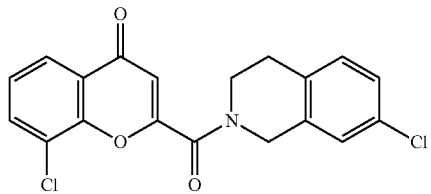

16

A solution of 8-chloro-4-oxo-chromene-2-carboxylic acid (Int-1, 50 mg, 0.22 mmol), 7-chloro-1,2,3,4-tetrahydroisoquinoline (56 mg, 0.33 mmol), HATU (169 mg, 0.44 mmol) and TEA (89.9 mg, 0.89 mmol) in DCM (2 mL) was stirred at room temperature for 10 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-Chloro-2-(7-chloro-3,4-dihydro-1H-isoquinoline-2-carbonyl)chromen-4-one (10 mg, 12%) as yellow solid. $^1$H NMR (DMSO-d$_6$, 400 MHz): δ 7.96-8.10 (m, 2H), 7.54 (t, J=7.89 Hz, 1H), 7.18-7.46 (m, 3H), 6.66-6.80 (m, 1H), 4.73-4.94 (m, 2H), 3.74-3.91 (m, 2H), 2.84-3.01 (m, 2H). MS obsd. (ESI+) [(M+H)+]: 374.2.

Example 17

2-(6-bromo-1,2,3,4-tetrahydroisoquinoline-2-carbonyl)-8-chloro-chromen-4-one

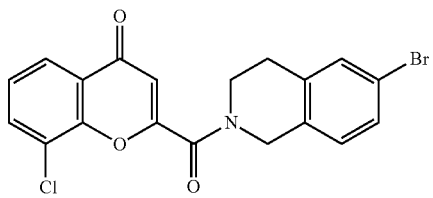

17

To a solution of 8-chloro-4-oxo-chromene-2-carboxylic acid (Int-1, 150 mg, 668 μmol) in DCM (20 mL) was added 6-bromo-1,2,3,4-tetrahydroisoquinoline (212 mg, 1 mmol), DIPEA (138 mg, 1.07 mmol) and HATU (381 mg, 1 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 2-(6-bromo-1,2,3,4-tetrahydroisoquinoline-2-carbonyl)-8-chloro-chromen-4-one (24 mg, 8.58%) as a white foam. $^1$H NMR (400 MHz, DMSO-d$_6$) δ 7.99-8.06 (m, 2H), 7.51-7.58 (m, 1H), 7.41-7.51 (m, 2H), 7.25-7.30 (m, 1H), 6.72-6.76 (m, 1H), 4.71-4.88 (m, 2H), 3.77-3.87 (m, 2H), 2.88-3.03 (m, 2H). MS obsd. (ESI$^+$) [(M+H)$^+$]: 418.1 & 420.1.

Example 18

4-(8-chloro-4-oxo-chromene-2-carboxamido)-3-methylbenzoic Acid

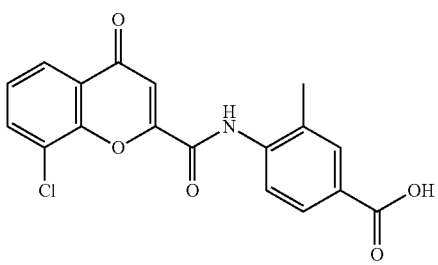

18

Step 1: Preparation of methyl 4-(8-chloro-4-oxo-chromene-2-carboxamido)-3-methylbenzoate

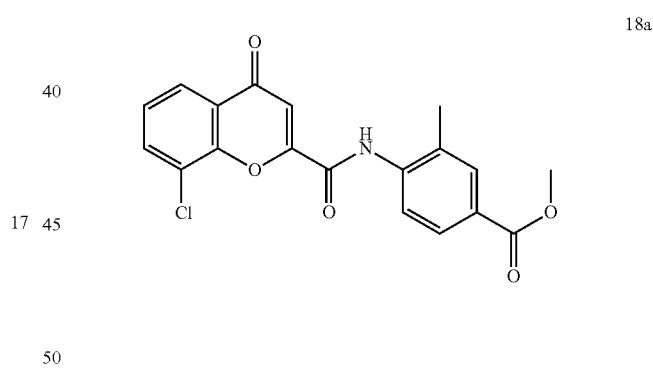

18a

To a solution of 8-chloro-4-oxo-chromene-2-carboxylic acid (Int-1, 250 mg, 1.11 mmol) in DCM (20 mL) was added methyl 4-amino-3-methylbenzoate (184 mg, 1.11 mmol), DIPEA (230 mg, 1.78 mmol) and HATU (635 mg, 1.67 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by silica gel flash chromatography (elution with PE/EtOAc=10:1-1:5) to give methyl 4-(8-chloro-4-oxo-chromene-2-carboxamido)-3-methylbenzoate (110 mg, 26.6%) as a yellow foam. MS obsd. (ESI$^+$) [(M+H)$^+$]: 372.1.

Step 2: Preparation of 4-(8-chloro-4-oxo-chromene-2-carboxamido)-3-methylbenzoic Acid

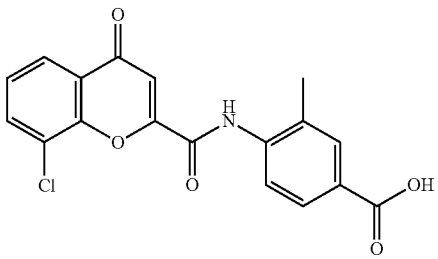

18

To a solution of methyl 4-(8-chloro-4-oxo-chromene-2-carboxamido)-3-methylbenzoate (150 mg, 403 μmol) in THF (4 mL) was added 3.0 M hydrogen chloride (3 mL, 9 mmol) and the resulting mixture was then stirred at 50° C. for 2 hours. After the reaction was completed, the mixture was concentrated in vacuo and the residue was purified by preparative HPLC to give 4-(8-chloro-4-oxo-chromene-2-carboxamido)-3-methylbenzoic acid (20 mg, 13.9%) as a white foam. $^1$H NMR (400 MHz, DMSO-$d_6$) δ 12.75-13.08 (m, 1H), 9.87-10.02 (m, 1H), 8.07-8.13 (m, 1H), 8.02-8.07 (m, 1H), 7.81-7.93 (m, 3H), 7.52-7.60 (m, 1H), 7.05-7.09 (m, 1H), 2.42 (s, 3H). MS obsd. (ESI$^+$) [(M+H)$^+$]: 358.1

Example 19

2-(2-(4-(8-chloro-4-oxo-chromene-2-carboxamido)-3-methylphenoxy)ethoxy)acetic Acid

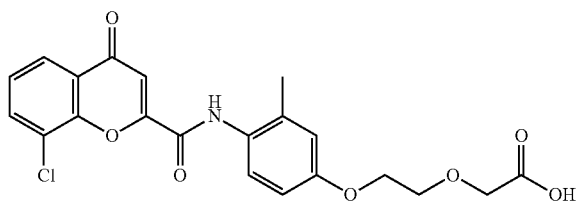

19

Step 1: Preparation of ethyl 2-(2-(4-(8-chloro-4-oxo-chromene-2-carboxamido)-3-methylphenoxy)ethoxy)acetate

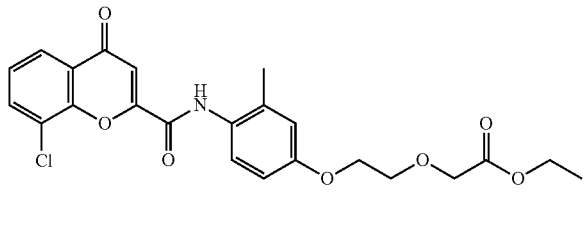

19a

To a solution of 8-chloro-N-(4-hydroxy-2-methylphenyl)-4-oxo-chromene-2-carboxamide (170 mg, 516 μmol), ethyl 2-(2-(tosyloxy)ethoxy)acetate (187 mg, 619 μmol) in DMF (5 mL) was added K$_2$CO$_3$ (143 mg, 1.03 mmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give ethyl 2-(2-(4-(8-chloro-4-oxo-chromene-2-carboxamido)-3-methylphenoxy)ethoxy)acetate (100 mg, 42.2%) as a yellow oil, which was used in next step directly without further purification. MS obsd. (ESI$^+$) [(M+H)$^+$]: 460.1.

Step 2: Preparation of 2-(2-(4-(8-chloro-4-oxo-chromene-2-carboxamido)-3-methylphenoxy)ethoxy)acetic Acid

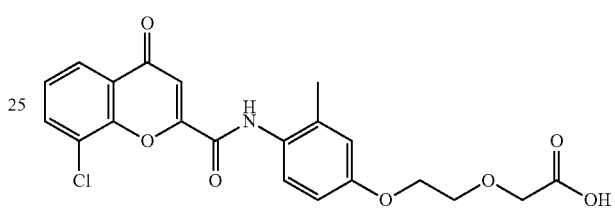

19

To a solution of ethyl 2-(2-(4-(8-chloro-4-oxo-chromene-2-carboxamido)-3-methylphenoxy)ethoxy)acetate (100 mg, 217 μmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 2-(2-(4-(8-chloro-4-oxo-chromene-2-carboxamido)-3-methylphenoxy)ethoxy)acetic acid (7 mg, 7.45%) as a yellow foam. $^1$H NMR (400 MHz, DMSO-$d_6$) δ 12.38-12.96 (m, 1H), 9.86-10.01 (m, 1H), 7.98-8.14 (m, 2H), 7.52-7.63 (m, 1H), 7.40-7.49 (m, 1H), 7.00-7.12 (m, 1H), 6.90-6.95 (m, 1H), 6.74-6.90 (m, 1H), 4.01-4.11 (m, 4H), 3.76-3.89 (m, 2H), 2.28 (s, 3H). MS obsd. (ESI$^+$) [(M+H)$^+$]: 432.1.

Example 20

2-(5-chloro-2-(8-chloro-4-oxo-chromene-2-carboxamido)phenoxy)acetic Acid

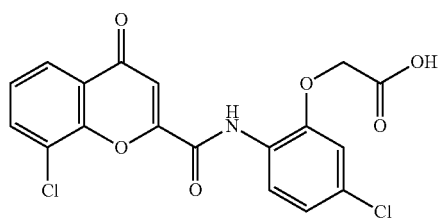

20

Step 1: Preparation of tert-butyl 2-(5-chloro-2-(8-chloro-4-oxo-chromene-2-carboxamido)phenoxy)acetate

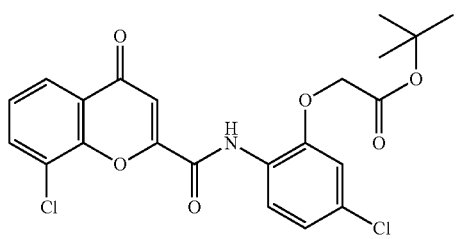

20a

To a solution of 8-chloro-N-(4-chloro-2-hydroxyphenyl)-4-oxo-chromene-2-carboxamide (150 mg, 428 µmol), tert-butyl 2-bromoacetate (83.6 mg, 428 µmol) in DMF (5 mL) was added $K_2CO_3$ (148 mg, 1.07 mmol) at room temperature and the resulting mixture was then stirred at 50° C. for 1 hour. After the reaction was completed, the mixture was diluted with water (30 mL) and extracted with EtOAc (50 mL) three times. The combined organic layer was washed with brine, dried over anhydrous $Na_2SO_4$ and concentrated in vacuo to give tert-butyl 2-(5-chloro-2-(8-chloro-4-oxo-chromene-2-carboxamido)phenoxy)acetate (100 mg, 50.3%) as a yellow oil, which was used in next step directly without further purification. MS obsd. (ESI$^+$) [(M+H)$^+$]: 464.1.

Step 2: Preparation of 2-(5-chloro-2-(8-chloro-4-oxo-chromene-2-carboxamido)phenoxy)acetic Acid

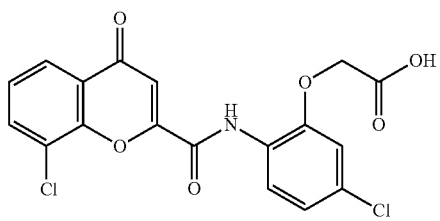

20

To a solution of tert-butyl 2-(5-chloro-2-(8-chloro-4-oxo-chromene-2-carboxamido)phenoxy)acetate (100 mg, 215 µmol) in DCM (4 mL) was added trifluoroacetic acid (5 mL, 64.9 mmol) at room temperature and the resulting mixture was then stirred at room temperature for 2 hours. After the reaction was completed, the mixture was then concentrated in vacuo and the residue was purified by preparative HPLC to give 2-(5-chloro-2-(8-chloro-4-oxo-chromene-2-carboxamido)phenoxy)acetic acid (20 mg, 22.7%) as a yellow foam. $^1$H NMR (400 MHz, DMSO-d$_6$) δ 13.16-13.43 (m, 1H), 9.76-9.83 (m, 1H), 8.23-8.32 (m, 1H), 8.06-8.13 (m, 1H), 8.00-8.06 (m, 1H), 7.52-7.62 (m, 1H), 7.32-7.39 (m, 1H), 7.12-7.22 (m, 1H), 7.03 (s, 1H), 4.99 (s, 2H). MS obsd. (ESI$^+$) [(M+H)$^+$]: 408.1.

Example 21

Methyl 3-(8-chloro-4-oxo-chromene-2-carboxamido)-4-methylbenzoate

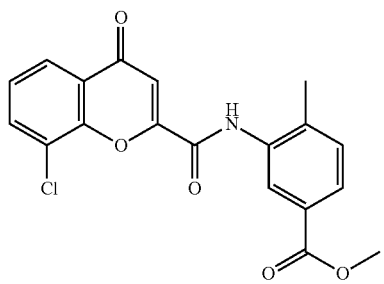

21

To a solution of 8-chloro-4-oxo-chromene-2-carboxylic acid (Int-1, 250 mg, 1.11 mmol) in DCM (20 mL) was added methyl 3-amino-4-methylbenzoate (184 mg, 1.11 mmol), DIPEA (230 mg, 1.78 mmol) and HATU (635 mg, 1.67 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give methyl 3-(8-chloro-4-oxo-chromene-2-carboxamido)-4-methylbenzoate (190 mg, 45.9%) as a yellow foam. $^1$H NMR (400 MHz, DMSO-d$_6$) δ 10.05-10.15 (m, 1H), 8.22-8.34 (m, 1H), 8.00-8.15 (m, 2H), 7.75-7.83 (m, 1H), 7.52-7.61 (m, 1H), 7.46-7.52 (m, 1H), 7.01-7.14 (m, 1H), 3.90 (s, 3H), 2.43 (s, 3H) MS obsd. (ESI$^+$) [(M+H)$^+$]: 372.1.

Example 22

2-(2-(5-chloro-2-(6,8-dichloro-4-oxo-chromene-2-carboxamido)phenoxy)ethoxy)acetic Acid

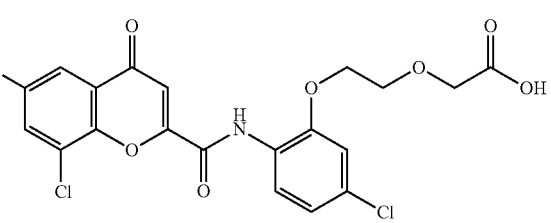

22

Step 1: Preparation of 6,8-dichloro-N-(4-chloro-2-methoxyphenyl)-4-oxo-chromene-2-carboxamide

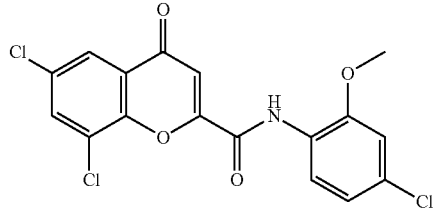

22a

To a solution of 6,8-dichloro-4-oxo-chromene-2-carboxylic acid (Int-2, 1.3 g, 5.02 mmol) in DCM (20 mL) was added 4-chloro-2-methoxyaniline (949 mg, 6.02 mmol), DIPEA (1.3 g, 10 mmol) and HATU (2.6 g, 7 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by silica gel flash chromatography (elution with PE/EtOAc=10:1-1:1) to give 6,8-dichloro-N-(4-chloro-2-methoxyphenyl)-4-oxo-chromene-2-carboxamide (1.6 g, 80%) as a yellow solid. MS obsd. (ESI$^+$) [(M+H)$^+$]: 398.1.

Step 2: Preparation of 6,8-dichloro-N-(4-chloro-2-hydroxyphenyl)-4-oxo-chromene-2-carboxamide

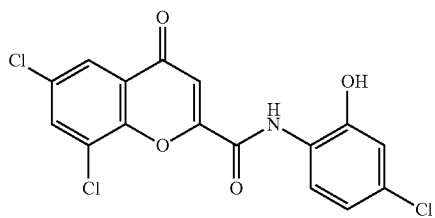

22b

To a solution of 6,8-dichloro-N-(4-chloro-2-methoxyphenyl)-4-oxo-chromene-2-carboxamide (1.6 g, 4.01 mmol) in DCM (30 mL) was added BBr$_3$ (1 M solution in DCM, 15 mL, 15 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 6,8-dichloro-N-(4-chloro-2-hydroxyphenyl)-4-oxo-chromene-2-carboxamide (1 g, 64.8%) as a yellow solid, which was used in the next step directly without further purification. MS obsd. (ESI$^+$) [(M+H)$^+$]: 384.1.

Step 3: Preparation of ethyl 2-(2-(5-chloro-2-(6,8-dichloro-4-oxo-chromene-2-carboxamido)phenoxy)ethoxy)acetate

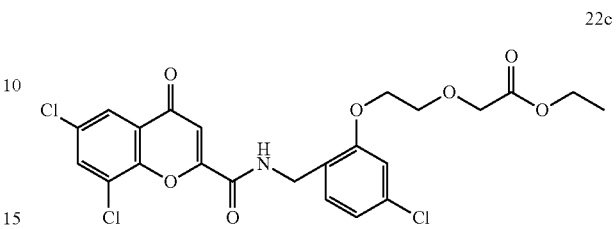

22c

To a solution of 6,8-dichloro-N-(4-chloro-2-hydroxyphenyl)-4-oxo-chromene-2-carboxamide (150 mg, 390 μmol), ethyl 2-(2-(tosyloxy)ethoxy)acetate (142 mg, 468 μmol) in DMF (5 mL) was added K$_2$CO$_3$ (108 mg, 782 μmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give ethyl 2-(2-(5-chloro-2-(6,8-dichloro-4-oxo-chromene-2-carboxamido)phenoxy)ethoxy)acetate (120 mg, 59.8%) as a yellow oil, which was used in next step directly without further purification. MS obsd. (ESI$^+$) [(M+H)$^+$]: 514.1.

Step 4: Preparation of 2-(2-(5-chloro-2-(6,8-dichloro-4-oxo-chromene-2-carboxamido)phenoxy)ethoxy)acetic Acid

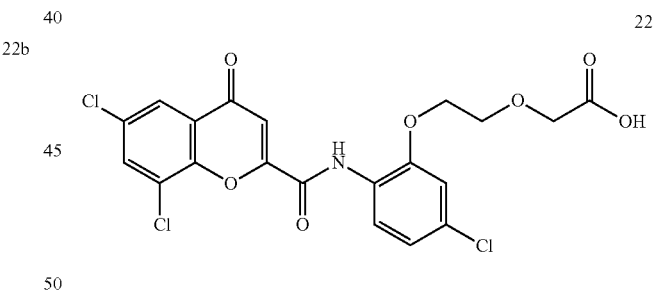

22

To a solution of ethyl 2-(2-(5-chloro-2-(6,8-dichloro-4-oxo-chromene-2-carboxamido)phenoxy)ethoxy)acetate (120 mg, 233 μmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 2-(2-(5-chloro-2-(6,8-dichloro-4-oxo-chromene-2-carboxamido)phenoxy)ethoxy)acetic acid (30 mg, 26.4%) as a light yellow foam. $^1$H NMR (400 MHz, DMSO-d$_6$) δ 12.15-12.22 (m, 1H), 9.54-9.59 (m, 1H), 8.29-8.35 (m, 2H), 7.96-8.01 (m, 1H), 7.32-7.39 (m, 1H), 7.10-7.16 (m, 1H), 7.01-7.06 (m, 1H), 4.32-4.40 (m, 2H), 4.01-4.09 (m, 2H), 3.83-3.92 (m, 2H). MS obsd. (ESI$^+$) [(M+H)$^+$]: 486.1.

Example 23

N-(5-bromo-4-methylpyridin-2-yl)-8-chloro-4-oxo-chromene-2-carboxamide

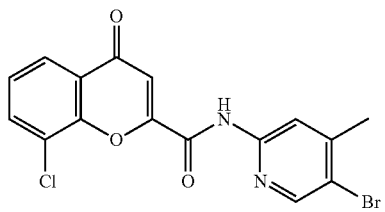

23

To a solution of 8-chloro-4-oxo-chromene-2-carboxylic acid (Int-1, 150 mg, 668 μmol) in DCM (20 mL) was added 5-bromo-4-methylpyridin-2-amine (200 mg, 1.07 mmol), DIPEA (138 mg, 1.07 mmol) and HATU (381 mg, 1 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give N-(5-bromo-4-methylpyridin-2-yl)-8-chloro-4-oxo-chromene-2-carboxamide (70 mg, 26.6%) as a yellow foam. $^1$H NMR (400 MHz, DMSO-$d_6$) δ 10.71-10.81 (m, 1H), 8.49-8.58 (m, 1H), 8.16-8.23 (m, 1H), 8.07-8.12 (m, 1H), 8.01-8.07 (m, 1H), 7.46-7.61 (m, 1H), 7.06-7.14 (m, 1H), 2.45 (s, 3H). MS obsd. (ESI$^+$) [(M+H)$^+$]: 393.1&395.1.

Example 24

2-(2-(5-chloro-2-(8-chloro-4-oxo-chromene-2-carboxamido)phenoxy)ethoxy)acetic Acid

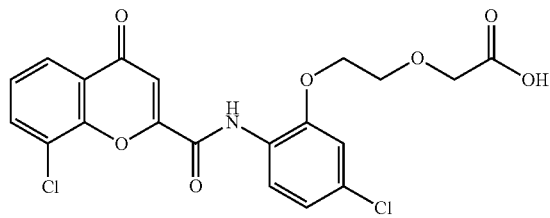

24

Step 1: Preparation of 8-chloro-N-(4-chloro-2-methoxyphenyl)-4-oxo-chromene-2-carboxamide

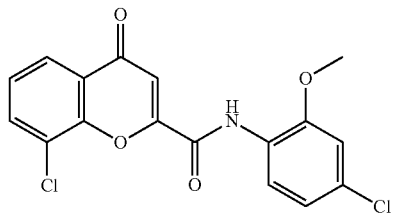

24a

To a solution of 8-chloro-4-oxo-chromene-2-carboxylic acid (Int-1, 1.0 g, 4.45 mmol) in DCM (20 mL) was added 4-chloro-2-methoxyaniline (842 mg, 5.34 mmol), DIPEA (1.15 g, 8.9 mmol) and HATU (2.6 g, 7 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by silica gel flash chromatography (elution with PE/EtOAc=10:1~1:3) to give 8-chloro-N-(4-chloro-2-methoxyphenyl)-4-oxo-chromene-2-carboxamide (1.3 g, 80.2%) as a yellow solid. MS obsd. (ESI$^+$) [(M+H)$^+$]: 364.1.

Step 2: Preparation of 8-chloro-N-(4-chloro-2-hydroxyphenyl)-4-oxo-chromene-2-carboxamide

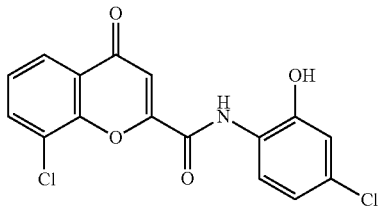

24b

To a solution of 8-chloro-N-(4-chloro-2-methoxyphenyl)-4-oxo-chromene-2-carboxamide (1.2 g, 3.3 mmol) in DCM (30 mL) was added BBr$_3$ (1 M solution in DCM, 25 mL, 25 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 8-chloro-N-(4-chloro-2-hydroxyphenyl)-4-oxo-chromene-2-carboxamide (800 mg, 69.3%) as a yellow solid, which was used in the next step directly without further purification. MS obsd. (ESI$^+$) [(M+H)$^+$]: 350.1.

Step 3: Preparation of ethyl 2-(2-(5-chloro-2-(8-chloro-4-oxo-chromene-2-carboxamido)phenoxy)ethoxy)acetate

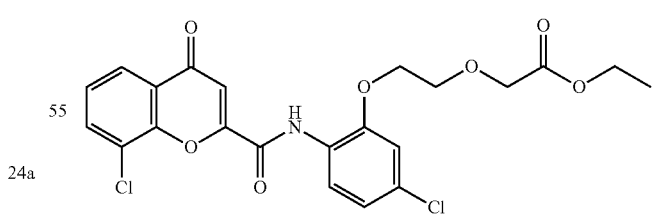

24c

To a solution of 8-chloro-N-(4-chloro-2-hydroxyphenyl)-4-oxo-chromene-2-carboxamide (150 mg, 428 μmol), ethyl 2-(2-(tosyloxy)ethoxy)acetate (155 mg, 514 μmol) in DMF (5 mL) was added K$_2$CO$_3$ (118 mg, 857 μmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give ethyl 2-(2-(5-chloro-2-(8-chloro-4-oxo-chromene-2-carboxamido)phenoxy)ethoxy)acetate (120 mg, 58.3%) as a yellow oil, which was used in next step directly without further purification. MS obsd. (ESI$^+$) [(M+H)$^+$]: 480.1.

Step 4: Preparation of 2-(2-(5-chloro-2-(8-chloro-4-oxo-chromene-2-carboxamido)phenoxy)ethoxy)acetic Acid

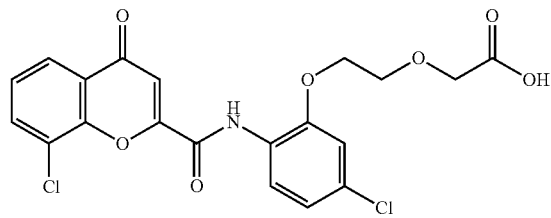

To a solution of ethyl 2-(2-(5-chloro-2-(8-chloro-4-oxo-chromene-2-carboxamido)phenoxy)ethoxy)acetate (120 mg, 250 μmol) in THF (4 mL) was added 3.0 M hydrogen chloride (3 mL, 9 mmol) and the resulting mixture was then stirred at 50° C. for 2 hours.

After the reaction was completed, the mixture was then concentrated in vacuo and the residue was purified by preparative HPLC to give 2-(2-(5-chloro-2-(8-chloro-4-oxo-chromene-2-carboxamido)phenoxy)ethoxy)acetic acid (33 mg, 29.2%) as a light yellow foam. $^1$H NMR (400 MHz, DMSO-d$_6$) δ 12.50-12.68 (m, 1H), 9.43-9.59 (m, 1H), 8.27-8.38 (m, 1H), 8.06-8.12 (m, 1H), 7.98-8.05 (m, 1H), 7.49-7.66 (m, 1H), 7.30-7.41 (m, 1H), 7.09-7.16 (m, 1H), 6.94-7.06 (m, 1H), 4.28-4.43 (m, 2H), 4.08 (s, 2H), 3.84-3.93 (m, 2H). MS obsd. (ESI$^+$) [(M+H)$^+$]: 452.1.

Example 25

Methyl 5-chloro-2-(8-chloro-4-oxo-chromene-2-carboxamido)benzoate

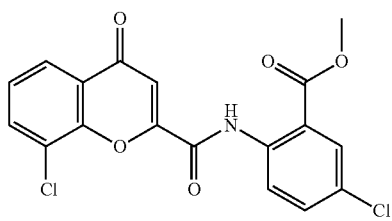

To a solution of 8-chloro-4-oxo-chromene-2-carboxylic acid (Int-1, 250 mg, 1.11 mmol) in DCM (20 mL) was added methyl 2-amino-5-chlorobenzoate (331 mg, 1.78 mmol), DIPEA (230 mg, 1.78 mmol) and HATU (635 mg, 1.67 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give methyl 5-chloro-2-(8-chloro-4-oxo-chromene-2-carboxamido)benzoate (4 mg, 0.916%) as a white foam. $^1$H NMR (DMSO-Y, 400 MHz): δ ppm 8.64-8.71 (m, 1H), 8.08-8.14 (m, 1H), 8.02-8.07 (m, 3H), 7.82-7.87 (m, 1H), 7.54-7.63 (m, 1H), 7.05-7.09 (m, 1H), 3.93 (s, 3H). MS obsd. (ESI$^+$) [(M+H)$^+$]: 392.1.

Example 26

Methyl 4-((8-chloro-4-oxo-chromene-2-carboxamido)methyl)benzoate

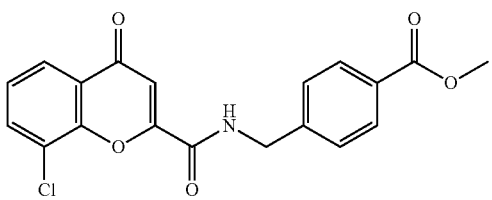

To a solution of 8-chloro-4-oxo-chromene-2-carboxylic acid (Int-1, 100 mg, 445 μmol) in DCM (10 mL) was added methyl 4-(aminomethyl)benzoate (147 mg, 890 μmol), DIPEA (92.1 mg, 712 μmol) and HATU (254 mg, 668 μmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give methyl 4-((8-chloro-4-oxo-chromene-2-carboxamido)methyl)benzoate (10 mg, 6.04%) as a white foam. $^1$H NMR (DMSO-d$_6$, 400 MHz): δ ppm 9.31-9.40 (m, 1H), 7.99-8.09 (m, 2H), 7.89-7.98 (m, 2H), 7.46-7.61 (m, 3H), 6.90-7.02 (m, 1H), 4.54-4.69 (m, 2H), 3.85 (s, 3H). MS obsd. (ESI$^+$) [(M+H)$^+$]: 372.1.

Example 27

Methyl 4-(8-chloro-4-oxo-chromene-2-carboxamido)-3-methylbenzoate

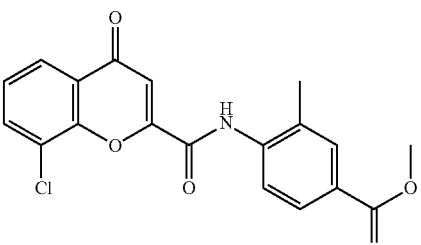

To a solution of 8-chloro-4-oxo-chromene-2-carboxylic acid (Int-1, 250 mg, 1.11 mmol) in DCM (10 mL) was added methyl 4-amino-3-methylbenzoate (184 mg, 1.11 mmol), DIPEA (230 mg, 1.78 mmol) and HATU (635 mg, 1.67 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give methyl 4-(8-chloro-4-oxo-chromene-2-carboxamido)-3-methylbenzoate (110 mg, 26.6%) as a light yellow foam. $^1$H NMR (DMSO-<fc, 400 MHz): δ ppm 9.96-10.04 (m, 1H), 8.08-8.13 (m, 1H), 8.02-8.08 (m, 1H), 7.92-7.98 (m, 2H), 7.85-7.91 (m, 1H), 7.50-7.63 (m, 1H), 6.98-7.14 (m, 1H), 3.93 (s, 3H), 2.44 (s, 3H). MS obsd. (ESI$^+$) [(M+H)$^+$]: 372.1.

Example 28

8-chloro-2-(8-chloro-3,4-dihydro-1H-isoquinoline-2-carbonyl)chromen-4-one

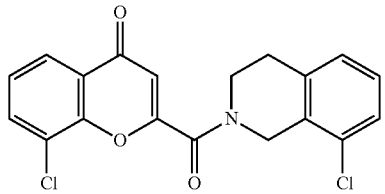

A solution of 8-chloro-4-oxo-chromene-2-carboxylic acid (Int-1, 50 mg, 0.22 mmol), 8-chloro-1,2,3,4-tetrahydroisoquinoline (56 mg, 0.33 mmol), HATU (169 mg, 0.45 mmol,) and TEA (89.9 mg, 0.89 mmol) in DCM (2 mL) was stirred at room temperature for 10 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-2-(8-chloro-3,4-dihydro-1H-isoquinoline-2-carbonyl)chromen-4-one (10 mg, 12%) as a yellow foam. $^1$H NMR (DMSO-$d_6$, 400 MHz): δ 8.04 (dt, 7=1.41, 7.24 Hz, 2H), 7.55 (t, 7=7.95 Hz, 1H), 7.19-7.42 (m, 3H), 6.70-6.83 (m, 1H), 4.73-4.92 (m, 2H), 3.76-3.96 (m, 2H), 2.88-3.09 (m, 2H). MS obsd. (ESI$^+$) [(M+H)$^+$]:374.1.

Example 29

N-(1-(4-bromophenyl)ethyl)-8-chloro-4-oxo-chromene-2-carboxamide

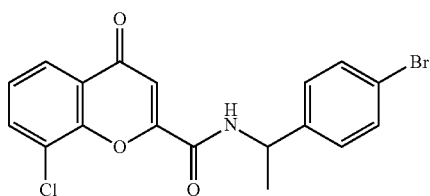

To a solution of 8-chloro-4-oxo-chromene-2-carboxylic acid (Int-1, 100 mg, 445 μmol) in DCM (10 mL) was added 1-(4-bromophenyl)ethanamine (178 mg, 890 μmol), DIPEA (92.1 mg, 712 μmol) and HATU (254 mg, 668 μmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give N-(1-(4-bromophenyl)ethyl)-8-chloro-4-oxo-chromene-2-carboxamide (70 mg, 38.7%) as a white foam. $^1$H NMR (DMSO-$d_6$, 400 MHz): δ ppm 9.10-9.25 (m, 1H), 8.03-8.08 (m, 1H), 7.98-8.02 (m, 1H), 7.49-7.59 (m, 3H), 7.35-7.43 (m, 2H), 6.94-7.00 (m, 1H), 5.04-5.15 (m, 1H), 1.44-1.54 (m, 3H). MS obsd. (ESI$^+$) [(M+H)$^+$]: 406.1&408.1.

Example 30

8-chloro-N-(4-hydroxy-2-methylphenyl)-4-oxo-chromene-2-carboxamide

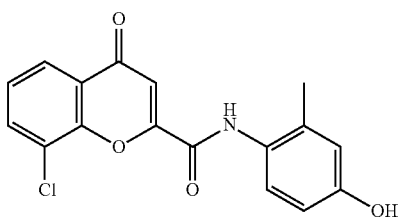

Step 1: Preparation of 8-chloro-N-(4-methoxy-2-methylphenyl)-4-oxo-chromene-2-carboxamide

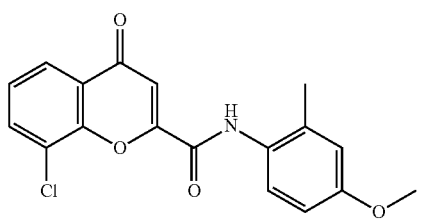

To a solution of 8-chloro-4-oxo-chromene-2-carboxylic acid (Int-1, 300 mg, 1.34 mmol) in DCM (10 mL) was added 4-methoxy-2-methylaniline (275 mg, 2 mmol), DIPEA (518 mg, 4.01 mmol) and HATU (762 mg, 2 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-N-(4-methoxy-2-methylphenyl)-4-oxo-chromene-2-carboxamide (400 mg, 87%) as a white foam. MS obsd. (ESI$^+$) [(M+H)$^+$]: 344.1.

Step 2: Preparation of 8-chloro-N-(4-hydroxy-2-methylphenyl)-4-oxo-chromene-2-carboxamide

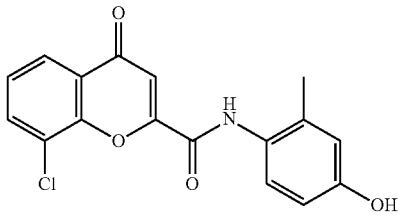

To a solution of 8-chloro-N-(4-methoxy-2-methylphenyl)-4-oxo-chromene-2-carboxamide (400 mg, 1.16 mmol) in DCM (15 mL) was added BBr$_3$ (1 M solution in DCM, 10 mL, 10 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and the solid was purified by preparative HPLC to give 8-chloro-N-(4-hydroxy-2-methylphenyl)-4-oxo-chromene-2-carboxamide (340 mg, 88.6%) as a yellow solid. $^1$H NMR (DMSO-d$_6$, 400 MHz): δ ppm 9.80-9.87 (m, 1H), 9.36-9.47 (m, 1H), 8.00-8.12 (m, 2H), 7.49-7.60 (m, 1H), 7.27-7.36 (m, 1H), 6.98-7.07 (m, 1H), 6.67-6.77 (m, 1H), 6.61-6.67 (m, 1H), 2.21 (s, 3H) MS obsd. (ESI$^+$) [(M+H)$^+$]: 330.1.

Example 31

2-(4-bromoisoindoline-2-carbonyl)-8-chloro-chromen-4-one

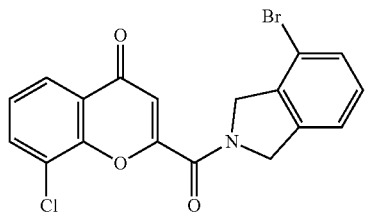

A solution of 8-chloro-4-oxo-chromene-2-carboxylic acid (Int-1, 50 mg, 0.22 mmol), 4-bromoisoindoline (66.1 mg, 0.33 mmol), HATU (169 mg, 0.45 mol) and TEA (89.9 mg, 0.89 mmol) in DCM (2 mL) was stirred at room temperature for 10 hours. After the reaction was completed, the mixture was concentrated in vacuo and the residue was purified by preparative HPLC to give 2-(4-bromoisoindoline-2-carbonyl)-8-chloro-chromen-4-one (10 mg, 11.1%) as yellow solid. $^1$H NMR (DMSO-d$_6$, 400 MHz): δ 8.00-8.14 (m, 2H), 7.52-7.62 (m, 2H), 7.37-7.49 (m, 1H), 7.26-7.35 (m, 1H), 6.89-7.00 (m, 1H), 5.35-5.53 (m, 2H), 4.81-5.08 (m, 2H). MS obsd. (ESI$^+$) [(M+H)$^+$]: 404.1.

Example 32

N-(5-bromo-3-methoxypyridin-2-yl)-8-chloro-4-oxo-chromene-2-carboxamide

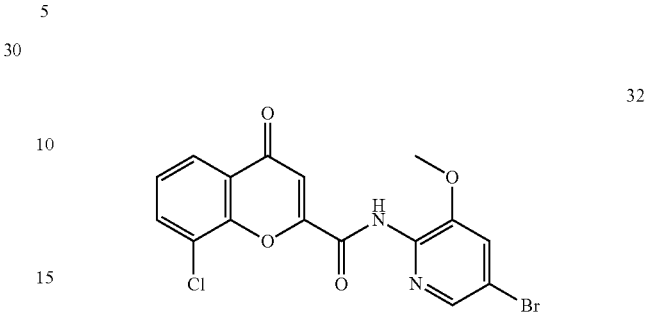

To a solution of 8-chloro-4-oxo-chromene-2-carboxylic acid (Int-1, 150 mg, 668 μmol) in DCM (10 mL) was added 5-bromo-3-methoxypyridin-2-amine (217 mg, 1.07 mmol), DIPEA (138 mg, 1.07 mmol) and HATU (381 mg, 1 mmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give N-(5-bromo-3-methoxypyridin-2-yl)-8-chloro-4-oxo-chromene-2-carboxamide (5 mg, 1.83%) as a yellow foam. $^1$H NMR (DMSO-<fc, 400 MHz): δ ppm 10.49-10.50 (m, 1H), 8.15-8.16 (m, 1H), 8.07-8.08 (m, 1H), 8.01-8.02 (m, 1H), 7.87-7.88 (m, 1H), 7.53-7.57 (m, 1H), 7.01-7.02 (m, 1H), 3.92 (s, 3H). MS obsd. (ESI$^+$) [(M+H)$^+$]: 409.1&411.1.

Example 33

8-chloro-2-(7-nitro-3,4-dihydro-2H-quinoline-1-carbonyl)chromen-4-one

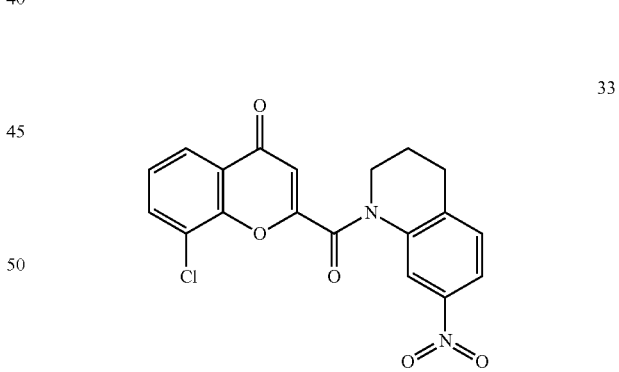

A solution of 8-chloro-4-oxo-chromene-2-carboxylic acid (Int-1, 50 mg, 0.22 mmol), 7-nitro-1,2,3,4-tetrahydroquinoline (59.5 mg, 0.33 mmol), HATU (169 mg, 0.45 mmol) and TEA (89.9 mg, 0.89 mmol) in DCM (2 mL) was stirred at room temperature for 10 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-2-(7-nitro-3,4-dihydro-2H-quinoline-1-carbonyl)chromen-4-one (10 mg, 11.7%) as a yellow solid. $^1$H NMR (DMSO-d$_6$, 400 MHz):

δ 8.15-8.54 (s, 1H), 7.89-8.04 (m, 3H), 7.57 (d, J=8.44 Hz, 1H), 7.50 (t, J=7.89 Hz, 1H), 6.90 (s, 1H), 3.84-3.98 (m, 2H), 2.99 (t, J=6.54 Hz, 2H), 1.93-2.13 (m, 2H). MS obsd. (ESI⁺) [(M+H)⁺]:385.1.

Example 34

3-(2-(5-chloro-2-(8-chloro-4-oxo-chromene-2-carboxamido)phenoxy)ethoxy)cyclobutane-1-carboxylic Acid

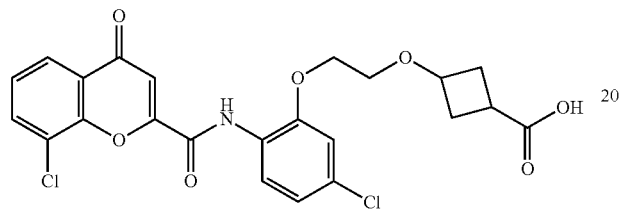

34

Step 1: Preparation of methyl 3-(2-(5-chloro-2-(8-chloro-4-oxo-chromene-2-carboxamido)phenoxy)ethoxy)cyclobutane-1-carboxylate

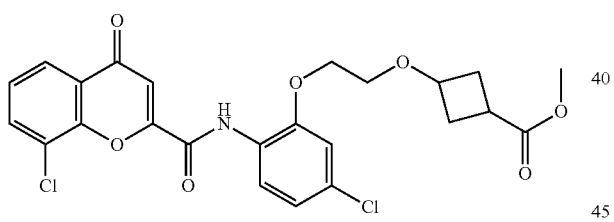

34a

To a solution of 8-chloro-N-(4-chloro-2-hydroxyphenyl)-4-oxo-chromene-2-carboxamide (150 mg, 428 μmol), methyl 3-(2-(tosyloxy)ethoxy)cyclobutane-1-carboxylate (169 mg, 514 μmol) in DMF (5 mL) was added K₂CO₃ (118 mg, 857 μmol) at room temperature and the resulting mixture was then stirred at 50° C. for 12 hours. After the reaction was completed, the mixture was diluted with water (30 mL) and extracted with EtOAc (50 mL) three times. The combined organic layer was washed with brine, dried over anhydrous Na₂SO₄ and concentrated in vacuo to give methyl 3-(2-(5-chloro-2-(8-chloro-4-oxo-chromene-2-carboxamido)phenoxy)ethoxy)cyclobutane-1-carboxylate (120 mg, 55.3%) as a yellow oil, which was used in next step directly without further purification. MS obsd. (ESI⁺) [(M+H)⁺]: 506.1.

Step 2: Preparation of 3-(2-(5-chloro-2-(8-chloro-4-oxo-chromene-2-carboxamido)phenoxy)ethoxy)cyclobutane-1-carboxylic Acid

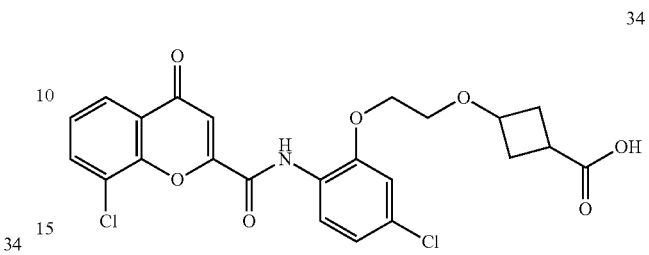

34

To a solution of methyl 3-(2-(5-chloro-2-(8-chloro-4-oxo-chromene-2-carboxamido)phenoxy)ethoxy)cyclobutane-1-carboxylate (120 mg, 237 μmol) in THF (4 mL) was added 3.0 M hydrogen chloride (3 mL, 9 mmol) and the resulting mixture was then stirred at 50° C. for 2 hours. After the reaction was completed, the mixture was then concentrated in vacuo and the residue was purified by preparative HPLC to give 3-(2-(5-chloro-2-(8-chloro-4-oxo-chromene-2-carboxamido)phenoxy)ethoxy)cyclobutane-1-carboxylic acid (52 mg, 44.6%) as a white foam. ¹H NMR (400 MHz, DMSO-d₆) δ 12.06-12.17 (m, 1H), 9.47-9.57 (m, 1H), 8.28-8.37 (m, 1H), 8.07-8.14 (m, 1H), 7.99-8.06 (m, 1H), 7.48-7.60 (m, 1H), 7.30-7.36 (m, 1H), 7.07-7.14 (m, 1H), 6.96-7.03 (m, 1H), 4.28-4.36 (m, 2H), 4.11-4.21 (m, 1H), 3.65-3.76 (m, 2H), 2.78-2.92 (m, 1H), 2.28-2.43 (m, 2H), 2.03-2.18 (m, 1H), 1.87-2.01 (m, 1H). MS obsd. (ESI⁺) [(M+H)⁺]: 492.1.

Example 35

Ethyl 5-(8-chloro-4-oxo-chromene-2-carboxamido)-1,3,4-thiadiazole-2-carboxylate

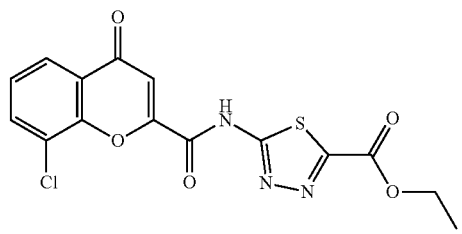

35

To a solution of 8-chloro-4-oxo-chromene-2-carboxylic acid (Int-1, 120 mg, 534 μmol) in DCM (10 mL) was added ethyl 5-amino-1,3,4-thiadiazole-2-carboxylate (187 mg, 1.07 mmol), DIPEA (110 mg, 855 μmol) and HATU (305 mg, 801 μmol) at room temperature and the resulting mixture was then stirred at room temperature for 18 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give ethyl 5-(8-chloro-4-oxo-chromene-2-carboxamido)-1,3,4-thiadiazole-2-carboxylate (50 mg, 24.6%) as a yellow foam. $^1$H NMR (DMSO-d$_6$, 400 MHz): δ ppm 8.06-8.13 (m, 1H), 7.98-8.06 (m, 1H), 7.51-7.60 (m, 1H), 7.31-7.38 (m, 1H), 4.38-4.49 (m, 2H), 1.31-1.41 (m, 3H). MS obsd. (ESI$^+$) [(M+H)$^+$]: 380.1.

Example 36

3-[2-[[2-(8-chloro-4-oxo-chromen-2-yl)-3,4-dihydro-1H-isoquinolin-6-yl]oxy]ethoxy]cyclobutanecarboxylic Acid

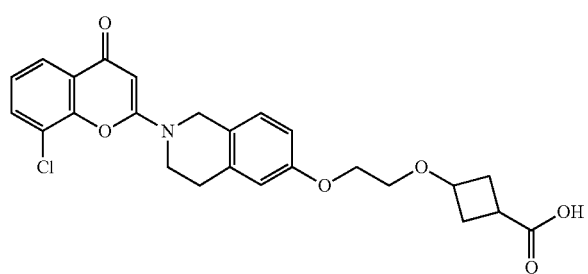

Step 1: Preparation of 8-chloro-2-(6-hydroxy-3,4-dihydro-1H-isoquinolin-2-yl)chromen-4-one A solution of 8-chloro-2-(1,2,4-triazol-1-yl)chromen-4-one (50 mg, 202 μmol), 1,2,3,4-tetrahydroisoquinolin-6-ol; Hydrobromide (Int-9, 92.9 mg, 404 μmol) and K$_2$CO$_3$ (69.8 mg, 505 μmol) in DMF (1 mL) was stirred at 80° C. for 1 hour. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give 8-chloro-2-(6-hydroxy-3,4-dihydro-1H-isoquinolin-2-yl)chromen-4-one (61 mg, 91%).

Step 2: Preparation of methyl 3-[2-[[2-(8-chloro-4-oxo-chromen-2-yl)-3,4-dihydro-1H-isoquinolin-6-yl]oxy]ethoxy]cyclobutanecarboxylate

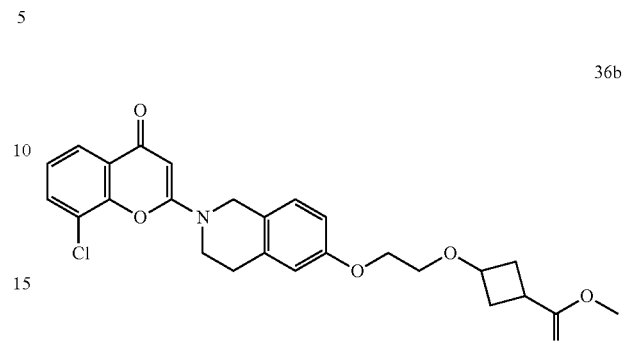

To a solution of 8-chloro-2-(6-hydroxy-3,4-dihydro-1H-isoquinolin-2-yl)chromen-4-one (26 mg, 79.3 μmol), methyl 3-[2-(p-tolylsulfonyloxy)ethoxy]cyclobutanecarboxylate (Int-8, 26 mg, 79.3 μmol) in DMF (5 mL) was added K$_2$CO$_3$ (11 mg, 79.3 μmol) at room temperature and the resulting mixture was then stirred at 90° C. for 2 hours. After the reaction was completed, the mixture was diluted with water (30 mL) and extracted with EtOAc (30 mL) three times. The combined organic layer was washed with brine, dried over anhydrous Na$_2$SO$_4$ and concentrated in vacuo to give methyl 3-[2-[[2-(8-chloro-4-oxo-chromen-2-yl)-3,4-dihydro-1H-isoquinolin-6-yl]oxy]ethoxy]cyclobutanecarboxylate (38 mg) as a yellow oil, which was used in next step directly without further purification.

Step 3: Preparation of 3-[2-[[2-(8-chloro-4-oxo-chromen-2-yl)-3,4-dihydro-1H-isoquinolin-6-yl]oxy]ethoxy]cyclobutanecarboxylic Acid

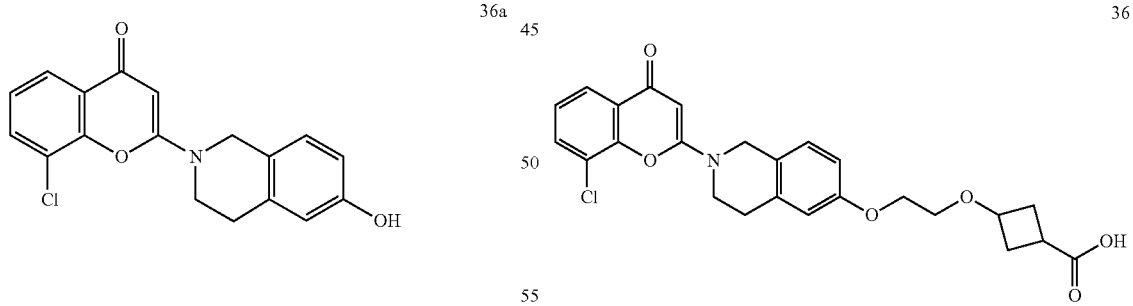

LiOH (8.91 mg, 372 μmol) was added to a solution of methyl 3-[2-[[2-(8-chloro-4-oxo-chromen-2-yl)-3,4-dihydro-1H-isoquinolin-6-yl]oxy]ethoxy]cyclobutanecarboxylate (60 mg, 124 μmol) in MeOH/H$_2$O (1 mL/0.5 mL) and the resulting mixture was stirred at room temperature for 1 hour. After the reaction was completed, the mixture was adjusted to pH~4 by addition of 4 N HCl and then concentrated in vacuo. The residue was purified by preparative HPLC to give 3-[2-[[2-(8-chloro-4-oxo-chromen-2-yl)-3,4-dihydro-1H-isoquinolin-6-yl]oxy]ethoxy]cyclobutanecarboxylic acid (25 mg, 41%) as a white solid. ¹H NMR (DMSO-76, 400 MHz): δ ppm 7.80-7.90 (m, 2H), 7.39 (t, J=7.9 Hz, 1H), 7.19-7.22 (m, 1H), 6.82-6.87 (m, 2H), 5.59 (s, 1H), 4.64 (s, 2H), 4.02-4.08 (m, 2H), 3.89-3.96 (m, 1H), 3.80 (t, J=5.9 Hz, 2H), 3.43-3.67 (m, 2H), 2.96 (t, J=5.9 Hz, 2H), 2.52-2.63 (m, 1H), 2.35-2.47 (m, 2H), 1.93-2.02 (m, 2H). MS obsd. (ESI⁺) [(M+H)⁺]: 470.

Example 37

3-[2-[2-(8-chloro-4-oxo-chromen-2-yl)isoindolin-5-yl]oxyethoxy]cyclobutanecarboxylic Acid

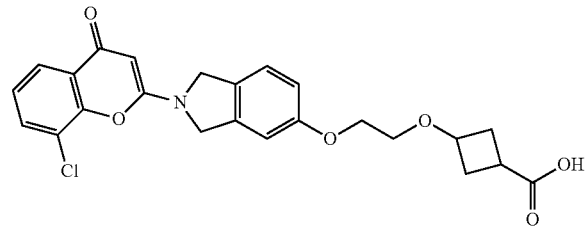

37

Step 1: Preparation of 8-chloro-2-(5-hydroxyisoindolin-2-yl)chromen-4-one

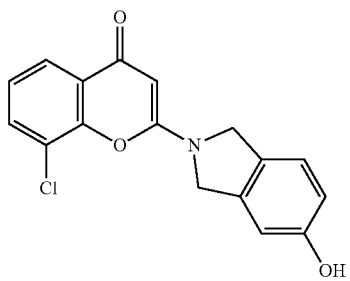

37a

A solution of 8-chloro-2-(1,2,4-triazol-1-yl)chromen-4-one (60 mg, 242 μmol), isoindolin-5-ol; Hydrobromide (Int-10, 62.8 mg, 291 μmol) and K₂CO₃ (83.7 mg, 606 μmol) in DMF (1 mL) was stirred at 80° C. for 1 hour. The mixture was concentrated in vacuo and purified by flash chromatography (elution with DCM/MeOH=100:1-10:1) to give 8-chloro-2-(5-hydroxyisoindolin-2-yl)chromen-4-one (62 mg, 79%) as a yellow oil.

Step 2: Preparation of methyl 3-[2-[2-(8-chloro-4-oxo-chromen-2-yl)isoindolin-5-yl]oxyethoxy]cyclobutanecarboxylate

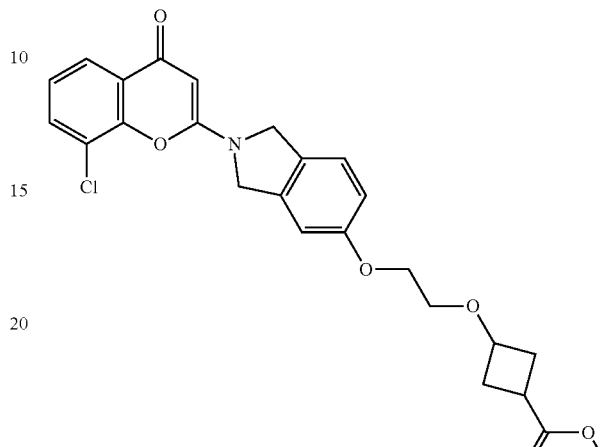

37b

To a solution of 8-chloro-2-(5-hydroxyisoindolin-2-yl)chromen-4-one (76 mg, 242 μmol), methyl 3-[2-(p-tolylsulfonyloxy)ethoxy]cyclobutanecarboxylate (Int-8, 79.5 mg, 242 μmol) in DMF (5 mL) was added K₂CO₃ (33.5 mg, 242 μmol) at room temperature and the resulting mixture was then stirred at 90° C. for 2 hours. After the reaction was completed, the mixture was diluted with water (30 mL) and extracted with EtOAc (30 mL) three times. The combined organic layer was washed with brine, dried over anhydrous Na₂SO₄ and concentrated in vacuo to give methyl 3-[2-[2-(8-chloro-4-oxo-chromen-2-yl)isoindolin-5-yl]oxyethoxy]cyclobutanecarboxylate (110 mg) as a yellow oil, which was used in next step directly without further purification.

Step 3: Preparation of 3-[2-[2-(8-chloro-4-oxo-chromen-2-yl)isoindolin-5-yl]oxyethoxy]cyclobutanecarboxylic Acid

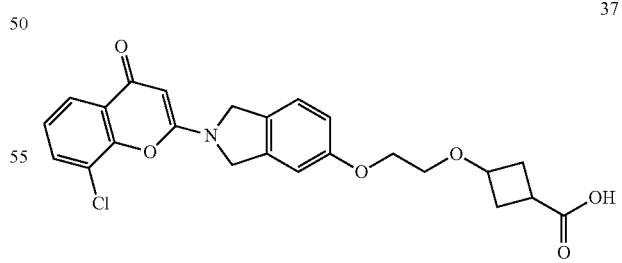

37

LiOH (10.7 mg, 447 μmol) was added to a solution of methyl 3-[2-[2-(8-chloro-4-oxo-chromen-2-yl)isoindolin-5-yl]oxyethoxy]cyclobutanecarboxylate (70 mg, 149 μmol) in MeOH/H₂O (1 mL/0.5 mL) and the resulting mixture was stirred at room temperature for 1 hour. After the reaction was completed, the mixture was adjusted to pH~4 by addition of 4 N HCl and then concentrated in vacuo. The residue was purified by preparative HPLC to give 3-[2-[2-(8-chloro-4-oxo-chromen-2-yl)isoindolin-5-yl]oxyethoxy]cyclobutanecarboxylic acid (45 mg, 66%). ¹H NMR (DMSO-<fc, 400 MHz): δ ppm 7.91 (dd, 7=7.8, 1.6 Hz, 1H), 7.84 (dd, 7=7.9, 1.5 Hz, 1H), 7.40 (t, 7=7.8 Hz, 1H), 7.34 (br d, 7=8.2 Hz, 1H), 7.04 (br s, 1H), 6.94 (dd, 7=8.4, 2.3 Hz, 1H), 5.33 (s, 1H), 4.58-5.11 (m, 4H), 4.03-4.11 (m, 2H), 3.77-4.00 (m, 1H), 3.42-3.70 (m, 2H), 2.52-2.63 (m, 1H), 2.35-2.47 (m, 2H), 1.92-2.04 (m, 2H). MS obsd. (ESI⁺) [(M+H)⁺]:456.

Example 38

3-((4-(8-chloro-4-oxo-chromen-2-yl)piperazin-1-yl)methyl)benzoic Acid

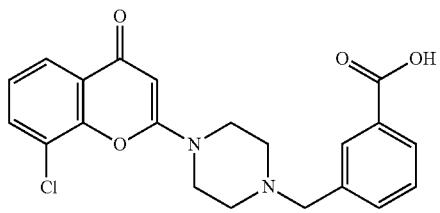

Step 1: Preparation of methyl 3-((4-acetylpiperazin-1-yl)methyl)benzoate

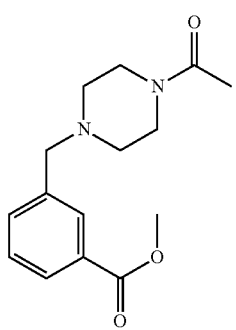

To a solution of 1-(piperazin-1-yl)ethan-1-one (2.56 g, 20.0 mmol) and K₂CO₃ (5.53 g, 40.0 mmol) in THF (50 mL) was added methyl 3-(bromomethyl)benzoate (3.67 g, 16.0 mmol) at room temperature and the resulting mixture was then stirred at 60° C. for 16 hours. After the reaction was completed, the mixture was diluted with water (30 mL) and extracted with EtOAc (50 mL) three times. The combined organic layer was washed with brine, dried over anhydrous Na₂SO₄ and concentrated in vacuo. The residue was purified by column on silica gel (PE:EA=5:1 to 1:1) to give methyl 3-((4-acetylpiperazin-1-yl)methyl)benzoate (1.2 g, 21.7%) as a yellow oil. MS obsd. (ESI⁺) [(M+H)⁺]: 277.0.

Step 2: Preparation of methyl 3-((4-(8-chloro-4-oxo-chromen-2-yl)piperazin-1-yl)methyl)benzoate

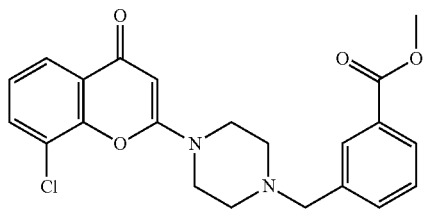

To a solution of methyl 3-((4-acetylpiperazin-1-yl)methyl)benzoate (553 mg, 2.0 mmol) in DCM (10.0 mL) was added POCl₃ (675 mg, 4.4 mmol) at 0° C. and then the mixture was stirred at 25° C. for 1 hour. Then 3-chloro-2-hydroxybenzoic acid (345 mg, 2.0 mmol) was added at 0° C. and the resulting mixture was then stirred at 0° C. for 1 hour. Then the resulting mixture was stirred at 60° C. for another 14 hours. The mixture was concentrated in vacuo and the residue was dissolved in DCM (20.0 mL), NaOAc (1.31 g, 16.0 mmol) was added to the mixture and the mixture was stirred at 60° C. for 4 hours. After the reaction was completed, the mixture was diluted with water (30 mL) and extracted with EtOAc (50 mL) three times. The combined organic layer was washed with brine, dried over anhydrous Na₂SO₄ and concentrated in vacuo. The residue was purified by column on silica gel (DCM:MeOH=200:1 to 25:1) to give methyl 3-((4-(8-chloro-4-oxo-chromen-2-yl)piperazin-1-yl)methyl)benzoate (400 mg, 48.4%) as a yellow oil. MS obsd. (ESI⁺) [(M+H)⁺]: 413.1.

Step 3: Preparation of 3-((4-(8-chloro-4-oxo-chromen-2-yl)piperazin-1-yl)methyl)benzoic Acid

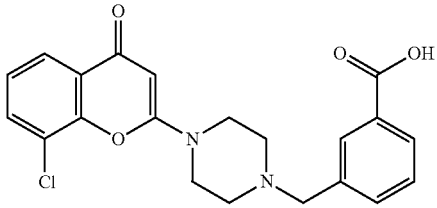

To a solution of methyl 3-((4-(8-chloro-4-oxo-chromen-2-yl)piperazin-1-yl)methyl)benzoate (206 mg, 0.5 mmol) in mixed solvent of TEA/DMF (1.0 mL/1.0 mL) was added LiCl (424 mg, 10.0 mmol). Then the mixture was stirred at 100° C. for 16 hours. After the reaction was completed, the mixture was adjusted to pH~5 by addition of AcOH. The resulting mixture was then concentrated in vacuo, the residue was purified by preparative HPLC to give 3-((4-(8-chloro-4-oxo-chromen-2-yl)piperazin-1-yl)methyl)benzoic acid (16 mg, 8.02%) as a yellow foam. ¹H NMR (400 MHz, DMSO-d₆) δ 12.92-13.32 (m, 1H), 7.85 (dd, 7=7.78, 17.32 Hz, 4H), 7.48-7.74 (m, 2H), 7.39 (t, 7=7.78 Hz, 1H), 5.65 (br. s., 1H), 3.43-4.67 (m, 8H), 2.99-3.29 (m, 2H). MS obsd. (ESI⁺) [(M+H)⁺]: 399.1.

Example 39

2-(2-((8-(8-chloro-4-oxo-chromen-2-yl)-8-azabicyclo[3.2.1]octan-3-yl)oxy)ethoxy)acetic Acid

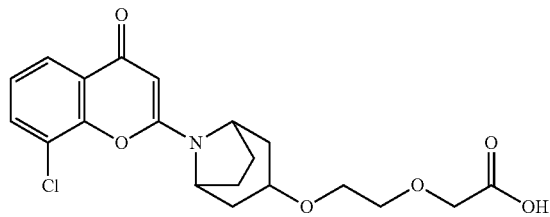

39

Step 1: Preparation of tert-butyl 3-oxo-8-azabicyclo[3.2.1]octane-8-carboxylate

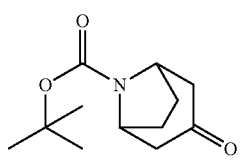

39b

To a solution of tert-butyl 3-hydroxy-8-azabicyclo[3.2.1]octane-8-carboxylate (4.0 g, 17.6 mmol) in ACN (20 mL) was added 2-iodoxybenzoic acid (9.86 g, 35.2 mmol) at room temperature and the resulting mixture was stirred at 50° C. for 4 hours. After the reaction was completed, the mixture was filtered and the liquid was concentrated in vacuo to give tert-butyl 3-oxo-8-azabicyclo[3.2.1]octane-8-carboxylate (3.0 g, 63.1%) as white solid, which was used in next step directly without further purification. MS obsd. (ESI$^+$) [(M+H)$^+$]: 170.1 & 226.1.

Step 2: Preparation of 8-azabicyclo[3.2.1]octan-3-one

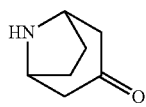

39b

A solution of tert-butyl 3-oxo-8-azabicyclo[3.2.1]octane-8-carboxylate (3.0 g, 13.32 mmol) in dioxane (4 M HCl solution in Dioxane, 10 mL, 40 mmol) was stirred at 25° C. for 2 hours. After the reaction was completed, the mixture was concentrated in vacuo to give 8-azabicyclo[3.2.1]octan-3-one (1.6 g, 100%) as white solid, which was used in next step directly without further purification.

Step 3: Preparation of benzyl 3-oxo-8-azabicyclo[3.2.1]octane-8-carboxylate

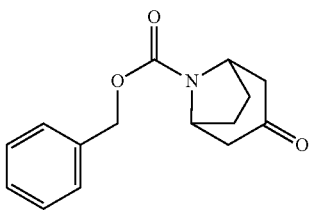

39c

To a solution of tert-butyl 3-oxo-8-azabicyclo[3.2.1]octane-8-carboxylate (1.33 g, 10.59 mmol) and triethylamine (5.9 mL, 42.34 mmol) in DCM (10.0 mL) was added benzyl chloroformate (1.49 mL, 10.59 mmol) at 0° C. and the resulting mixture was then stirred at 0° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give benzyl 3-oxo-8-azabicyclo[3.2.1]octane-8-carboxylate (1.9 g, 69.3%) as yellow oil, which was used in next step directly without further purification. MS obsd. (ESI$^+$) [(M+H)$^+$]: 260.1.

Step 4: Preparation of ethyl 2-(2-((trimethylsilyl)oxy)ethoxy)acetate

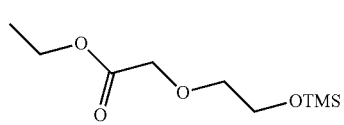

39d

To a solution of ethyl 2-(2-hydroxyethoxy)acetate (2.0 g, 13.5 mmol) in DCM (20.0 mL) was added triethylamine (2.82 mL, 20.25 mmol) and trimethylchlorosilane (2.06 mL, 16.2 mmol) at 0° C. and the resulting mixture was then stirred at 25° C. for 3 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by column (PE:EtOAc=50:1-20:1) to give ethyl 2-(2-((trimethylsilyl)oxy)ethoxy)acetate (1.9 g, 64%) as light yellow oil.

Step 5: Preparation of benzyl 3-(2-(2-ethoxy-2-oxoethoxy)ethoxy)-8-azabicyclo[3.2.1]octane-8-carboxylate

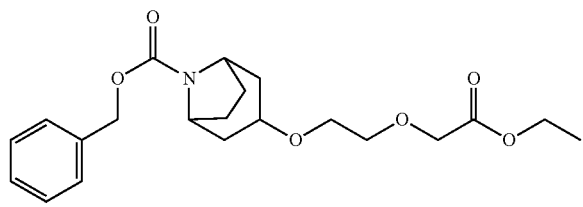

39e

To a solution of benzyl 3-oxo-8-azabicyclo[3.2.1]octane-8-carboxylate (879.6 mg, 3.39 mmol) in DCM (2.0 mL) was added ethyl 2-(2-((trimethylsilyl)oxy)ethoxy)acetate (700.0 mg, 3.39 mmol) and trimethylsilyl trifluoromethanesulfonate (376.99 mg, 1.7 mmol) at −78° C. and the resulting mixture was stirred at −78° C. for 2 hours. Trimethylsilane (433.9 mg, 3.73 mmol) was then added to the mixture at −78° C. and the resulting mixture was stirred at 25° C. for 1 hour. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by column chromatography (PE:EA=20:1) to give benzyl 3-(2-(2-ethoxy-2-oxoethoxy)ethoxy)-8-azabicyclo[3.2.1]octane-8-carboxylate (359 mg, 11.9%) as light yellow oil. MS obsd. (ESI$^+$) [(M+H)$^+$]: 392.1.

Step 6: Preparation of ethyl 2-(2-((8-azabicyclo[3.2.1]octan-3-yl)oxy)ethoxy)acetate

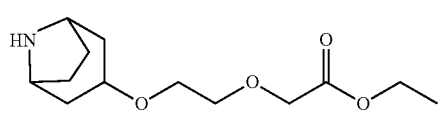

39f

A solution of benzyl 3-(2-(2-ethoxy-2-oxoethoxy)ethoxy)-8-azabicyclo[3.2.1]octane-8-carboxylate (398.0 mg, 1.05 mmol) and Pd/C (113 mg, 0.11 mmol) in EtOH (4.0 mL) was stirred at 25° C. under hydrogen balloon for 12 hours. After the reaction was completed, the mixture was filtered and the liquid was concentrated in vacuo to give ethyl 2-(2-((8-azabicyclo[3.2.1]octan-3-yl)oxy)ethoxy)acetate (169 mg, 65.7%) as light yellow oil, which was used in next step directly without further purification. MS obsd. (ESI$^+$) [(M+H)$^+$]: 258.1.

Step 7: Preparation of ethyl 2-(2-((8-(8-chloro-4-oxo-chromen-2-yl)-8-azabicyclo[3.2.1]octan-3-yl)oxy)ethoxy)acetate

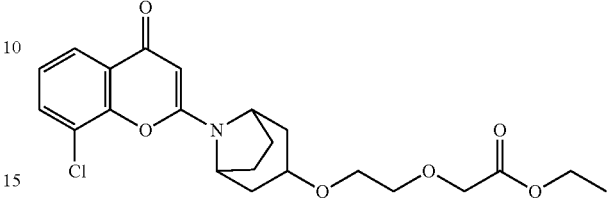

39g

To a solution of 8-chloro-2-(1,2,4-triazol-1-yl)-chromen-4-one (Int-3, 150 mg, 0.61 mmol), ethyl 2-(2-((8-azabicyclo [3.2.1]octan-3-yl)oxy)ethoxy)acetate (171.46 mg, 0.67 mmol) in DMF (5 mL) was added $K_2CO_3$ (251 mg, 1.82 mmol) at room temperature and the resulting mixture was then stirred at 80° C. for 5 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give ethyl 2-(2-((8-(8-chloro-4-oxo-chromen-2-yl)-8-azabicyclo[3.2.1]octan-3-yl)oxy)ethoxy) acetate (70 mg, 16.2%) as a yellow foam. MS obsd. (ESI$^+$) [(M+H)$^+$]: 436.1.

Step 8: Preparation of 2-(2-((8-(8-chloro-4-oxo-chromen-2-yl)-8-azabicyclo[3.2.1]octan-3-yl)oxy)ethoxy)acetic Acid

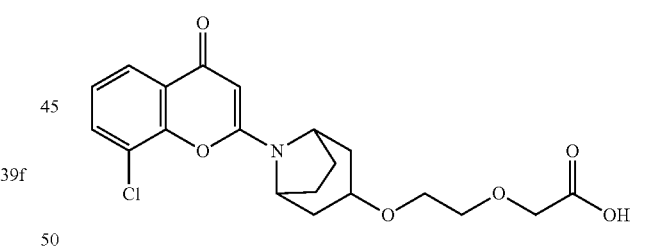

39

To a solution of ethyl 2-(2-((8-(8-chloro-4-oxo-chromen-2-yl)-8-azabicyclo[3.2.1]octan-3-yl)oxy)ethoxy)acetate (70 mg, 160 μmol) in the mixed solvent of THF (10 mL) and $H_2O$ (3 mL) was added LiOH*$H_2O$ (35.0 mg, 0.86 mmol) at room temperature and the resulting mixture was then stirred at room temperature for 12 hours. After the reaction was completed, the mixture was adjusted to pH~4 by addition of 4 N HCl and concentrated in vacuo. The residue was purified by preparative HPLC to give 2-(2-((8-(8-chloro-4-oxo-chromen-2-yl)-8-azabicyclo[3.2.1]octan-3-yl)oxy)ethoxy)acetic acid (40 mg, 61.5%) as a yellow foam. $^1$H NMR (400 MHz, DMSO-$d_6$) δ 12.600 (s, 1H), 7.878-7.794 (m, 2H), 7.385-7.374 (m, 1H), 5.542-5.532 (m, 1H), 4.464-4.462 (m, 2H), 4.083-4.072 (m, 2H), 3.620-3.617 (m, 2H), 3.538-3.536 (m, 3H), 2.230-2.228 (m, 2H), 2.000-1.942 (m, 6H). MS obsd. (ESI$^+$) [(M+H)$^+$]: 408.1.

Example 40

3-[2-[[2-(8-chloro-4-oxo-chromen-2-yl)-1-methyl-3,4-dihydro-1H-isoquinolin-6-yl]oxy]ethoxy]cyclobutanecarboxylic Acid

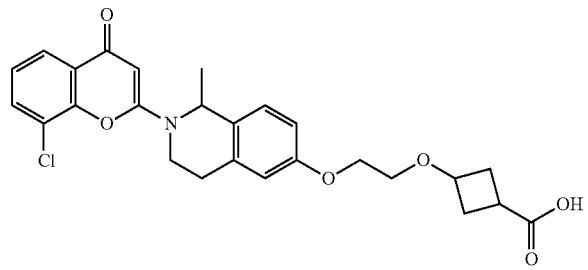

40

Step 1: Preparation of methyl 3-[2-[[2-(8-chloro-4-oxo-chromen-2-yl)-1-methyl-3,4-dihydro-1H-isoquinolin-6-yl]oxy]ethoxy]cyclobutanecarboxylate

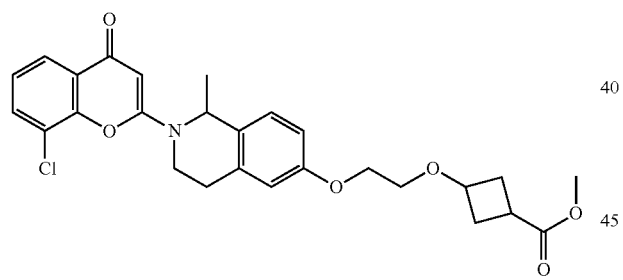

40a

60% NaH (58.5 mg, 1.46 mmol) was added to a solution of 8-chloro-2-(6-hydroxy-1-methyl-3,4-dihydro-1H-isoquinolin-2-yl)chromen-4-one (250 mg, 731 μmol) in DMF (3 mL) at room temperature and the resulting mixture was stirred at room temperature for 30 mins. Methyl 3-[2-(p-tolylsulfonyloxy)ethoxy]cyclobutanecarboxylate (Int-8, 480 mg, 1.46 mmol) was added and the resulting mixture was stirred at 50° C. for 2 hours. After the reaction was completed, the mixture was filtered and concentrated in vacuo to give methyl 3-[2-[[2-(8-chloro-4-oxo-chromen-2-yl)-1-methyl-3,4-dihydro-1H-isoquinolin-6-yl]oxy]ethoxy]cyclobutanecarboxylate (310 mg) as a yellow oil, which was used in next step without further purification.

Step 2: Preparation of 3-[2-[[2-(8-chloro-4-oxo-chromen-2-yl)-1-methyl-3,4-dihydro-1H-isoquinolin-6-yl]oxy]ethoxy]cyclobutanecarboxylic Acid

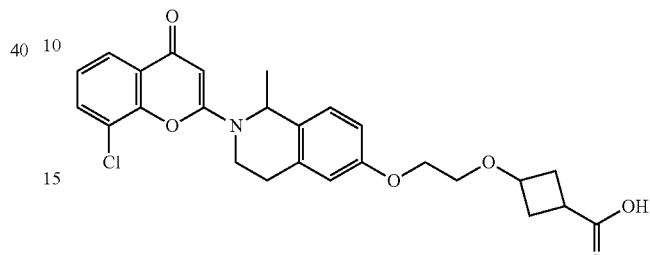

40

A solution of methyl 3-[2-[[2-(8-chloro-4-oxo-chromen-2-yl)-1-methyl-3,4-dihydro-1H-isoquinolin-6-yl]oxy]ethoxy]cyclobutanecarboxylate (100 mg, 201 μmol) and LiOH (24 mg, 1 mmol) in THF (3 mL)/H$_2$O (1 mL) was stirred at room temperature for 2 hours. After the reaction was completed, the mixture was adjusted to pH~4 by addition of 4 N HCl and concentrated in vacuo. The residue was purified by preparative HPLC to give 3-[2-[[2-(8-chloro-4-oxo-chromen-2-yl)-1-methyl-3,4-dihydro-1H-isoquinolin-6-yl]oxy]ethoxy]cyclobutanecarboxylic acid (38 mg, 39%) as a white solid. $^1$H NMR (DMSO-76, 400 MHz): δ ppm 12.15 (br s, 1H), 7.87 (dd, J=7.8, 1.6 Hz, 1H), 7.82 (dd, J=7.9, 1.5 Hz, 1H), 7.39 (t, J=7.8 Hz, 1H), 7.19 (d, J=8.3 Hz, 1H), 6.82 (s, 1H), 6.83 (d, J=10.1 Hz, 1H), 5.64 (s, 1H), 5.27 (br d, J=6.5 Hz, 1H), 4.15 (quin, J=6.7 Hz, 1H), 3.89-4.08 (m, 3H), 3.47-3.67 (m, 3H), 2.96 (t, J=5.9 Hz, 2H), 2.53-2.76 (m, 1H), 2.32-2.46 (m, 2H), 2.10-2.18 (m, 1H), 1.93-2.02 (m, 1H), 1.51 (d, J=6.6 Hz, 3H). MS obsd. (ESI$^+$) [(M+H)$^+$]: 484.

Example 41

Methyl 3-(((8-(8-chloro-4-oxo-chromen-2-yl)-8-azabicyclo[3.2.1]octan-3-yl)oxy)methyl)benzoate

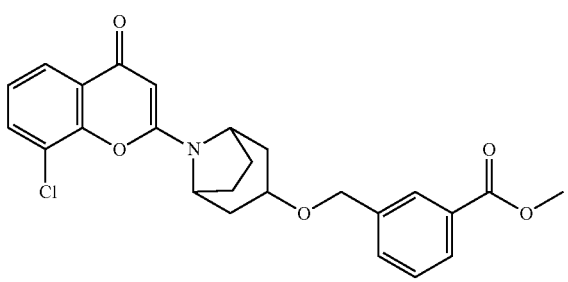

41

Step 1: Preparation of tert-butyl 3-((3-(methoxycarbonyl)benzyl)oxy)-8-azabicyclo[3.2.1]octane-8-carboxylate

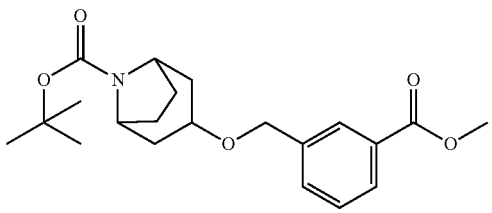

41a

To a solution of tert-butyl 3-hydroxy-8-azabicyclo[3.2.1]octane-8-carboxylate (1.0 g, 4.4 mmol) in DMF (10 mL) was added 60% sodium hydride (879.81 mg, 22 mmol) at 0° C. and the resulting mixture was stirred at 0° C. for 30 mins. Methyl 3-(chloromethyl)benzoate (974.68 mg, 5.28 mmol) was then added to the mixture at 0° C. and the resulting mixture was stirred at 25° C. for 2 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by column chromatography on silica (PE/Ethyl acetate=20:1-5:1) to give tert-butyl 3-((3-(methoxycarbonyl)benzyl)oxy)-8-azabicyclo[3.2.1]octane-8-carboxylate (800 mg, 48.4%) as light yellow oil. MS obsd. (ESI$^+$) [(M+H)$^+$]: 376.1&320.1.

Step 2: Preparation of methyl 3-(((8-azabicyclo[3.2.1]octan-3-yl)oxy)methyl)benzoate

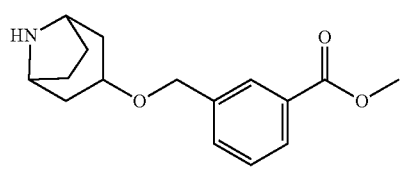

41b

A solution of tert-butyl 3-((3-(methoxycarbonyl)benzyl)oxy)-8-azabicyclo[3.2.1]octane-8-carboxylate (800 mg, 2.13 mmol) in dioxane (4 M HCl solution in Dioxane, 4 mL, 16 mmol) was stirred at 25° C. for 12 hours. After the reaction was completed, the mixture was concentrated in vacuo to give methyl 3-(((8-azabicyclo[3.2.1]octan-3-yl)oxy)methyl)benzoate (600 mg, quant.) as a white solid, which was used in next step without further purification. MS obsd. (ESI$^+$) [(M+H)$^+$]: 276.1.

Step 3: Preparation of methyl 3-(((8-(8-chloro-4-oxo-chromen-2-yl)-8-azabicyclo[3.2.1]octan-3-yl)oxy)methyl)benzoate

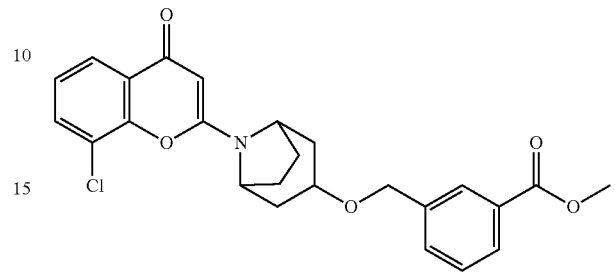

41

To a solution of 8-chloro-2-(1,2,4-triazol-1-yl)-chromen-4-one (Int-3, 431 mg, 1.74 mmol), methyl 3-(((8-azabicyclo[3.2.1]octan-3-yl)oxy)methyl)benzoate (400 mg, 1.45 mmol) in DMF (5 mL) was added $K_2CO_3$ (602.3 mg, 4.36 mmol) at room temperature and the resulting mixture was then stirred at 80° C. for 5 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give methyl 3-(((8-(8-chloro-4-oxo-chromen-2-yl)-8-azabicyclo[3.2.1]octan-3-yl)oxy)methyl)benzoate (20 mg, 3.2%) as a white foam. $^1$H NMR (400 MHz, DMSO-$d_6$) δ 7.96-7.87 (m, 3H), 7.82 (dd, 7=1.5, 7.9 Hz, 1H), 7.66-7.61 (m, 1H), 7.60-7.54 (m, 1H), 7.39 (t, 7=7.9 Hz, 1H), 5.60 (s, 1H), 5.26 (br s, 1H), 4.57 (br s, 2H), 4.52 (s, 2H), 3.34 (s, 3H), 2.36-2.31 (m, 2H), 2.31-2.24 (m, 2H), 2.21-2.12 (m, 2H), 1.95 (br d, 7=15.2 Hz, 2H). MS obsd. (ESI$^+$) [(M+H)$^+$]: 454.1.

Example 42

8-chloro-3-iodo-2-((4-methoxybenzyl)amino)-chromen-4-one

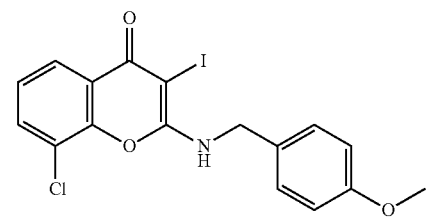

42

To a solution of 8-chloro-3-iodo-2-(1,2,4-triazol-1-yl)-chromen-4-one (Int-4, 187 mg, 500 μmol), (4-methoxyphenyl)methanamine (137 mg, 1 mmol) in DMF (5 mL) was added $K_2CO_3$ (143 mg, 1.03 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-3-iodo-2-((4-methoxybenzyl)amino)-chromen-4-one (10 mg, 4.5%) as a yellow foam. $^1$H NMR (400 MHz, DMSO-$d_6$) δ 8.30-8.43 (m, 1H), 7.86-7.95 (m, 1H), 7.78-7.86 (m, 1H), 7.33-7.43 (m, 3H), 6.87-6.94 (m, 2H), 4.55-4.64 (m, 2H), 3.74 (s, 3H). MS obsd. (ESI$^+$) [(M+H)$^+$]: 442.1.

Example 43

2-(8-chloro-4-oxo-chromen-2-yl)-5-methoxyisoindolin-1-one

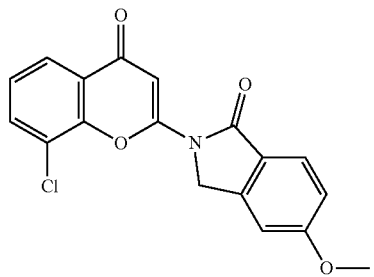

43

To a solution of 8-chloro-2-(1,2,4-triazol-1-yl)-chromen-4-one (Int-3, 700 mg, 2.83 mmol), 5-methoxyisoindolin-1-one (553 mg, 3.39 mmol) in DMF (10 mL) was added $K_2CO_3$ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 2-(8-chloro-4-oxo-chromen-2-yl)-5-methoxyisoindolin-1-one (200 mg, 20.7%) as a yellow foam. $^1$H NMR (400 MHz, DMSO-$d_6$) δ 7.95-8.02 (m, 2H), 7.78-7.84 (m, 1H), 7.47-7.54 (m, 1H), 7.36-7.41 (m, 1H), 7.12-7.18 (m, 2H), 5.21 (s, 2H), 3.94 (s, 3H). MS obsd. (ESI$^+$) [(M+H)$^+$]: 342.1.

Example 44

2-(8-chloro-4-oxo-chromen-2-yl)-6-methoxy-3,4-dihydroisoquinolin-1-one

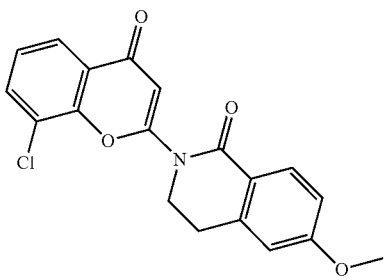

44

To a solution of 8-chloro-2-(1,2,4-triazol-1-yl)-chromen-4-one (Int-3, 800 mg, 3.23 mmol), 6-methoxy-3,4-dihydroisoquinolin-1-one (687 mg, 3.88 mmol) in DMF (10 mL) was added $K_2CO_3$ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 2-(8-chloro-4-oxo-chromen-2-yl)-6-methoxy-3,4-dihydroisoquinolin-1-one (200 mg, 17.4%) as a yellow foam. $^1$H NMR (400 MHz, DMSO-$d_6$) δ 7.93-8.03 (m, 3H), 7.46-7.58 (m, 1H), 6.94-7.04 (m, 2H), 6.77-6.81 (m, 1H), 4.19-4.28 (m, 2H), 3.86 (s, 3H), 3.13-3.20 (m, 2H). MS obsd. (ESI$^+$) [(M+H)$^+$]: 356.1.

Example 45

8-chloro-6-fluoro-2-(4-phenylpiperazin-1-yl)-chromen-4-one

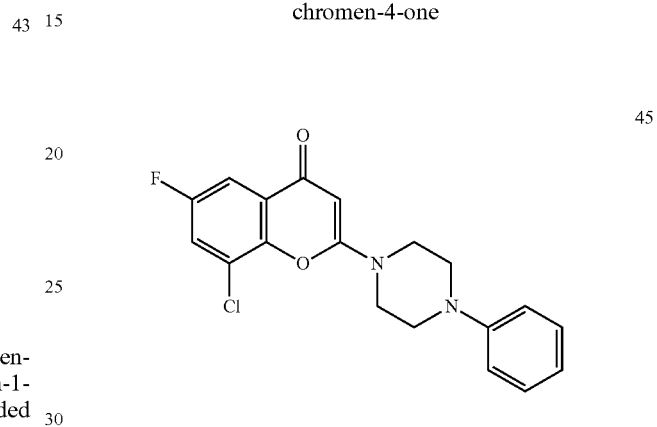

45

To a solution of 8-chloro-6-fluoro-2-(1,2,4-triazol-1-yl)-chromen-4-one (Int-6, 300 mg, 1.14 mmol), 1-phenylpiperazine (916 mg, 5.65 mmol) in DMF (5 mL) was added $K_2CO_3$ (602.3 mg, 4.36 mmol) at room temperature and the resulting mixture was then stirred at 80° C. for 5 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-6-fluoro-2-(4-phenylpiperazin-1-yl)-chromen-4-one (36 mg, 8.58%) as a yellow foam. $^1$H NMR (400 MHz, DMSO-$d_6$) δ 7.92 (dd, $J$=8.16, 3.01 Hz, 1H), 7.60 (dd, $J$=8.16, 3.14 Hz, 1H), 7.26 (t, $J$=7.97 Hz, 2H), 7.01 (d, $J$=8.03 Hz, 2H), 6.84 (t, $J$=7.05 Hz, 1H), 5.69 (s, 1H), 3.71-3.79 (m, 4H), 2.52-2.56 (m, 4H). MS obsd. (ESI$^+$) [(M+H)$^+$]: 359.1.

Example 46

4-benzyloxy-1-(8-chloro-3-iodo-4-oxo-chromen-2-yl)pyridin-2-one

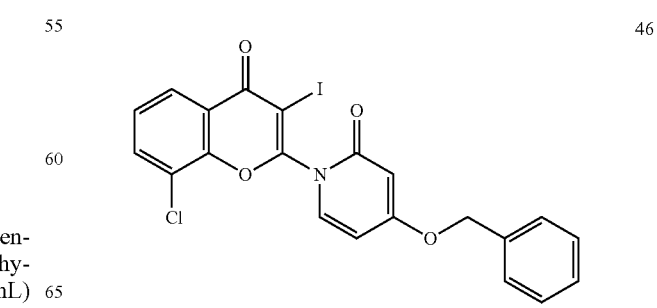

46

To a solution of 8-chloro-3-iodo-2-(1,2,4-triazol-1-yl)-chromen-4-one (Int-4, 187 mg, 500 μmol), 4-(benzyloxy)pyridin-2-one (150 mg, 0.746 mmol) in DMF (5 mL) was added K$_2$CO$_3$ (143 mg, 1.03 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 4-benzyloxy-1-(8-chloro-3-iodo-4-oxo-chromen-2-yl)pyridin-2-one (12 mg, 4.8%) as a yellow foam. $^1$H NMR (400 MHz, DMSO-d$_6$) δ 8.07-8.13 (m, 2H), 7.74-7.79 (m, 1H), 7.58-7.65 (m, 1H), 7.36-7.52 (m, 5H), 6.31-6.38 (m, 1H), 6.07-6.14 (m, 1H), 5.21 (s, 2H). MS obsd. (ESI$^+$) [(M+H)$^+$]: 506.1.

Example 47

8-chloro-2-(6-hydroxy-2-azaspiro[3.3]heptan-2-yl)chromen-4-one

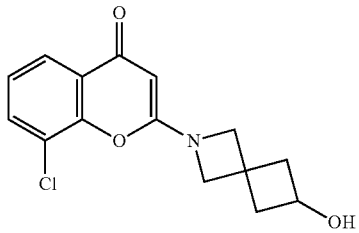

47

A solution of 8-chloro-2-(1,2,4-triazol-4-yl)-chromen-4-one (116 mg, 0.47 mmol), 2-azaspiro[3.3]heptan-6-ol (53 mg, 0.47 mmol) and K$_2$CO$_3$ (193 mg, 1.41 mmol) in DMF (10 mL) was stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-2-(6-hydroxy-2-azaspiro[3.3]heptan-2-yl)-chromen-4-one (50 mg, 36.6%) as yellow solid/H NMR (DMSO-76, 400 MHz): δ 7.79 (dd, 7=1.47, 7.83 Hz, 1H), 7.71 (dd, 7=1.34, 7.83 Hz, 1H), 7.29 (t, 7=7.83 Hz, 1H), 5.03 (d, 7=5.99 Hz, 1H), 4.97-5.00 (m, 1H), 4.08 (s, 2H), 4.02 (s, 2H), 3.89-3.99 (m, 1H), 2.47 (mm, 2H), 1.93-2.02 (m, 2H). MS obsd. (ESI+) [(M+H)+]: 292.0.

Example 48

8-chloro-2-((4-methoxybenzyl)(methyl)amino)-chromen-4-one

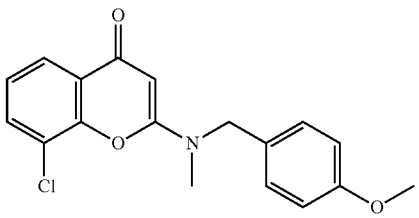

48

To a solution of 8-chloro-2-(1,2,4-triazol-1-yl)-chromen-4-one (Int-3, 700 mg, 2.83 mmol), 1-(4-methoxyphenyl)-N-methylmethanamine (513 mg, 3.39 mmol) in DMF (5 mL) was added K$_2$CO$_3$ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-2-((4-methoxybenzyl)(methyl)amino)-chromen-4-one (600 mg, 64.4%) as a yellow foam. $^1$H NMR (400 MHz, DMSO-d$_6$) δ 7.85-7.92 (m, 1H), 7.77-7.85 (m, 1H), 7.35-7.45 (m, 1H), 7.26-7.34 (m, 2H), 6.89-6.98 (m, 2H), 5.39-5.45 (m, 1H), 4.74 (s, 2H), 3.73 (s, 3H), 3.14 (s, 3H). MS obsd. (ESI$^+$) [(M+H)$^+$]: 330.1.

Example 49

8-chloro-6-fluoro-2-(4-phenylpiperidin-1-yl)-chromen-4-one

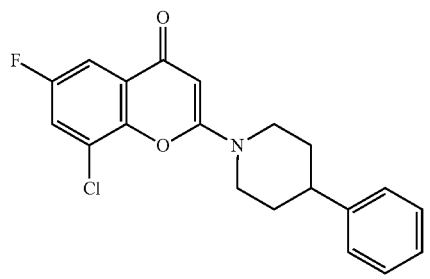

49

To a solution of 8-chloro-6-fluoro-2-(1,2,4-triazol-1-yl)-chromen-4-one (Int-6, 300 mg, 1.14 mmol), 4-phenylpiperidine (910 mg, 5.65 mmol) in DMF (5 mL) was added K$_2$CO$_3$ (602.3 mg, 4.36 mmol) at room temperature and the resulting mixture was then stirred at 80° C. for 5 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-6-fluoro-2-(4-phenylpiperidin-1-yl)-chromen-4-one (31 mg, 7.65%) as a yellow foam. $^1$H NMR (400 MHz, DMSO-d$_6$) δ 7.90 (dd, 7=8.16, 3.01 Hz, 1H), 7.59 (dd, 7=8.22, 3.07 Hz, 1H), 7.26-7.34 (m, 4H), 7.21 (s, 1H), 5.68 (s, 1H), 4.28 (br d, 7=13.55 Hz, 2H), 3.02-3.17 (m, 2H), 2.84-2.94 (m, 1H), 1.92 (br d, 7=11.04 Hz, 2H), 1.76 (br d, 7=3.76 Hz, 2H). MS obsd. (ESI$^+$) [(M+H)$^+$]: 358.1.

Example 50

3-(2-(4-(1-(8-chloro-6-fluoro-4-oxo-chromen-2-yl)piperidin-4-yl)phenoxy)ethoxy)cyclobutane-1-carboxylic Acid

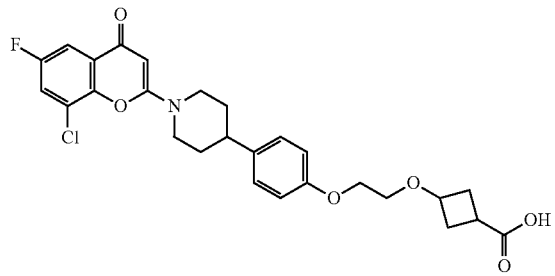

Step 1: Preparation of tert-butyl 4-(4-hydroxyphenyl)piperidine-1-carboxylate

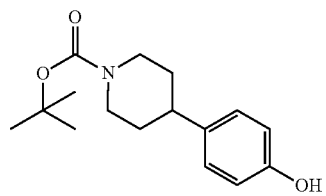

50a

To a solution of 4-(piperidin-4-yl)phenol (2 g, 11.28 mmol), triethylamine (2.36 mL, 16.93 mmol) in DCM (20 mL) was added di-t-butyldicarbonate (3 g, 13.54 mmol) at 10° C. and the resulting mixture was then stirred at 10° C. for 15 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo to give tert-butyl 4-(4-hydroxyphenyl)piperidine-1-carboxylate (2.5 g, 78.1%) as a white solid, which was used in next step directly without further purification. MS obsd. (ESI$^+$) [(M+H)$^+$]: 278.1.

Step 2: Preparation of tert-butyl 4-(4-(2-(3-(methoxycarbonyl)cyclobutoxy)ethoxy)phenyl)piperidine-1-carboxylate

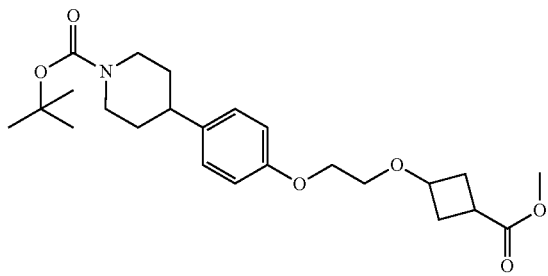

50b

To a solution of tert-butyl 4-(4-hydroxyphenyl)piperidine-1-carboxylate (330 mg, 1.19 mmol), methyl 3-[2-(p-tolylsulfonyloxy)ethoxy]cyclobutanecarboxylate (Int-8, 560 mg, 1.71 mmol) in DMF (5 mL) was added $K_2CO_3$ (700 mg, 5.06 mmol) at room temperature and the resulting mixture was then stirred at 70° C. for 12 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo to give tert-butyl 4-(4-(2-(3-(methoxycarbonyl)cyclobutoxy)ethoxy)phenyl)piperidine-1-carboxylate (350 mg, 20.3%) as a yellow oil, which was used in next step directly without further purification. MS obsd. (ESI$^+$) [(M+H)$^+$]: 434.1.

Step 3: Preparation of methyl 3-(2-(4-(piperidin-4-yl)phenoxy)ethoxy)cyclobutane-1-carboxylate

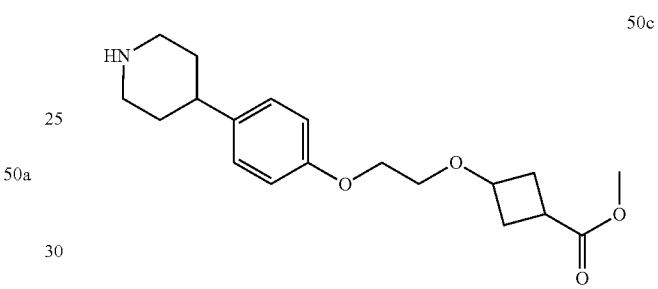

50c

A solution of tert-butyl 4-(4-(2-(3-(methoxycarbonyl)cyclobutoxy)ethoxy)phenyl)piperidine-1-carboxylate (700 mg, 1.61 mmol) in dioxane (4 M HCl solution in Dioxane, 10 mL, 40 mmol) was stirred at 25° C. for 12 hours. After the reaction was completed, the mixture was concentrated in vacuo to give methyl 3-(2-(4-(piperidin-4-yl)phenoxy)ethoxy)cyclobutane-1-carboxylate (150 mg, 25%) as a colorless oil. MS obsd. (ESI$^+$) [(M+H)$^+$]: 334.1.

Step 4: Preparation of methyl 3-(2-(4-(1-(8-chloro-6-fluoro-4-oxo-chromen-2-yl)piperidin-4-yl)phenoxy)ethoxy)cyclobutane-1-carboxylate

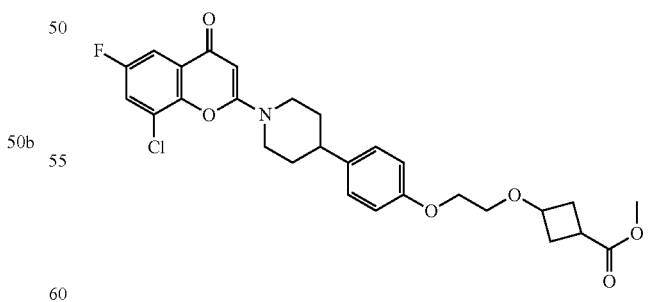

50d

To a solution of 8-chloro-6-fluoro-2-(1,2,4-triazol-1-yl)-chromen-4-one (Int-6, 179.3 mg, 0.67 mmol), methyl 3-(2-(4-(piperidin-4-yl)phenoxy)ethoxy)cyclobutane-1-carboxylate (150 mg, 0.45 mmol) in DMF (5 mL) was added $K_2CO_3$ (124 mg, 0.9 mmol) at room temperature and the resulting mixture was then stirred at 80° C. for 5 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo to give methyl 3-(2-(4-(1-(8-chloro-6-fluoro-4-oxo-chromen-2-yl)piperidin-4-yl)phenoxy)ethoxy)cyclobutane-1-carboxylate (238 mg, quant.) as a yellow foam, which was used in next step directly without further purification. MS obsd. (ESI$^+$) [(M+H)$^+$]: 530.1.

Step 5: Preparation of 3-(2-(4-(1-(8-chloro-6-fluoro-4-oxo-chromen-2-yl)piperidin-4-yl)phenoxy)ethoxy)cyclobutane-1-carboxylic Acid

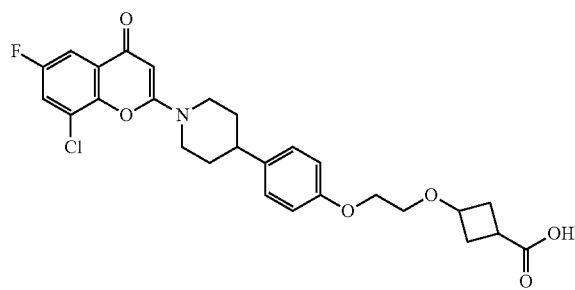

50

To a solution of methyl 3-(2-(4-(1-(8-chloro-6-fluoro-4-oxo-chromen-2-yl)piperidin-4-yl)phenoxy)ethoxy)cyclobutane-1-carboxylate (238 mg, 0.45 mmol) in the mixed solvent of THF (10 mL) and $H_2O$ (3 mL) was added LiOH*$H_2O$ (35.0 mg, 0.86 mmol) at room temperature and the resulting mixture was then stirred at room temperature for 12 hours. After the reaction was completed, the mixture was adjusted to pH~4 by addition of 4 N HCl and then concentrated in vacuo. The residue was purified by preparative HPLC to give 3-(2-(4-(1-(8-chloro-6-fluoro-4-oxo-chromen-2-yl)piperidin-4-yl)phenoxy)ethoxy)cyclobutane-1-carboxylic acid (18 mg, 7.5%) as a yellow foam. $^1$H NMR (400 MHz, DMSO-d$_6$) δ 12.30 (s, 1H), 7.91 (dd, J=3.0, 8.2 Hz, 1H), 7.59 (dd, J=3.0, 8.2 Hz, 1H), 7.19 (d, J=8.7 Hz, 2H), 6.87 (d, J=8.7 Hz, 2H), 5.68 (s, 1H), 4.26 (br d, J=13.4 Hz, 2H), 4.15-3.8 (m, 3H), 3.65-3.58 (m, 2H), 3.25-3.12 (m, 2H), 2.96-2.56 (m, 2H), 2.45-2.35 (m, 2H), 2.20-2.09 (m, 1H), 2.02-1.92 (m, 1H), 1.88 (br d, J=11.2 Hz, 2H), 1.75-1.62 (m, 2H). MS obsd. (ESI$^+$) [(M+H)$^+$]: 516.1.

Example 51

8-chloro-2-(3-hydroxy-8-azabicyclo[3.2.1]octan-8-yl)-chromen-4-one

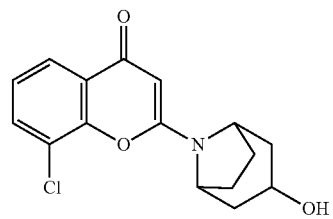

51

Step 1: Preparation of 8-azabicyclo[3.2.1]octan-3-ol

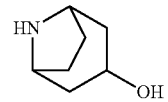

51a

A solution of tert-butyl 3-hydroxy-8-azabicyclo[3.2.1]octane-8-carboxylate (322 mg, 1.41 mmol) in dioxane (4 M HCl solution in Dioxane, 3 mL, 12 mmol) was stirred at 25° C. for 12 hours. After the reaction was completed, the mixture was concentrated in vacuo to give 8-azabicyclo[3.2.1]octan-3-ol (180 mg, quant.) as a white solid. MS obsd. (ESI$^+$) [(M+H)$^+$]: 128.1.

Step 2: Preparation of 8-chloro-2-(3-hydroxy-8-azabicyclo[3.2.1]octan-8-yl)-chromen-4-one

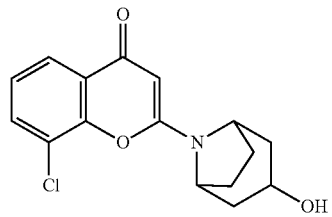

51

To a solution of 8-chloro-2-(1,2,4-triazol-1-yl)-chromen-4-one (Int-3, 385.5 mg, 1.56 mmol), 8-azabicyclo[3.2.1]octan-3-ol (180 mg, 1.42 mmol) in DMF (5 mL) was added $K_2CO_3$ (781 mg, 5.65 mmol) at room temperature and the resulting mixture was then stirred at 80° C. for 12 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-2-(3-hydroxy-8-azabicyclo[3.2.1]octan-8-yl)-chromen-4-one (40 mg, 9.2%) as a white foam. $^1$H NMR (400 MHz, DMSO-d$_6$) δ 7.874-7.871 (m, 1H), 7.855-7.851 (m, 1H), 7.386-7.347 (m, 1H), 5.538 (s, 1H), 4.465-4.458 (m, 2H), 3.934-3.924 (m, 1H), 2.401-2.331 (m, 2H), 2.080-1.974 (m, 5H), 1.783-1.747 (m, 2H). MS obsd. (ESI$^+$) [(M+H)$^+$]: 306.1.

Example 52

8-chloro-2-((4-methoxybenzyl)amino)-chromen-4-one

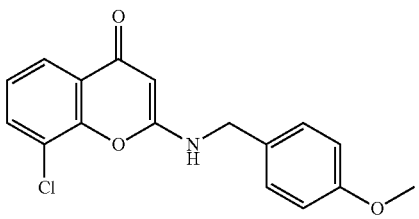

52

To a solution of 8-chloro-2-(1,2,4-triazol-1-yl)-chromen-4-one (Int-3, 600 mg, 2.42 mmol), (4-methoxyphenyl)methanamine (399 mg, 2.91 mmol) in DMF (5 mL) was added K$_2$CO$_3$ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 8-chloro-2-((4-methoxybenzyl)amino)-chromen-4-one (400 mg, 52.3%) as a yellow foam. $^1$H NMR (400 MHz, DMSO-d$_6$) δ 8.68-8.75 (m, 1H), 7.81-7.88 (m, 1H), 7.73-7.81 (m, 1H), 7.28-7.41 (m, 3H), 6.87-6.99 (m, 2H), 5.20-5.31 (m, 1H), 4.30-4.45 (m, 2H), 3.73 (s, 3H). MS obsd. (ESI$^+$) [(M+H)$^+$]: 316.1.

Example 53

Methyl 3-(4-(8-chloro-4-oxo-chromen-2-yl)piperazin-1-yl)benzoate

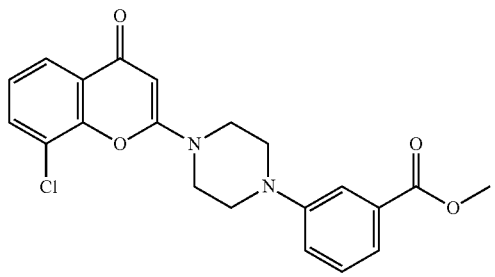

53

Step 1: Preparation of methyl 3-bromobenzoate

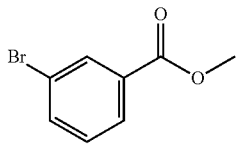

53a

To a solution of 3-bromobenzoic acid (1.0 g, 5.0 mmol) in MeOH (20 mL) was added SOCl$_2$ (5 mL) at room temperature and the resulting mixture was then stirred at 90° C. for 3 hours. After the reaction was completed, the mixture was concentrated in vacuo to give methyl 3-bromobenzoate (1.1 g, quant.) as a colorless oil, which was used in next step directly without further purification. MS obsd. (ESI$^+$) [(M+H)$^+$]: 215.1&217.1.

Step 2: Preparation of methyl 3-(4-acetylpiperazin-1-yl)benzoate

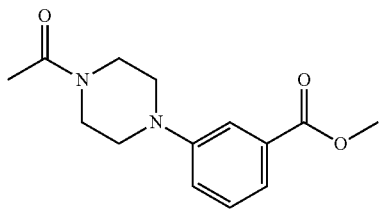

53b

To a solution of methyl 3-bromobenzoate (1.1 g, 5 mmol) and 1-(piperazin-1-yl)ethan-1-one (0.64 g, 5 mmol) in toluene (20 mL) was added Pd(OAc)$_2$ (0.12 g, 0.500 mmol), Xantphos (0.58 g, 1.000 mmol) and Cs$_2$CO$_3$ (2.45 g, 7.502 mmol) at 25° C. and the resulting mixture was then stirred at 100° C. for 16 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by column chromatography on silica (PE/Ethyl acetate=1:1-1:3) to give methyl 3-(4-acetylpiperazin-1-yl)benzoate (1.2 g, 90.9%) as light yellow oil. MS obsd. (ESI$^+$) [(M+H)$^+$]: 263.1.

Step 3: Preparation of methyl 3-(4-(8-chloro-4-oxo-chromen-2-yl)piperazin-1-yl)benzoate

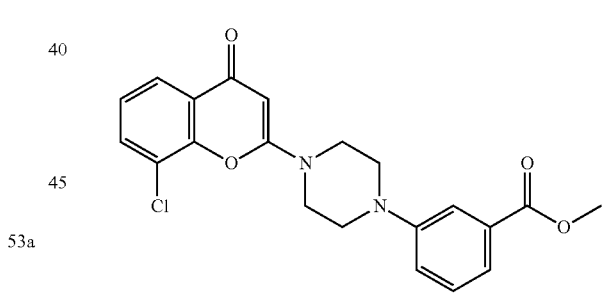

53

To a solution of methyl 3-(4-acetylpiperazin-1-yl)benzoate (300 mg, 1.14 mmol) in DCE (10.0 mL) was added POCl$_3$ (380 mg, 2.5 mmol) at 0° C. and the resulting mixture was then stirred at 25° C. for 2 hours. 3-chloro-2-hydroxybenzoic acid (240 mg, 1.37 mmol) was added to the mixture at 0° C. and then the resulting mixture was stirred at 80° C. for 14 hours. After the reaction was completed, the mixture was concentrated in vacuo. The residue was dissolved in DCE (20.0 mL) and NaOAc (1.31 g, 16.0 mmol) was added to the solution. The resulting mixture was stirred at 80° C. for 24 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give methyl 3-(4-(8-chloro-4-oxo-chromen-2-yl)piperazin-1-yl)benzoate (7 mg, 1.6%) as a yellow foam. $^1$H NMR (400 MHz, DMSO-d$_6$) δ 7.891-7.871 (d, 7=8.0 Hz, 1H), 7.838-7.818 (m, 1H), 7.514 (s, 1H), 7.435-7.375 (m, 3H), 7.315 (s, 1H), 5.647 (s, 1H), 3.848 (s, 3H), 3.769-3.745 (m, 4H), 3.399 (s, 4H). MS obsd. (ESI$^+$) [(M+H)$^+$]: 399.1.

Example 54

Methyl 3-(2-((2-(8-chloro-4-oxo-chromen-2-yl)-3-oxoisoindolin-5-yl)oxy)ethoxy)cyclobutanecarboxylate

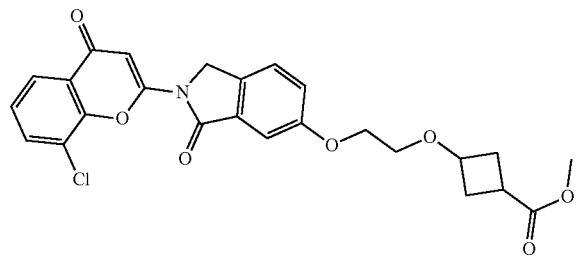

54

Step 1: Preparation of 2-(8-chloro-4-oxo-chromen-2-yl)-6-hydroxyisoindolin-1-one

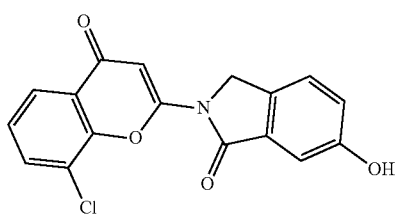

54a

To a solution of 2-(8-chloro-4-oxo-chromen-2-yl)-6-methoxyisoindolin-1-one (150 mg, 439 μmol) in DCM (5 mL) was added BBr$_3$ (1 M solution in DCM, 10 mL, 10 mmol) at room temperature and the resulting mixture was then stirred at room temperature overnight. After the reaction was completed, the mixture was concentrated in vacuo and the residue was suspended in saturated NH$_4$Cl solution (30 mL). The solid was collected by filtration and dried in vacuo to give 2-(8-chloro-4-oxo-chromen-2-yl)-6-hydroxyisoindolin-1-one (130 mg, 90.4%) as a yellow solid, which was used in the next step directly without further purification. MS obsd. (ESI$^+$) [(M+H)$^+$]: 328.1.

Step 2: Preparation of methyl 3-(2-((2-(8-chloro-4-oxo-chromen-2-yl)-3-oxoisoindolin-5-yl)oxy)ethoxy)cyclobutanecarboxylate

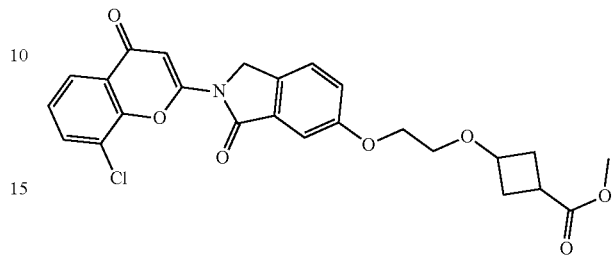

54

To a solution of 2-(8-chloro-4-oxo-chromen-2-yl)-6-hydroxyisoindolin-1-one (160 mg, 488 μmol), methyl 3-[2-(p-tolylsulfonyloxy)ethoxy]cyclobutanecarboxylate (Int-8, 240 mg, 732 μmol) in DMF (5 mL) was added K$_2$CO$_3$ (118 mg, 857 μmol) at room temperature and the resulting mixture was then stirred at 60° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give methyl 3-(2-((2-(8-chloro-4-oxo-chromen-2-yl)-3-oxoisoindolin-5-yl)oxy)ethoxy)cyclobutanecarboxylate (100 mg, 42.3%) as a white foam. $^1$H NMR (400 MHz, DMSO-d$_6$) δ 7.95-8.04 (m, 2H), 7.67-7.75 (m, 1H), 7.47-7.57 (m, 1H), 7.33-7.41 (m, 2H), 7.18 (s, 1H), 5.11-5.19 (m, 2H), 3.91-4.23 (m, 3H), 3.65-3.70 (m, 2H), 3.58-3.64 (m, 3H), 2.65-3.08 (m, 1H), 2.37-2.46 (m, 2H), 2.14-2.25 (m, 1H), 1.96-2.07 (m, 1H). MS obsd. (ESI$^+$) [(M+H)$^+$]: 484.1.

Example 55

2-(8-chloro-4-oxo-chromen-2-yl)-6-methoxyisoindolin-1-one

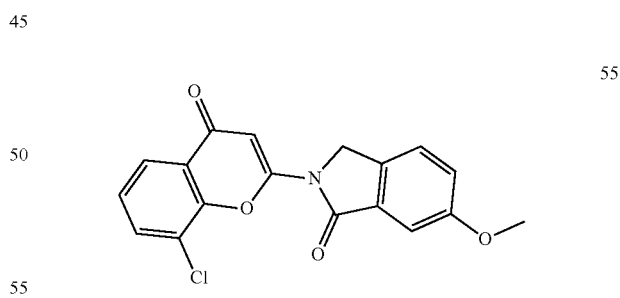

55

To a solution of 8-chloro-2-(1,2,4-triazol-1-yl)-chromen-4-one (Int-3, 700 mg, 2.83 mmol), 6-methoxyisoindolin-1-one (553 mg, 3.39 mmol) in DMF (5 mL) was added K$_2$CO$_3$ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give 2-(8-chloro-4-oxo-chromen-2-yl)-6-methoxyisoindolin-1-one (150 mg, 15.5%) as a yellow foam. ¹H NMR (400 MHz, DMSO-d₆) δ 7.99 (dd, J=1.10, 7.95 Hz, 2H), 7.68-7.80 (m, 1H), 7.47-7.56 (m, 1H), 7.37 (s, 2H), 7.15-7.25 (m, 1H), 5.22 (s, 2H), 3.87 (s, 3H). MS obsd. (ESI⁺) [(M+H)⁺]: 342.1.

Example 56

3-(2-(4-(((8-chloro-4-oxo-chromen-2-yl)(methyl)amino)methyl)phenoxy)ethoxy)cyclobutanecarboxylic acid

56

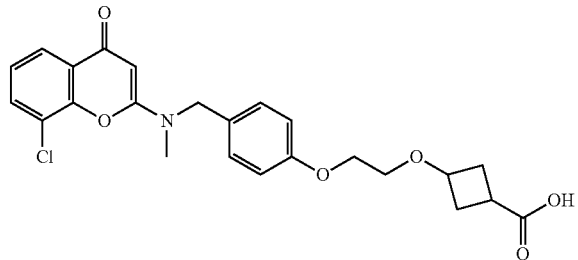

Step 1: Preparation of 8-chloro-2-((4-methoxybenzyl)(methyl)amino)-chromen-4-one Step 2: Preparation of 8-chloro-2-((4-hydroxybenzyl)(methyl)amino)-chromen-4-one 56b

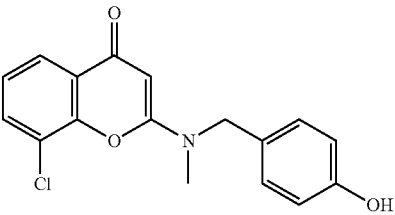

To a solution of 8-chloro-2-((4-methoxybenzyl)(methyl)amino)-chromen-4-one (500 mg, 1.52 mmol) in DCM (5 mL) was added BBr₃ (1 M solution in DCM, 10 mL, 10 mmol) at room temperature and the resulting mixture was then stirred at room temperature overnight. After the reaction was completed, the mixture was concentrated in vacuo and the residue was suspended in saturated NH₄Cl solution (30 mL). The solid was collected by filtration and dried in vacuo to give 8-chloro-2-((4-hydroxybenzyl)(methyl)amino)-chromen-4-one (480 mg, 100%) as a yellow solid, which was used in the next step directly without further purification. MS obsd. (ESI⁺) [(M+H)⁺]: 316.1.

Step 3: Preparation of methyl 3-(2-(4-(((8-chloro-4-oxo-chromen-2-yl)(methyl)amino)methyl)phenoxy)ethoxy)cyclobutanecarboxylate 56a

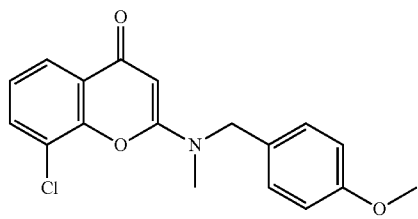

56c

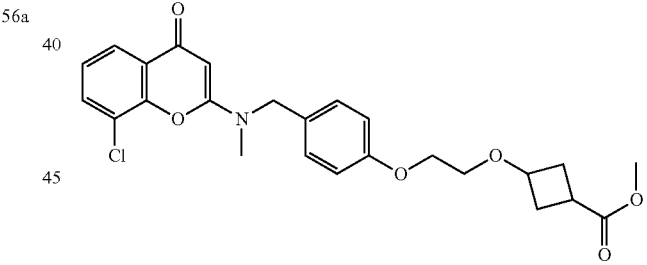

To a solution of 8-chloro-2-(1,2,4-triazol-1-yl)-chromen-4-one (Int-3, 700 mg, 2.83 mmol), 1-(4-methoxyphenyl)-N-methylmethanamine (513 mg, 3.39 mmol) in DMF (5 mL) was added K₂CO₃ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na₂SO₄ and concentrated in vacuo to give 8-chloro-2-((4-methoxybenzyl)(methyl)amino)-chromen-4-one (600 mg, 64.4%) as a yellow foam, which was used in the next step directly without further purification. MS obsd. (ESI⁺) [(M+H)⁺]: 330.1.

To a solution of 8-chloro-2-((4-hydroxybenzyl)(methyl)amino)-chromen-4-one (250 mg, 792 μmol), (1s,3s)-methyl 3-[2-(p-tolylsulfonyloxy)ethoxy]cyclobutanecarboxylate (Int-8, 286 mg, 871 μmol) in DMF (5 mL) was added K₂CO₃ (198 mg, 1.58 mmol) at room temperature and the resulting mixture was then stirred at 60° C. for 12 hours. After the reaction was completed, the mixture was diluted with water (30 mL) and extracted with EtOAc (50 mL) three times. The combined organic layer was washed with brine, dried over anhydrous Na₂SO₄ and concentrated in vacuo to give methyl 3-(2-(4-(((8-chloro-4-oxo-chromen-2-yl)(methyl)amino)methyl)phenoxy)ethoxy)cyclobutanecarboxylate (225 mg, 60.2%) as a yellow foam, which was used in the next step directly without further purification. MS obsd. (ESI⁺) [(M+H)⁺]: 472.1.

Step 4: Preparation of 3-(2-(4-(((8-chloro-4-oxo-chromen-2-yl)(methyl)amino)methyl)phenoxy)ethoxy)cyclobutanecarboxylic Acid

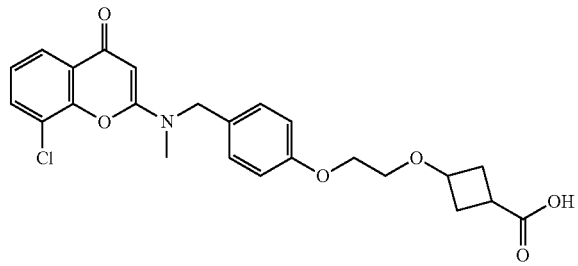

56

To a solution of methyl 3-(2-(4-(((8-chloro-4-oxo-chromen-2-yl)(methyl)amino)methyl)phenoxy)ethoxy)cyclobutanecarboxylate (300 mg, 636 μmol) in the mixed solvent of MeOH (10 mL) and H$_2$O (3 mL) was added LiOH*H$_2$O (70.0 mg, 1.67 mmol) at room temperature and the resulting mixture was then stirred at room temperature for 12 hours. After the reaction was completed, the mixture was adjusted to pH~4 by addition of 4 N HCl and then concentrated in vacuo. The residue was purified by preparative HPLC to give 3-(2-(4-(((8-chloro-4-oxo-chromen-2-yl)(methyl)amino)methyl)phenoxy)ethoxy)cyclobutanecarboxylic acid (124 mg, 42.6%) as a white foam. $^1$H NMR (400 MHz, DMSO-d$_6$) δ 12.09-12.23 (m, 1H), 7.85-7.90 (m, 1H), 7.78-7.83 (m, 1H), 7.34-7.42 (m, 1H), 7.26-7.32 (m, 2H), 6.91-6.97 (m, 2H), 5.39-5.44 (m, 1H), 4.67-4.72 (m, 2H), 3.86-4.18 (m, 3H), 3.56-3.64 (m, 2H), 3.12 (s, 3H), 2.52-2.95 (m, 1H), 2.32-2.47 (m, 2H), 2.08-2.19 (m, 1H), 1.90-2.03 (m, 1H). MS obsd. (ESI$^+$) [(M+H)$^+$]: 458.1.

Example 57

8-chloro-2-(6-hydroxy-1-methyl-3,4-dihydro-1H-isoquinolin-2-yl)chromen-4-one

57

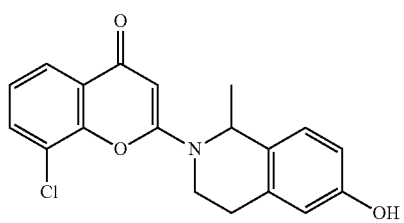

A solution of 8-chloro-2-(1,2,4-triazol-1-yl)chromen-4-one (200 mg, 808 μmol), 1-methyl-1,2,3,4-tetrahydroisoquinolin-6-ol; Hydrobromide (Int-5, 237 mg, 969 μmol) and K$_2$CO$_3$ (246 mg, 1.78 mmol) in DMF (5 mL) was stirred at 100° C. overnight. The mixture was filtered through sintered glass and the filtrate was concentrated in vacuo. The residue was purified by prep-HPLC to give 8-chloro-2-(6-hydroxy-1-methyl-3,4-dihydro-1H-isoquinolin-2-yl)chromen-4-one (112 mg). $^1$H NMR (DMSO-d$_6$, 400 MHz): δ ppm 9.35 (br s, 1H), 7.87 (dd, 7=7.8, 1.6 Hz, 1H), 7.82 (dd, 7=7.9, 1.5 Hz, 1H), 7.38 (t, 7=7.9 Hz, 1H), 7.07 (d, 7=8.4 Hz, 1H), 6.65 (dd, 7=8.3, 2.5 Hz, 1H), 6.60 (d, 7=2.3 Hz, 1H), 5.62 (s, 1H), 5.22 (br d, 7=6.5 Hz, 1H), 3.95 (br s, 1H), 3.48-3.67 (m, 1H), 2.90 (t, 7=5.8 Hz, 2H), 1.49 (d, 7=6.6 Hz, 3H). MS obsd. (ESI$^+$) [(M+H)$^+$]: 342.

Example 58

3-(2-((2-(8-chloro-4-oxo-chromen-2-yl)-1-oxo-1,2,3,4-tetrahydroisoquinolin-6-yl)oxy)ethoxy)cyclobutanecarboxylic Acid

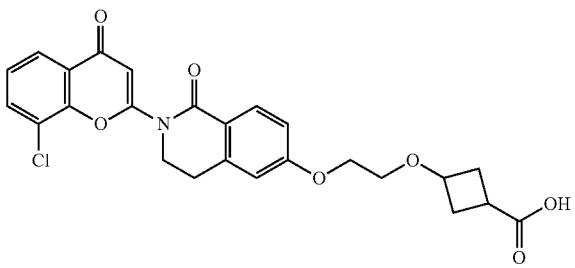

58

Step 1: Preparation of 2-(8-chloro-4-oxo-chromen-2-yl)-6-methoxy-3,4-dihydroisoquinolin-1-one

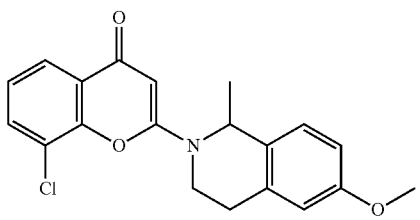

58a

To a solution of 8-chloro-2-(1,2,4-triazol-1-yl)-chromen-4-one (Int-3, 800 mg, 3.23 mmol), 6-methoxy-3,4-dihydroisoquinolin-1-one (687 mg, 3.88 mmol) in DMF (5 mL) was added K$_2$CO$_3$ (781 mg, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give 2-(8-chloro-4-oxo-chromen-2-yl)-6-methoxy-3,4-dihydroisoquinolin-1-one (200 mg, 17.4%) as a yellow foam, which was used in the next step directly without further purification. MS obsd. (ESI$^+$) [(M+H)$^+$]: 356.1.

Step 2: Preparation of 2-(8-chloro-4-oxo-chromen-2-yl)-6-hydroxy-3,4-dihydroisoquinolin-1-one

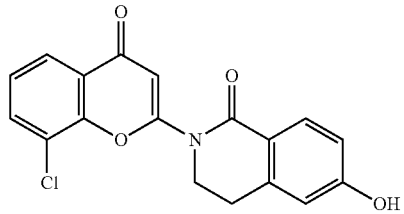

58b

To a solution of 2-(8-chloro-4-oxo-chromen-2-yl)-6-methoxy-3,4-dihydroisoquinolin-1-one (200 mg, 562 μmol) in DCM (5 mL) was added BBr$_3$ (1 M solution in DCM, 5 mL, 5 mmol) at room temperature and the resulting mixture was then stirred at room temperature overnight. After the reaction was completed, the mixture was concentrated in vacuo and the residue was suspended in saturated NH$_4$Cl solution (30 mL). The solid was collected by filtration and dried in vacuo to give 2-(8-chloro-4-oxo-chromen-2-yl)-6-hydroxy-3,4-dihydroisoquinolin-1-one (200 mg, 100%) as a yellow solid, which was used in the next step directly without further purification. MS obsd. (ESI$^+$) [(M+H)$^+$]: 342.1.

Step 3: Preparation of methyl 3-(2-((2-(8-chloro-4-oxo-chromen-2-yl)-1-oxo-1,2,3,4-tetrahydroisoquinolin-6-yl)oxy)ethoxy)cyclobutanecarboxylate

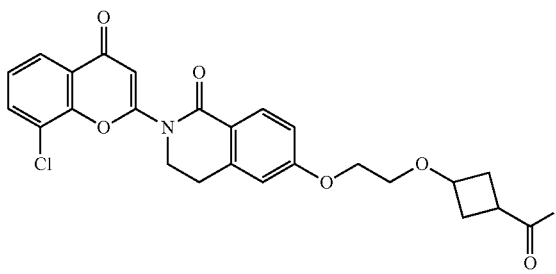

58c

To a solution of 2-(8-chloro-4-oxo-chromen-2-yl)-6-hydroxy-3,4-dihydroisoquinolin-1-one (200 mg, 585 μmol), (1s,3s)-methyl 3-[2-(p-tolylsulfonyloxy)ethoxy]cyclobutanecarboxylate (Int-8, 211 mg, 644 μmol) in DMF (5 mL) was added K$_2$CO$_3$ (198 mg, 1.58 mmol) at room temperature and the resulting mixture was then stirred at 60° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give methyl 3-(2-((2-(8-chloro-4-oxo-chromen-2-yl)-1-oxo-1,2,3,4-tetrahydroisoquinolin-6-yl)oxy)ethoxy)cyclobutanecarboxylate (200 mg, 68.6%) as a yellow foam, which was used in the next step directly without further purification. MS obsd. (ESI$^+$) [(M+H)$^+$]: 498.1.

Step 4: Preparation of 3-(2-((2-(8-chloro-4-oxo-chromen-2-yl)-1-oxo-1,2,3,4-tetrahydroisoquinolin-6-yl)oxy)ethoxy)cyclobutanecarboxylic Acid

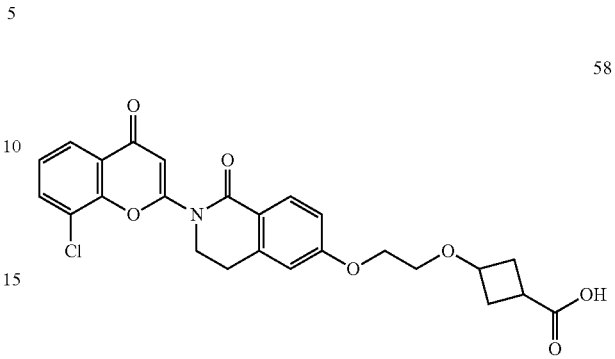

58

To a solution of methyl 3-(2-((2-(8-chloro-4-oxo-chromen-2-yl)-1-oxo-1,2,3,4-tetrahydroisoquinolin-6-yl)oxy)ethoxy)cyclobutanecarboxylate (200 mg, 402 μmol) in the mixed solvent of MeOH (10 mL) and H$_2$O (3 mL) was added LiOH*H$_2$O (70.0 mg, 1.67 mmol) at room temperature and the resulting mixture was then stirred at room temperature for 12 hours. After the reaction was completed, the mixture was adjusted to pH~4 by addition of 4 N HCl and then concentrated in vacuo. The residue was purified by preparative HPLC to give 3-(2-((2-(8-chloro-4-oxo-chromen-2-yl)-1-oxo-1,2,3,4-tetrahydroisoquinolin-6-yl)oxy)ethoxy)cyclobutanecarboxylic acid (10 mg, 5.14%) as a white foam. $^1$H NMR (400 MHz, DMSO-d$_6$) δ 11.95-12.39 (m, 1H), 7.93-8.00 (m, 3H), 7.47-7.53 (m, 1H), 6.97-7.03 (m, 2H), 6.78-6.80 (m, 1H), 3.92-4.26 (m, 5H), 3.64-3.68 (m, 2H), 3.12-3.18 (m, 2H), 2.58-2.96 (m, 1H), 2.35-2.46 (m, 2H), 2.11-2.20 (m, 1H), 1.94-2.04 (m, 1H). MS obsd. (ESI$^+$) [(M+H)$^+$]: 484.1.

Example 59

4-(benzyloxy)-1-(8-chloro-4-oxo-chromen-2-yl)pyridin-2(1H)-one

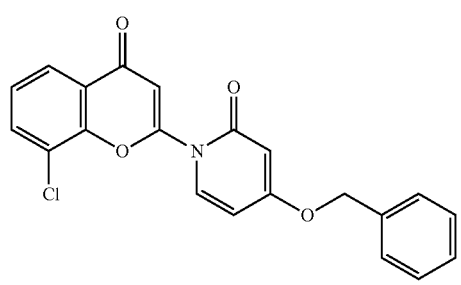

59

To a solution of 8-chloro-2-(1,2,4-triazol-1-yl)-chromen-4-one (Int-3, 700 mg, 2.83 mmol), 4-(benzyloxy)pyridin-2-one (683 mg, 3.39 mmol) in DMF (5 mL) was added Cs$_2$CO$_3$ (1.84 g, 5.65 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo.

The residue was purified by preparative HPLC to give 4-(benzyloxy)-1-(8-chloro-4-oxo-chromen-2-yl)pyridin-2 (1H)-one (630 mg, 58.7%) as a yellow foam. $^1$H NMR (400 MHz, DMSO-d$_6$) δ 8.00-8.10 (m, 2H), 7.80-7.86 (m, 1H), 7.53-7.61 (m, 1H), 7.35-7.51 (m, 5H), 6.80 (s, 1H), 6.26-6.34 (m, 1H), 6.01-6.08 (m, 1H), 5.19 (s, 2H). MS obsd. (ESI$^+$) [(M+H)$^+$]: 380.1.

Example 60

3-(2-(4-(((8-chloro-4-oxo-chromen-2-yl)amino) methyl)phenoxy)ethoxy)cyclobutanecarboxylic Acid

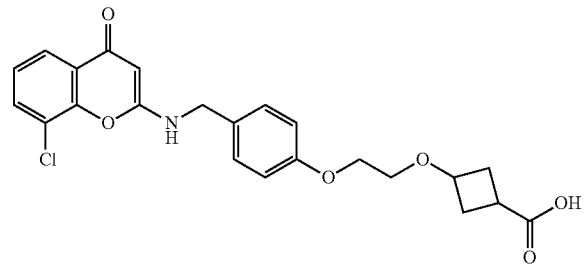

60

Step 1: Preparation of 8-chloro-2-((4-hydroxybenzyl)amino)-chromen-4-one

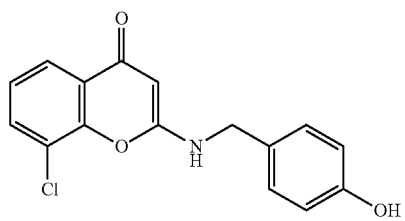

60a

To a solution 8-chloro-2-((4-methoxybenzyl)amino)-chromen-4-one (200 mg, 633 μmol) in DCM (5 mL) was added BBr$_3$ (1 M solution in DCM, 5 mL, 5 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 8-chloro-2-((4-hydroxybenzyl)amino)-chromen-4-one (200 mg, 100%) as a yellow solid, which was used in the next step directly without further purification. MS obsd. (ESI$^+$) [(M+H)$^+$]: 302.1.

Step 2: Preparation of methyl 3-(2-(4-(((8-chloro-4-oxo-chromen-2-yl)amino)methyl)phenoxy)ethoxy) cyclobutanecarboxylate

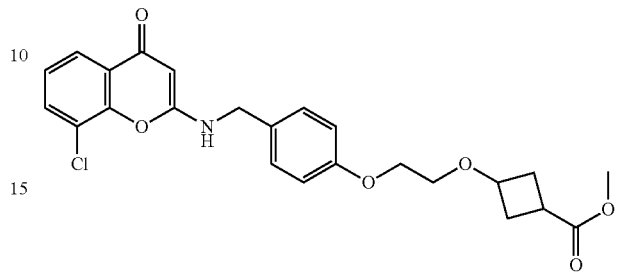

60b

To a solution of 8-chloro-2-((4-hydroxybenzyl)amino)-chromen-4-one (200 mg, 662 μmol), methyl 3-[2-(p-tolylsulfonyloxy)ethoxy]cyclobutanecarboxylate (Int-8, 240 mg, 730 μmol) in DMF (5 mL) was added K$_2$CO$_3$ (198 mg, 1.58 mmol) at room temperature and the resulting mixture was then stirred at 60° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give methyl 3-(2-(4-(((8-chloro-4-oxo-chromen-2-yl)amino)methyl)phenoxy) ethoxy)cyclobutanecarboxylate (210 mg, 69%) as a yellow foam, which was used in the next step directly without further purification. MS obsd. (ESI$^+$) [(M+H)$^+$]: 458.1.

Step 3: Preparation of 3-(2-(4-(((8-chloro-4-oxo-chromen-2-yl)amino)methyl)phenoxy)ethoxy)cy-clobutanecarboxylic Acid

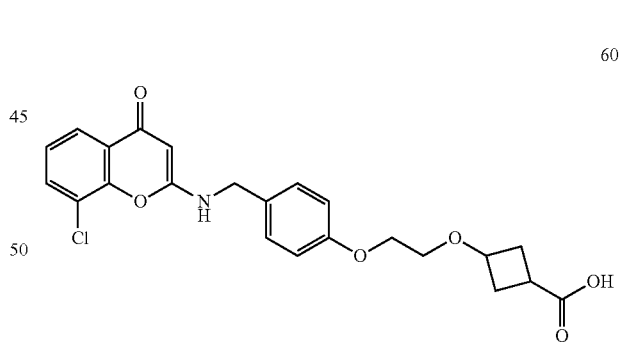

60

To a solution of methyl 3-(2-(4-(((8-chloro-4-oxo-chromen-2-yl)amino)methyl)phenoxy)ethoxy)cyclobutan-ecarboxylate (225 mg, 491 μmol) in the mixed solvent of MeOH (10 mL) and H$_2$O (3 mL) was added LiOH*H$_2$O (70.0 mg, 1.67 mmol) at room temperature and the resulting mixture was then stirred at room temperature for 12 hours. After the reaction was completed, the mixture was adjusted to pH~4 by addition of 4 N HCl and then concentrated in vacuo. The residue was purified by preparative HPLC to give 3-(2-(4-(((8-chloro-4-oxo-chromen-2-yl)amino) methyl)phenoxy)ethoxy)cyclobutanecarboxylic acid (5 mg, 2.3%) as a white foam. MS obsd. (ESI$^+$) [(M+H)$^+$]: 444.1.

Example 61

8-chloro-2-(4-hydroxypiperidin-1-yl)-3-iodo-chromen-4-one

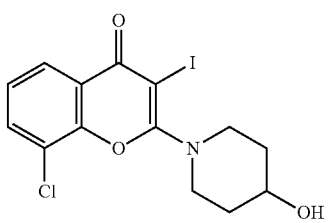

61

To a solution of 8-chloro-3-iodo-2-(1,2,4-triazol-1-yl)-chromen-4-one (Int-4, 452 mg, 1.21 mmol), piperidin-4-ol (159 mg, 1.57 mmol) in DMF (5 mL) was added $Cs_2CO_3$ (920 mg, 2.8 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 8-chloro-2-(4-hydroxypiperidin-1-yl)-3-iodo-chromen-4-one (90 mg, 18.3%) as a yellow foam. $^1$H NMR (400 MHz, DMSO-$d_6$) δ 7.86-7.93 (m, 2H), 7.37-7.46 (m, 1H), 4.83-4.88 (m, 1H), 3.91-3.99 (m, 2H), 3.74-3.84 (m, 1H), 3.36-3.46 (m, 2H), 1.87-1.97 (m, 2H), 1.52-1.65 (m, 2H). MS obsd. (ESI$^+$) [(M+H)$^+$]: 406.1.

Example 62

Tert-butyl 6-(8-chloro-4-oxo-chromen-2-yl)-2,6-diazaspiro[3.3]heptane-2-carboxylate

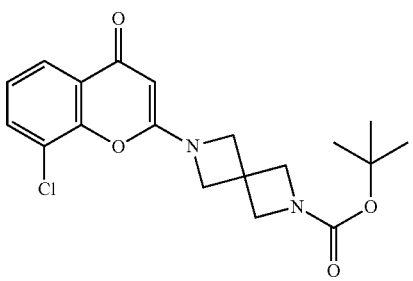

62

A solution of tert-butyl 2,6-diazaspiro[3.3]heptane-2-carboxylate oxalate (419 mg, 1.45 mmol), 8-chloro-2-(1,2,4-triazol-1-yl)-chromen-4-one (Int-3, 300 mg, 1.21 mmol) and $K_2CO_3$ (335 mg, 2.42 mmol) in DMF (10 mL) was stirred at 80° C. for 1 hour. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by silica-gel chromatography (MeOH:DCM=0 to 10%) to give tert-butyl 6-(8-chloro-4-oxo-chromen-2-yl)-2,6-diazaspiro[3.3]heptane-2-carboxylate (400 mg, 87.6%) as a yellow foam/H NMR (DMSO-76, 400 MHz): δ 7.87 (dd, 7=1.53, 7.89 Hz, 1H), 7.79 (dd, 7=1.53, 7.89 Hz, 1H), 7.37 (t, 7=7.83 Hz, 1H), 5.09 (s, 1H), 4.30 (s, 4H), 4.06 (s, 4H), 1.38 (s, 9H). MS obsd. (ESI$^+$) [(M+H)$^+$]: 377.1.

Example 63

Methyl 3-[6-(8-chloro-4-oxo-chromen-2-yl)-2,6-diazaspiro[3.3]heptane-2-carbonyl]benzoate

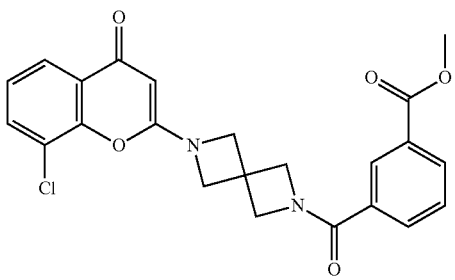

63

Step 1: Preparation of 8-chloro-2-(2,6-diazaspiro[3.3]heptan-2-yl)chromen-4-one

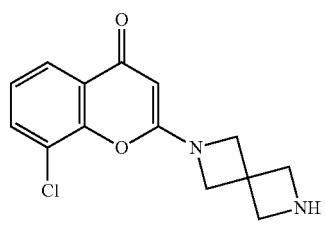

63a

A solution of tert-butyl 6-(8-chloro-4-oxo-chromen-2-yl)-2,6-diazaspiro[3.3]heptane-2-carboxylate (400 mg, 1.06 mmol) in trifluoroacetic acid (10 mL) was stirred at room temperature for 3 hours. After the reaction was completed, the mixture was concentrated in vacuo to give 8-chloro-2-(2,6-diazaspiro[3.3]heptan-2-yl)chromen-4-one (300 mg, 100%) as a yellow oil, which was used in the next step directly without further purification. MS obsd. (ESI$^+$) [(M+H)$^+$]:277.1.

Step 2: Preparation of methyl 3-[6-(8-chloro-4-oxo-chromen-2-yl)-2,6-diazaspiro[3.3]heptane-2-carbonyl]benzoate

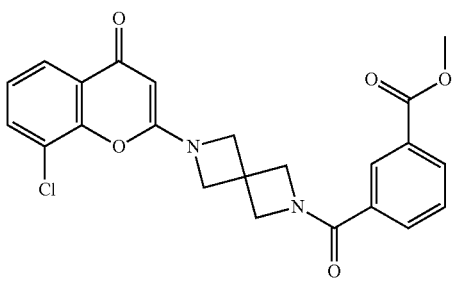

63

A solution of 8-chloro-2-(2,6-diazaspiro[3.3]heptan-2-yl)-chromen-4-one (100 mg, 0.36 mmol), 3-(methoxycarbonyl)benzoic acid (78.1 mg, 434 µmol), HATU (275 mg, 0.72) and TEA (182 mg, 1.81 mmol) in DCM (10 mL) was stirred at room temperature for 16 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo. The residue was purified by preparative HPLC to give methyl 3-[6-(8-chloro-4-oxo-chromen-2-yl)-2,6-diazaspiro[3.3]heptane-2-carbonyl]benzoate (10 mg, 6.3%) as yellow solid. $^1$H NMR (DMSO-d$_6$, 400 MHz): δ 8.18 (t, J=1.53 Hz, 1H), 8.09 (td, J=1.34, 7.82 Hz, 1H), 7.84-7.93 (m, 2H), 7.80 (dd, J=1.53, 7.89 Hz, 1H), 7.64 (t, J=7.70 Hz, 1H), 7.37 (t, J=7.83 Hz, 1H), 5.12 (s, 1H), 4.55 (s, 2H), 4.36 (s, 4H), 4.31 (s, 2H), 3.89 (s, 3H). MS obsd. (ESI$^+$) [(M+H)$^+$]: 439.1.

Example 64

3-(2-((2-(8-chloro-4-oxo-chromen-2-yl)-1-oxoisoindolin-5-yl)oxy)ethoxy)cyclobutanecarboxylic Acid

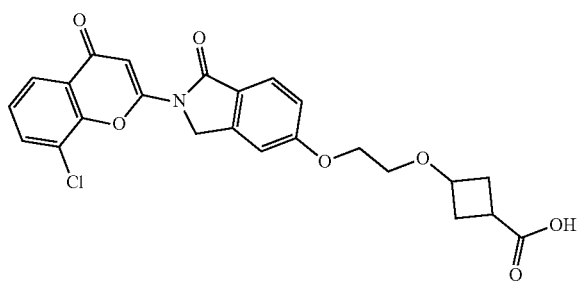

64

Step 1: Preparation of 2-(8-chloro-4-oxo-chromen-2-yl)-5-hydroxyisoindolin-1-one

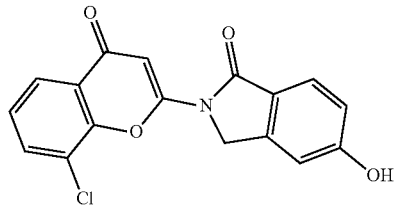

64a

To a solution of 2-(8-chloro-4-oxo-chromen-2-yl)-5-methoxyisoindolin-1-one (200 mg, 585 µmol) in DCM (5 mL) was added BBr$_3$ (1 M solution in DCM, 10 mL, 10 mmol) at room temperature and the resulting mixture was stirred at room temperature overnight. After the reaction was completed, the mixture was concentrated in vacuo and the residue was suspended in saturated NH$_4$Cl solution (30 mL). The solid was collected by filtration and dried in vacuo to give 2-(8-chloro-4-oxo-chromen-2-yl)-5-hydroxyisoindolin-1-one (150 mg, 78.2%) as a yellow solid, which was used in the next step directly without further purification. MS obsd. (ESI$^+$) [(M+H)$^+$]: 328.1.

Step 2: Preparation of methyl 3-(2-((2-(8-chloro-4-oxo-chromen-2-yl)-1-oxoisoindolin-5-yl)oxy)ethoxy)cyclobutanecarboxylate

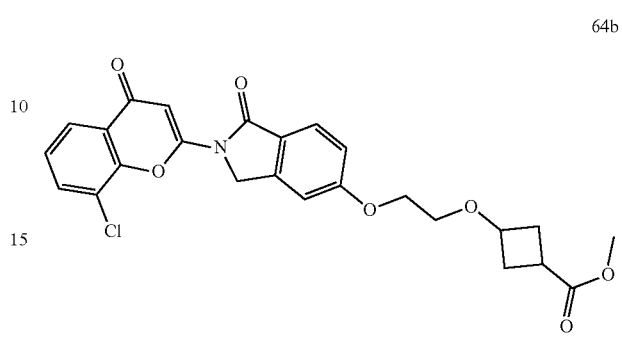

64b

To a solution of 2-(8-chloro-4-oxo-chromen-2-yl)-5-hydroxyisoindolin-1-one (120 mg, 366 µmol), methyl 3-[2-(p-tolylsulfonyloxy)ethoxy]cyclobutanecarboxylate (Int-8, 180 mg, 549 µmol) in DMF (5 mL) was added K$_2$CO$_3$ (118 mg, 857 µmol) at room temperature and the resulting mixture was then stirred at 60° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give methyl 3-(2-((2-(8-chloro-4-oxo-chromen-2-yl)-1-oxoisoindolin-5-yl)oxy)ethoxy)cyclobutanecarboxylate (177 mg, 99.9%) as a yellow foam, which was used in the next step directly without further purification. MS obsd. (ESI$^+$) [(M+H)$^+$]: 484.1.

Step 3: Preparation of 3-(2-((2-(8-chloro-4-oxo-chromen-2-yl)-1-oxoisoindolin-5-yl)oxy)ethoxy)cyclobutanecarboxylic Acid

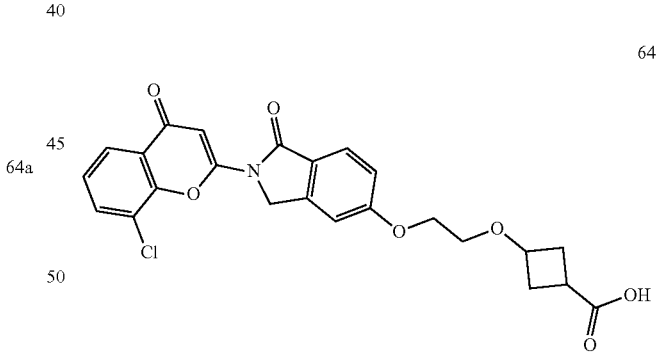

64

To a solution of methyl 3-(2-((2-(8-chloro-4-oxo-chromen-2-yl)-1-oxoisoindolin-5-yl)oxy)ethoxy)cyclobutanecarboxylate (100 mg, 207 µmol) in THF (4 mL) was added 3.0 M hydrogen chloride (1 mL, 3 mmol) and the resulting mixture was then stirred at 50° C. for 2 hours. After the reaction was completed, the mixture was then concentrated in vacuo and the residue was purified by preparative HPLC to give 3-(2-((2-(8-chloro-4-oxo-chromen-2-yl)-1-oxoisoindolin-5-yl)oxy)ethoxy)cyclobutanecarboxylic acid (5 mg, 5.15%) as a white foam. $^1$H NMR (400 MHz, DMSO-d$_6$) δ 12.07-12.42 (m, 1H), 7.96-8.00 (m, 2H), 7.78-7.82 (m, 1H), 7.48-7.54 (m, 1H), 7.37-7.41 (m, 1H), 7.13-7.18 (m, 2H), 5.17-5.20 (m, 2H), 3.92-4.25 (m, 3H), 3.66-3.71 (m, 2H), 2.86-2.96 (m, 1H), 2.35-2.45 (m, 2H), 2.11-2.20 (m, 1H), 1.94-2.04 (m, 1H). MS obsd. (ESI+) [(M+H)+]: 470.1.

Example 65

2-(8-chloro-4-oxo-chromen-2-yl)-7-methoxy-3,4-dihydroisoquinolin-1-one

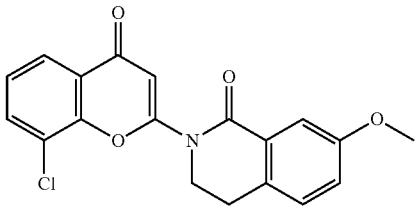

To a solution of 8-chloro-2-(1H-1,2,4-triazol-1-yl)-chromen-4-one (800 mg, 3.23 mmol), 7-methoxy-3,4-dihydroisoquinolin-1-one (700 mg, 3.95 mmol) in DMF (5 mL) was added $Cs_2CO_3$ (2.11 g, 6.46 mmol) at room temperature and the resulting mixture was then stirred at 80° C. for 2 hours. After the reaction was completed, the mixture was diluted with water (30 mL) and extracted with EtOAc (50 mL) three times. The combined organic layer was washed with brine, dried over anhydrous $Na_2SO_4$ and concentrated in vacuo. The residue was purified by preparative HPLC to give 2-(8-chloro-4-oxo-chromen-2-yl)-7-methoxy-3,4-dihydroisoquinolin-1-one (800 mg, 69.6%) as a yellow foam. $^1$H NMR (400 MHz, DMSO-$d_6$) δ 12.07-12.42 (m, 1H), 7.96-8.00 (m, 2H), 7.78-7.82 (m, 1H), 7.48-7.54 (m, 1H), 7.37-7.41 (m, 1H), 7.13-7.18 (m, 2H), 5.17-5.20 (m, 2H), 3.92-4.25 (m, 3H), 3.66-3.71 (m, 2H), 2.86-2.96 (m, 1H), 2.35-2.45 (m, 2H), 2.11-2.20 (m, 1H), 1.94-2.04 (m, 1H). MS obsd. (ESI+) [(M+H)+]: 356.1.

BIOLOGICAL EXAMPLES

Example 66: Engineered HepDES19 primary screen assay

The assay was employed to screen for novel cccDNA inhibitors. HepDES19 is a cccDNA-producing cell line. In this cell line, HBeAg in the cell culture supernatant as surrogate marker, as HBeAg production depends on cccDNA level and activity. HepDES19 is an engineered cell line which contains a 1.1 unit length HBV genome, and pgRNA transcription from the transgene is controlled by Tetracycline (Tet). In the absence of Tet, pgRNA transcription will be induced, but HBV e antigen (HBeAg) could not be produced from this pgRNA due to very short leader sequence before the HBeAg start codon and the start codon is disrupted. Only after cccDNA is formed, the missing leader sequence and start codon mutation would be restored from the 3'-terminal redundancy of pgRNA, and then HBeAg could be synthesized. Therefore, HBeAg could be used as a surrogate marker for cccDNA (Zhou, T. et al., Antiviral Res. (2006), 72(2), 116-124; Guo, H. et al., J. Virol. (2007), 81(22), 12472-12484).

HepDES19 cells were seeded at $2\times10^6$ cells per T150 flask and cultured with the culture medium (Dulbecco's Modified Eagle Medium: Nutrient Mixture F-12 [DMEM-F12, Gibco Cat. 11320-82], 10% Fetal Bovine Serum [FBS, Clontech Cat. 631101], 0.1 mM Non-Essential Amino Acids Solution [NEAA, Gibco Cat. 11140-050], 50 μg/mL Penicillin-Streptomycin [PS, Invitrogen Cat. 15140-163], 500 μg/mL Geneticin [G418, Invitrogen Cat. 10131-027]) containing 3 μg/mL Tet (Sigma, Cat. 87128) for 5 days. Cells were then seeded at $4\times10^6$ cells per T150 in the same culture medium as described above in the absence of Tet for 8 days. Cells were then harvested and frozen at density of $2\times10^6$ cells per mL. For compound testing, the frozen cells were thawed and seeded into 96-well plates at a density of $6\times10^4$ cells per well. At 24 hours after seeding, half log serial dilutions of compounds made with Dimethyl sulfoxide (DMSO, Sigma, Cat. D2650) were further diluted with the same culture medium as described above before they were added to the cells to reach desired final compound concentrations and 1% DMSO concentration. Plates were then incubated at 37° C. for another 5 days before measurement of HBeAg level and cell viability. Intracellular HBeAg level were measured with enzyme-linked immunosorbent assay (ELISA) kit (Shanghai Kehua Diagnostic Medical Products Co., Ltd). Cell viability was assessed using Cell Counting Kit-8 (Donjindo, Cat. CK04-20). $IC_{50}$ values were derived from the dose-response curve using 4 parameter logistic curve fit method.

The compounds of the present invention were tested for their capacity to inhibit extracellular HBeAg level as described herein. The compounds of this invention were found to have $IC_{50}$ below 50 μM. Particular compounds of formula (I) were found to have $IC_{50}$ below 5.0 μM. Results of HepDES19 primary screen assay are given in Table 1.

TABLE 1

Activity data in HepDES19 primary screen assay

| Example No. | $IC_{50}$ (μM) |
| --- | --- |
| 3 | 0.64 |
| 4 | 3.60 |
| 7 | 1.66 |
| 8 | 0.32 |
| 11 | 3.12 |
| 17 | 10.75 |
| 20 | 50 |
| 21 | 11.03 |
| 22 | 11.90 |
| 23 | 11.94 |
| 24 | 13.86 |
| 25 | 16.19 |
| 26 | 20.60 |
| 27 | 23.44 |
| 28 | 24.30 |
| 29 | 24.86 |
| 30 | 25.90 |
| 31 | 26.83 |
| 32 | 33.73 |
| 33 | 35.32 |
| 34 | 44.58 |
| 35 | 44.60 |
| 41 | 3.99 |
| 42 | 4.34 |
| 43 | 4.78 |
| 44 | 5.44 |
| 45 | 8.58 |
| 46 | 9.66 |
| 47 | 10.72 |
| 48 | 12.12 |
| 49 | 12.38 |
| 50 | 14.06 |
| 51 | 14.76 |
| 52 | 14.96 |
| 53 | 15.02 |
| 54 | 15.99 |

TABLE 1-continued

Activity data in HepDES19 primary screen assay

| Example No. | $IC_{50}$ (μM) |
|---|---|
| 55 | 16.68 |
| 56 | 19.62 |
| 57 | 19.96 |
| 58 | 23.42 |
| 59 | 24.41 |
| 60 | 30.79 |
| 61 | 30.86 |
| 62 | 33.19 |
| 63 | 31.67 |
| 64 | 36.63 |
| 65 | 37.59 |

Example 67: Cryopreserved Primary Human Hepatocytes (PHH) Assay

This assay is used to confirm the anti-HBV effect of the compounds in HBV PHH infection assay. Cryopreserved PHH (BioreclamationIVT, Lot YJM) was thawed at 37° C. and gently transferred into pre-warmed InVitroGRO HT medium (BioreclamationIVT, Cat. S03317).

The mixture was centrifuged at 70 relative centrifugal force (RCF) for 3 mins at RT, and the supernatant was discarded. Pre-warmed InVitroGRO CP medium (BioreclamationIVT, Cat #S03316) was added to the cell pellet to gently re-suspend cells. The cells were seeded at the density of $5.8 \times 10^4$ cells per well to collagen I coated 96-well plate (Gibco, Cat. A1142803) with the InVitroGRO CP medium. All plates were incubated at 37° C. with 5% $CO_2$ and 85% humidity.

At 20 hours after plating, the medium was changed to PHH culture medium (Dulbecco's Modified Eagle Medium (DMEM)/F12 (1:1) (Gibco, Cat. 11320-033), 10% fetal bovine serum (Gibco Cat. 10099141), 100 U/mL penicillin, 100 μg/mL streptomycin (Gibco, Cat. 151401-122), ng/mL human epidermal growth factor (Invitrogen Cat. PHG0311L), 20 ng/mL dexamethasone (Sigma, Cat. D4902) and 250 ng/mL human recombinant insulin (Gibco, Cat. 12585-014)). And the cells were incubated at 37° C. with 5% $CO_2$ and 85% humidity for 4 hours. The medium was then changed to pre-warmed PHH culture medium containing 4% polyethylene glycol (PEG) MW8000 (Sigma, Cat. P1458-50ML) and 1% DMSO (Sigma, Cat. D2650). $5.8 \times 10^6$ genomic equivalents of HBV were added into the medium.

At 24 hours post-infection, the cells were gently washed with PBS and refreshed with PHH culture medium supplemented with 1% DMSO, and 0.25 mg/mL Matrix gel (Corning, Cat. 356237) at 200 μL per well. All plates were immediately placed in at 37° C. $CO_2$ incubator. 24 hours later, serial dilutions of compounds made with DMSO were further diluted with the same culture medium (PHH culture medium supplemented with 1% DMSO and 0.25 mg/mL Matrix gel as described above) before they were added to the cells to reach desired final compound concentrations and 1% DMSO concentration. The medium containing the compounds were refreshed every three days.

At 9 days post-compound treatment, extracellular HBsAg level were measured with Chemiluminescence Immuno Assay (CLIA) kit (Autobio, HBsAg Quantitative CLIA). Extracellular HBV DNA was extracted by MagNA Pure 96 system (Roche) and then determined by quantitative PCR with the following primers and probe:

```
HBV-Forward Primer (SEQ ID NO: 1):
AAGAAAAACCCCGCCTGTAA (5' to 3');

HBV-Reverse Primer (SEQ ID NO: 2):
CCTGTTCTGACTACTGCCTCTCC (5' to 3');

HBV-Probe:
5' + tetramethylrhodamine + SEQ ID NO: 3 + black hole quencher 2-3',
``` wherein SEQ ID NO: 3 is CCTGATGTGATGTTCTC-CATGTTCAGC.

HBsAg $IC_{50}$ and HBV DNA $IC_{50}$ values were derived from the dose-response curve using 4 parameter logistic curve fit method. Test results of the compounds in Cryopreserved PHH assay are given in Table 2.

TABLE 2

HBsAg $IC_{50}$ data in Cryopreserved PHH assay

| Example No. | HBsAg $IC_{50}$ (μM) |
|---|---|
| 1 | 2.86 |
| 2 | 4.36 |
| 3 | 6.47 |
| 4 | 6.58 |
| 5 | 7.42 |
| 6 | 9.53 |
| 7 | 10.01 |
| 9 | 14.14 |
| 10 | 24.33 |
| 12 | 34.24 |
| 13 | 36.33 |
| 14 | 36.34 |
| 15 | 37.57 |
| 16 | 40.32 |
| 18 | 42.95 |
| 19 | 31.63 |
| 36 | 0.61 |
| 37 | 1.06 |
| 38 | 38.46 |
| 39 | 38.52 |
| 40 | 34.59 |

The invention claimed is:

1. A compound selected from the group consisting of:
3-(2-(4-(8-chloro-4-oxo-chromene-2-carboxamido)-3-fluorophenoxy)ethoxy)cyclobutanecarboxylic acid;
3-(2-(4-(8-chloro-4-oxo-chromene-2-carboxamido)-3-methylphenoxy)ethoxy)cyclobutanecarboxylic acid;
6-chloro-N-(4-chloro-2-methylphenyl)-3-methyl-4-oxo-chromene-2-carboxamide;
3-(2-(4-(8-chloro-4-oxo-chromene-2-carboxamido)-3-(trifluoromethyl)phenoxy)ethoxy)cyclobutanecarboxylic acid;
8-chloro-4-oxo-N-(5-(trifluoromethyl)-1,3,4-thiadiazol-2-yl)-chromene-2-carboxamide;
3-(5-chloro-2-(8-chloro-4-oxo-chromene-2-carboxamido)phenoxy)cyclobutane-1-carboxylic acid;
8-chloro-N-(4-chloro-2-methylphenyl)-4-oxo-chromene-2-carboxamide;
8-chloro-N-(2,4-dichlorobenzyl)-4-oxo-chromene-2-carboxamide;
N-(5-bromo-3-methylpyridin-2-yl)-8-chloro-4-oxo-chromene-2-carboxamide;
4-(5-chloro-2-(6,8-dichloro-4-oxo-chromene-2-carboxamido)phenoxy)butanoic acid;
8-chloro-N-(4-chloro-2-(trifluoromethyl)phenyl)-4-oxo-chromene-2-carboxamide;
6,8-dichloro-N-(4-chloro-2-methylphenyl)-4-oxo-chromene-2-carboxamide;
8-chloro-4-oxo-N-(o-tolyl)-chromene-2-carboxamide;
4-(8-chloro-4-oxo-chromene-2-carboxamido)-3-methylbenzoic acid;
2-(2-(4-(8-chloro-4-oxo-chromene-2-carboxamido)-3-methylphenoxy)ethoxy)acetic acid;
2-(5-chloro-2-(8-chloro-4-oxo-chromene-2-carboxamido)phenoxy)acetic acid;
methyl 3-(8-chloro-4-oxo-chromene-2-carboxamido)-4-methylbenzoate;
2-(2-(5-chloro-2-(6,8-dichloro-4-oxo-chromene-2-carboxamido)phenoxy)ethoxy)acetic acid;
N-(5-bromo-4-methylpyridin-2-yl)-8-chloro-4-oxo-chromene-2-carboxamide;
2-(2-(5-chloro-2-(8-chloro-4-oxo-chromene-2-carboxamido)phenoxy)ethoxy)acetic acid;
methyl 5-chloro-2-(8-chloro-4-oxo-chromene-2-carboxamido)benzoate;
methyl 4-((8-chloro-4-oxo-chromene-2-carboxamido)methyl)benzoate;
methyl 4-(8-chloro-4-oxo-chromene-2-carboxamido)-3-methylbenzoate;
N-(1-(4-bromophenyl)ethyl)-8-chloro-4-oxo-chromene-2-carboxamide;
8-chloro-N-(4-hydroxy-2-methylphenyl)-4-oxo-chromene-2-carboxamide;
N-(5-bromo-3-methoxypyridin-2-yl)-8-chloro-4-oxo-chromene-2-carboxamide;
3-(2-(5-chloro-2-(8-chloro-4-oxo-chromene-2-carboxamido)phenoxy)ethoxy)cyclobutane-1-carboxylic acid; and
ethyl 5-(8-chloro-4-oxo-chromene-2-carboxamido)-1,3,4-thiadiazole-2-carboxylate;
or a pharmaceutically acceptable salt thereof.

2. A pharmaceutical composition comprising a compound in accordance with claim 1 and a therapeutically inert carrier.

\* \* \* \* \*